(12) United States Patent
Lim et al.

(10) Patent No.: US 12,207,957 B2
(45) Date of Patent: Jan. 28, 2025

(54) SURGICAL FRAME INCORPORATING ELECTRO-MAGNETIC IMAGING DEVICE IN COMBINATION WITH RADIATION-MITIGATION SYSTEM

(71) Applicant: WARSAW ORTHOPEDIC, INC., Warsaw, IN (US)

(72) Inventors: Roy K. Lim, Germantown, TN (US); Richard A. Hynes, Melbourne Beach, FL (US); Olumide Aruwajoye, Collierville, TN (US); Matthew M. Morrison, Cordova, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 1016 days.

(21) Appl. No.: 17/082,432

(22) Filed: Oct. 28, 2020

(65) Prior Publication Data
US 2022/0125392 A1 Apr. 28, 2022

(51) Int. Cl.
*A61B 6/04* (2006.01)
*A61B 6/00* (2024.01)
(Continued)

(52) U.S. Cl.
CPC ............ *A61B 6/0407* (2013.01); *A61B 6/107* (2013.01); *A61B 6/4021* (2013.01); *A61B 6/42* (2013.01);
(Continued)

(58) Field of Classification Search
CPC ..... A61B 6/0407; A61B 6/107; A61B 6/4452; A61B 6/42; A61B 6/4021; A61B 6/08;
(Continued)

(56) References Cited

U.S. PATENT DOCUMENTS 4,062,518 A 12/1977 Stivender et al.
4,254,763 A 3/1981 McCready et al.
(Continued)

FOREIGN PATENT DOCUMENTS

CN 201189182 2/2009
CN 204654975 9/2015
(Continued)

OTHER PUBLICATIONS

International Search Report and Written Opinion dated Nov. 23, 2021 in PCT/US2021/049747.

*Primary Examiner* — David R Hare
*Assistant Examiner* — Deborah Talitha Gedeon

(57) ABSTRACT

A surgical frame incorporating an electromagnetic-radiation imaging device, and a radiation-mitigation system for use with the surgical frame are provided. The surgical frame can be capable of reconfiguration before, during, or after surgery, and can include a main beam that can be rotated, raised/lowered, and tilted upwardly/downwardly to afford positioning and repositioning of a patient supported thereon. The surgical frame can support the electromagnetic-radiation imaging device. One of an emitter and a receiver of the electromagnetic-radiation imaging device can be positioned under the main beam of the surgical frame, and the other of the emitter and the receiver of the electromagnetic-radiation imaging device can be positioned over the main beam of the surgical frame. The radiation-mitigation system can serve to intercept/block and mitigate at least some of the scatter of the electromagnetic radiation from the emitter.

20 Claims, 40 Drawing Sheets

(51) Int. Cl.
 *A61B 6/08* (2006.01)
 *A61B 6/10* (2006.01)
 *A61B 6/40* (2024.01)
 *A61B 6/42* (2024.01)
 *A61G 13/12* (2006.01)

(52) U.S. Cl.
 CPC ............ *A61B 6/4452* (2013.01); *A61G 13/12* (2013.01); *A61B 6/08* (2013.01); *A61B 6/4258* (2013.01); *A61G 2200/325* (2013.01); *A61G 2210/50* (2013.01)

(58) Field of Classification Search
 CPC ... A61B 6/0414; A61B 6/0421; A61B 6/0428; A61B 6/0435; A61B 6/0442; A61B 6/045; A61B 6/0464; A61B 6/0471; A61B 6/4208; A61B 6/4216; A61B 6/4225; A61B 6/4233; A61B 6/4241; A61B 6/425; A61B 6/4258; A61B 6/4266; A61B 6/4275; A61B 6/4283; A61B 6/4291; A61B 6/032; A61B 6/4441; A61B 6/54; A61B 6/035; A61G 13/12; A61G 13/1205; A61G 13/121; A61G 13/1215; A61G 13/122; A61G 13/1225; A61G 13/123; A61G 13/124; A61G 13/1245; A61G 13/125; A61G 13/1255; A61G 13/126; A61G 2200/30; A61G 2200/32; A61G 2200/322; A61G 2200/325; A61G 2200/327
 See application file for complete search history.

(56) References Cited

U.S. PATENT DOCUMENTS

| | | |
|---|---|---|
| 4,321,917 A | 3/1982 | Campbell |
| 4,730,609 A | 3/1988 | McConnell |
| 5,027,832 A | 7/1991 | Williams, Jr. |
| 5,396,904 A | 3/1995 | Hartigan, Jr. |
| 6,481,888 B1 | 11/2002 | Morgan |
| 8,079,365 B2 | 12/2011 | Block et al. |
| 9,072,646 B2 | 7/2015 | Skripps et al. |
| 9,855,178 B2 | 1/2018 | Rogers |
| 10,576,006 B2 | 2/2020 | Lim et al. |
| 10,835,439 B2 | 11/2020 | Lim et al. |
| 10,893,996 B2 | 1/2021 | Lim et al. |
| 2003/0091152 A1* | 5/2003 | Dietz ..................... A61B 6/107 378/197 |
| 2006/0124871 A1* | 6/2006 | Ballsieper ............ A61B 6/4423 250/516.1 |
| 2008/0031422 A1* | 2/2008 | Barkow ................. A61B 6/107 378/203 |
| 2010/0293713 A1* | 11/2010 | Sharps ................... A61G 13/06 5/83.1 |
| 2016/0015344 A1 | 1/2016 | Fortuna et al. |
| 2016/0038365 A1* | 2/2016 | Conner ................ A61B 6/0407 5/601 |
| 2018/0193104 A1 | 7/2018 | Beale et al. |
| 2019/0000702 A1* | 1/2019 | Lim ..................... A61G 7/1019 |
| 2019/0000707 A1 | 1/2019 | Lim et al. |
| 2019/0142353 A1 | 5/2019 | Stegehuis et al. |
| 2019/0209105 A1 | 7/2019 | Bornvall |
| 2019/0282316 A1 | 9/2019 | Fields et al. |
| 2019/0282329 A1 | 9/2019 | Fields et al. |
| 2019/0282330 A1 | 9/2019 | Fields et al. |
| 2020/0188208 A1 | 6/2020 | Lim et al. |

FOREIGN PATENT DOCUMENTS

| | | | | |
|---|---|---|---|---|
| CN | 108451537 A | * | 8/2018 | ............ A61B 6/027 |
| DE | 102012212104 | | 1/2014 | |
| DE | 102013220204 | | 4/2015 | |
| WO | WO-2015035109 A1 | * | 3/2015 | ........... A61B 6/0407 |

\* cited by examiner

SURGICAL FRAME INCORPORATING ELECTRO-MAGNETIC IMAGING DEVICE IN COMBINATION WITH RADIATION-MITIGATION SYSTEM

FIELD

The present technology generally relates to a surgical frame incorporating an electro-magnetic imaging device.

BACKGROUND

Common imaging techniques can employ electromagnetic radiation to facilitate imaging of anatomical structures of a patient before, during, and after surgery. For example, fluoroscopy is one of these common imaging techniques. Typically, the apparatus facilitating fluoroscopy includes an emitter for emitting X-rays directed towards a patient, and a receiver for receiving the emitted X-rays directed towards the patient after passing through the patient. The fluoroscopy apparatus can be used to image specific portions of the patient's body. The fluoroscopy apparatus is typically separate from surgical frames supporting the patient's body, and must be positioned relative to the patient's body and the surgical frame during use thereof. Use of such separate fluoroscopy apparatus can interfere with manipulation of the surgical frame. Furthermore, even when portions of the fluoroscopy apparatus previously have been incorporated into some surgical frames, the movement of the fluoroscopy apparatus may be somewhat limited, and such movement of the fluoroscopy apparatus may interfere with the manipulation of the surgical frame. Therefore, there is a need for a surgical frame that incorporates an electro-magnetic imaging device that affords increased movement of the imaging device, while also limiting interference with the manipulation of the surgical frame. As discussed below, an emitter and a receiver of an electro-magnetic imaging device can be supported by portions incorporated into the surgical frame to provide increased movement thereof and to limit interference with movement of portions of the surgical frame.

SUMMARY

The techniques of this disclosure generally relate to a surgical frame incorporating an electro-magnetic imaging device.

In one aspect, the present disclosure provides a surgical frame incorporating at least a portion of an electromagnetic-radiation imaging device, the surgical frame including a first support portion, a second support portion, a main beam, a translating beam, a first support post, a second support post, a transom, and the electromagnetic-radiation imaging device, the main beam being spaced from the ground by at least the first support portion and the second support portion, the translating beam being positioned under the main beam, and being moveably attached at a first end thereof relative to the first support portion and moveably attached at a second end thereof relative to the second support portion, the first support post being attached relative to the first support portion, the second support post being attached relative to the second support portion, the transom extending between the first support post and the second support post, the electromagnetic-radiation imaging device including an emitter and a receiver, one of the emitter and the receiver being supported and moveably attached relative to the translating beam underneath the main beam, and the other of the emitter and the receiver being supported by and moveably attached to the transom over the main beam; where the translating beam and the one of the emitter and the receiver attached thereto are moveable between a first position at or adjacent the first lateral side of the surgical frame and a second position at or adjacent the second lateral side of the surgical frame, the one of the emitter and the receiver is moveable along the translating beam between a first position at or adjacent the first support portion and a second position at or adjacent the second support portion, and the other of the emitter and the receiver is moveable along the transom between a first position at or adjacent the first support post and a second position at or adjacent the second support post.

In one aspect, the present disclosure provides a surgical frame incorporating at least a portion of an electromagnetic-radiation imaging device, the surgical frame including a first support portion, a second support portion, a translating beam, a first support post, a second support post, a transom, and the electromagnetic-radiation imaging device, the translating beam being moveably attached at a first end thereof relative to the first support portion and moveably attached at a second end thereof relative to the second support portion, the first support post being attached relative to the first support portion, the second support post being attached relative to the second support portion, the transom extending between the first support post and the second support post, the electromagnetic-radiation imaging device including an emitter and a receiver, one of the emitter and the receiver being supported and moveably attached relative to the translating beam, and the other of the emitter and the receiver being supported by and moveably attached to the transom; where the translating beam and the one of the emitter and the receiver attached thereto are moveable between a first position at or adjacent the first lateral side of the surgical frame and a second position at or adjacent the second lateral side of the surgical frame, the one of the emitter and the receiver is moveable along the translating beam between a first position at or adjacent the first support portion and a second position at or adjacent the second support portion, and the other of the emitter and the receiver is moveable along the transom between a first position at or adjacent the first support post and a second position at or adjacent the second support post.

In one aspect, the present disclosure provides a surgical frame incorporating at least a portion of an electromagnetic-radiation imaging device, the surgical frame including first support portion, a second support portion, a beam extending between the first support portion and the second support portion, a first support post, a second support post, a transom, and the electromagnetic-radiation imaging device, the translating beam being moveably attached at a first end thereof relative to the first support portion and moveably attached at a second end thereof relative to the second support portion, the first support post being attached relative to the first support portion, the second support post being attached relative to the second support portion, the transom extending between the first support post and the second support post, the electromagnetic-radiation imaging device including an emitter and a receiver, the emitter being supported and moveably attached relative to the translating beam, and the receiver being supported by and moveably attached to the transom; where the emitter is moveable along the beam extending between the first support portion and the second support portion between a first position at or adjacent the first support portion and a second position at or adjacent the second support portion, and the receiver is moveable along the transom between a first position at or adjacent the first support post and a second position at or adjacent the second support post.

The details of one or more aspects of the disclosure are set forth in the accompanying drawings and the description below. Other features, objects, and advantages of the techniques described in this disclosure will be apparent from the description and drawings, and from the claims.

Figure 1:
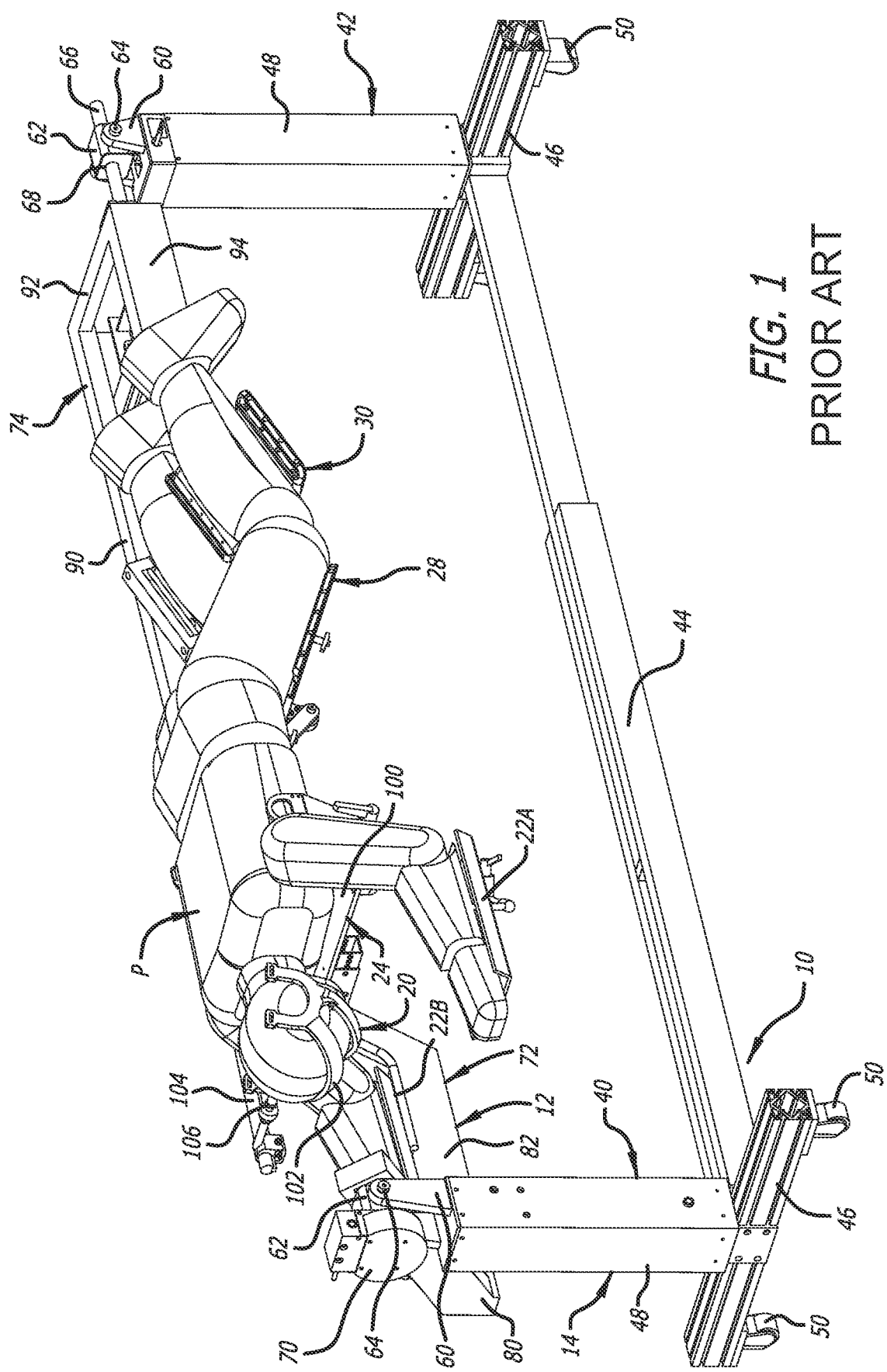
FIG. 1 is a top perspective view that illustrates a prior art surgical frame with a patient positioned thereon in a prone position.
Figure 2:
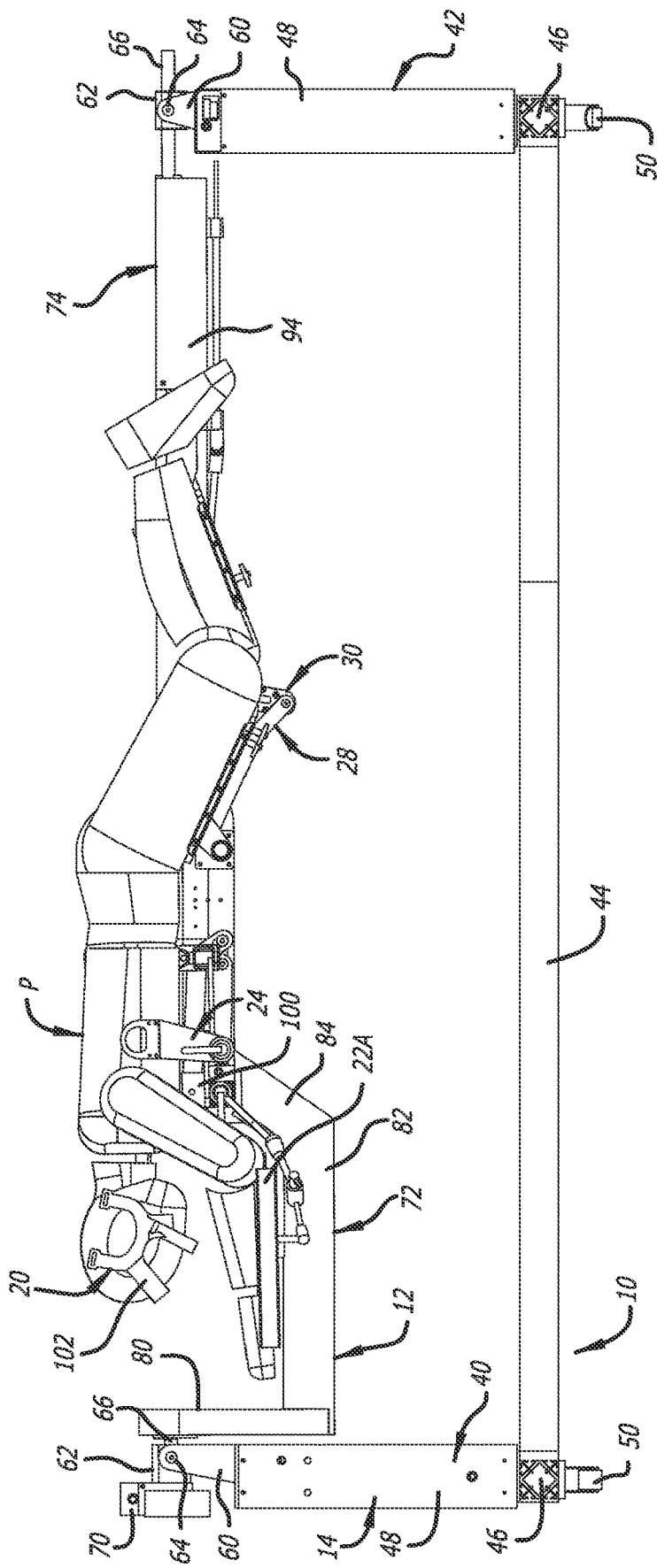
FIG. 2 is a side elevational view that illustrates the surgical frame of FIG. 1 with the patient positioned thereon in a prone position.
Figure 3:
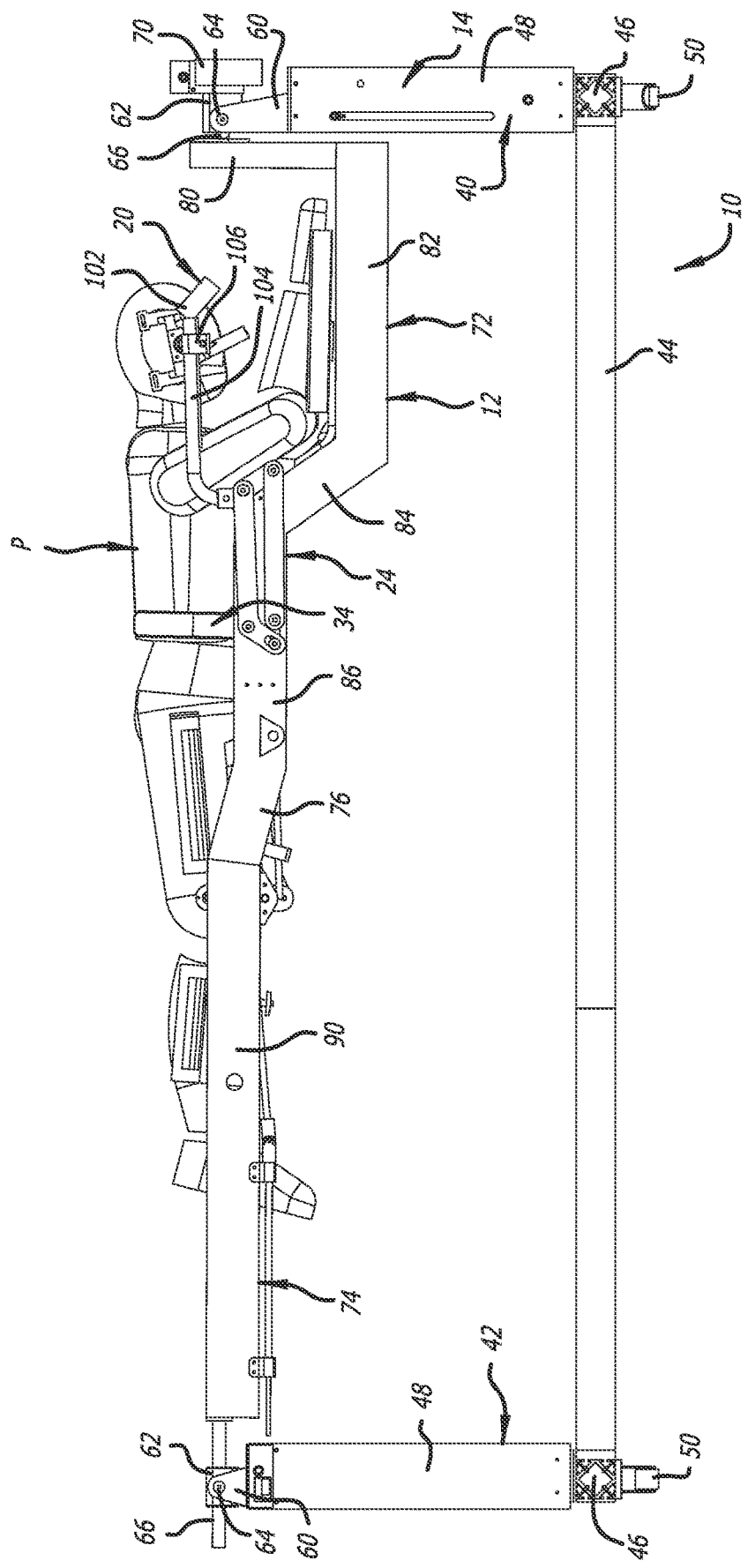
FIG. 3 is another side elevational view that illustrates the surgical frame of FIG. 1 with the patient positioned thereon in a prone position.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

FIGS. 1-26 depict a prior art embodiment and components of a surgical support frame generally indicated by the numeral 10. FIGS. 1-26 were previously described in U.S. Ser. No. 15/239,256, which is hereby incorporated by reference herein in its entirety. Furthermore, FIGS. 27-30 were previously described in U.S. Ser. No. 15/639,080, which is hereby incorporated by reference herein in its entirety.

As discussed below, the surgical frame 10 serves as an exoskeleton to support the body of the patient P as the patient's body is manipulated thereby, and, in doing so, serves to support the patient P such that the patient's spine does not experience unnecessary torsion.

The surgical frame 10 is configured to provide a relatively minimal amount of structure adjacent the patient's spine to facilitate access thereto and to improve the quality of imaging available before and during surgery. Thus, the surgeon's workspace and imaging access are thereby increased. Furthermore, radiolucent or low magnetic susceptibility materials can be used in constructing the structural components adjacent the patient's spine in order to further enhance imaging quality.

The surgical frame 10 has a longitudinal axis and a length therealong. As depicted in FIGS. 1-5, for example, the surgical frame 10 includes an offset structural main beam 12 and a support structure 14. The offset main beam 12 is spaced from the ground by the support structure 14. As discussed below, the offset main beam 12 is used in supporting the patient P on the surgical frame 10 and various support components of the surgical frame 10 that directly contact the patient P (such as a head support 20, arm supports 22A and 22B, torso-lift supports 24 and 160, a sagittal adjustment assembly 28 including a pelvic-tilt mechanism 30 and a leg adjustment mechanism 32, and a coronal adjustment assembly 34). As discussed below, an operator such as a surgeon can control actuation of the various support components to manipulate the position of the patient's body. Soft straps (not shown) are used with these various support components to secure the patient P to the frame and to enable either manipulation or fixation of the patient P. Reusable soft pads can be used on the load-bearing areas of the various support components.

Figure 4:
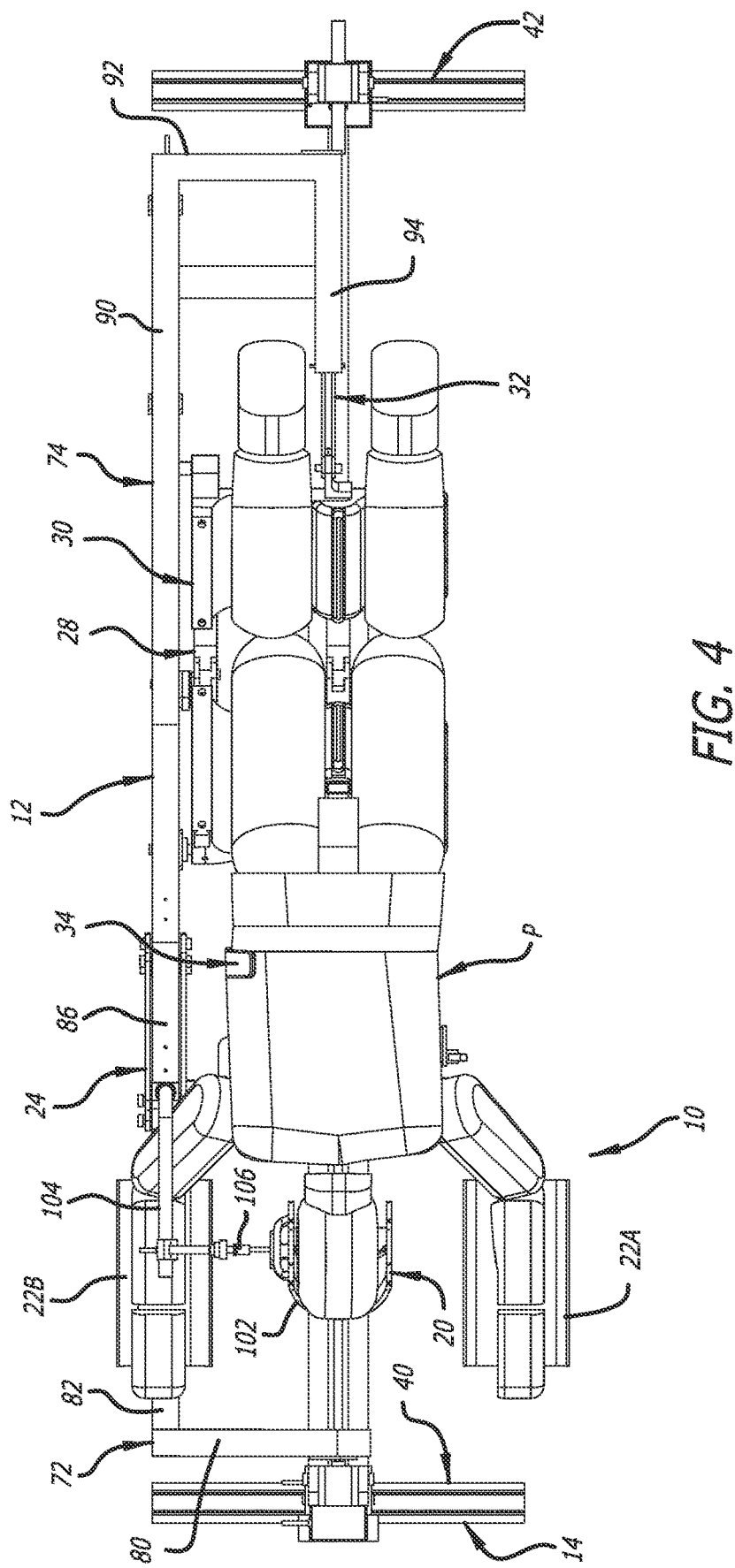
FIG. 4 is a top plan view that illustrates the surgical frame of FIG. 1 with the patient positioned thereon in a prone position.
Figure 5:
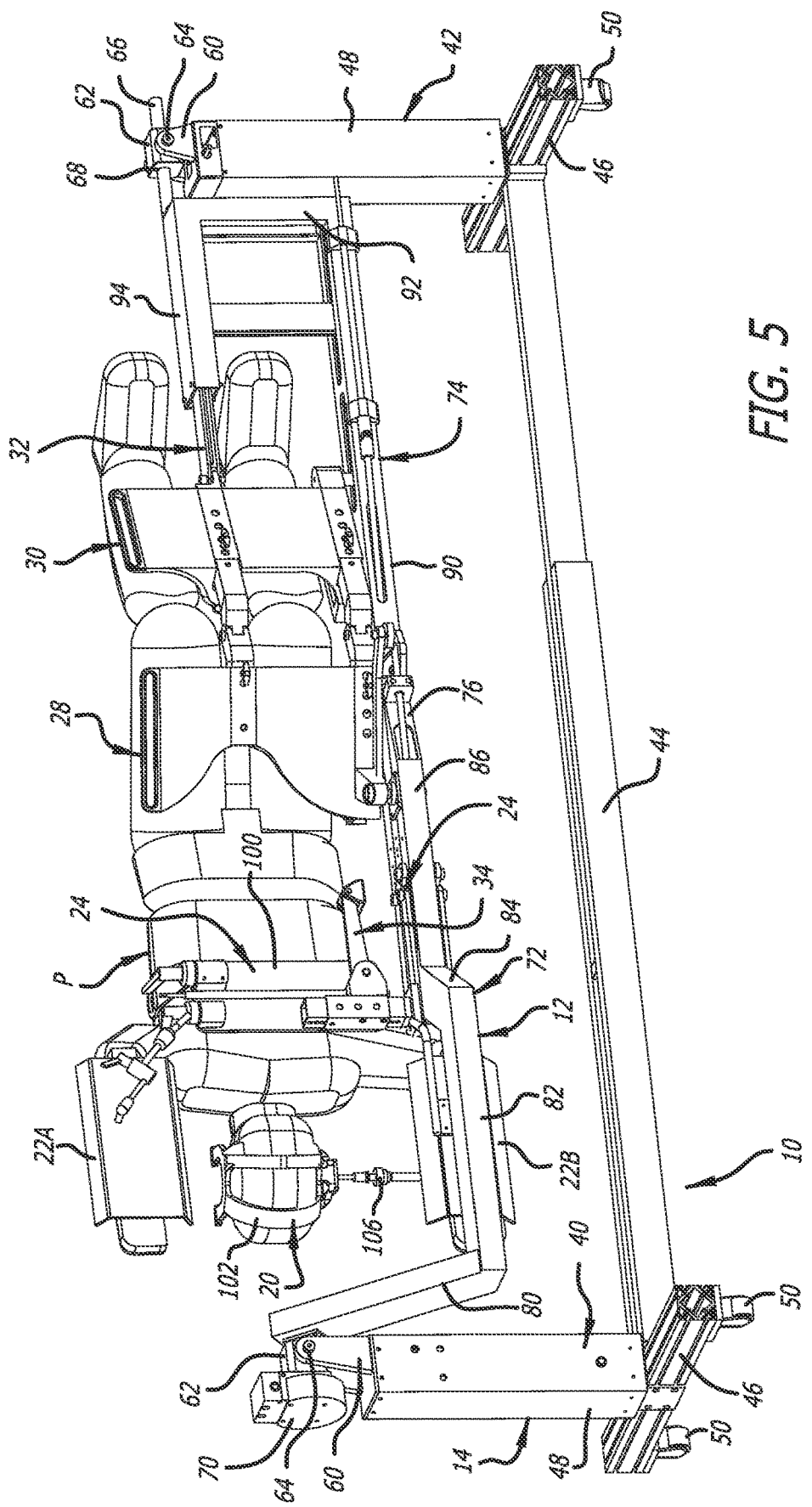
FIG. 5 is a top perspective view that illustrates the surgical frame of FIG. 1 with the patient positioned thereon in a lateral position.

The offset main beam 12 is used to facilitate rotation of the patient P. The offset main beam 12 can be rotated a full 360° before and during surgery to facilitate various positions of the patient P to afford various surgical pathways to the patient's spine depending on the surgery to be performed. For example, the offset main beam 12 can be positioned to place the patient P in a prone position (e.g., FIGS. 1-4), a lateral position (e.g., FIG. 5), and in a position 45° between the prone and lateral positions. Furthermore, the offset main beam 12 can be rotated to afford anterior, posterior, lateral, anterolateral, and posterolateral pathways to the spine. As such, the patient's body can be flipped numerous times before and during surgery without compromising sterility or safety. The various support components of the surgical frame 10 are strategically placed to further manipulate the patient's body into position before and during surgery. Such intraoperative manipulation and positioning of the patient P affords a surgeon significant access to the patient's body. To illustrate, when the offset main beam 12 is rotated to position the patient P in a lateral position, as depicted in FIG. 5, the head support 20, the arm supports 22A and 22B, the torso-lift support 24, the sagittal adjustment assembly 28, and/or the coronal adjustment assembly 34 can be articulated such that the surgical frame 10 is OLIF-capable or DLIF-capable.

As depicted in FIG. 1, for example, the support structure 14 includes a first support portion 40 and a second support portion 42 interconnected by a cross member 44. Each of the first and second support portions 40 and 42 include a horizontal portion 46 and a vertical support post 48. The horizontal portions 46 are connected to the cross member 44, and casters 50 can be attached to the horizontal portions 46 to facilitate movement of the surgical frame 10.

The vertical support posts 48 can be adjustable to facilitate expansion and contraction of the heights thereof. Expansion and contraction of the vertical support posts 48 facilitates raising and lowering, respectively, of the offset main beam 12. As such, the vertical support posts 48 can be adjusted to have equal or different heights. For example, the vertical support posts 48 can be adjusted such that the vertical support post 48 of the second support portion 42 is raised 12 inches higher than the vertical support post 48 of the first support portion 40 to place the patient P in a reverse Trendelenburg position.

Furthermore, cross member 44 can be adjustable to facilitate expansion and contraction of the length thereof. Expansion and contraction of the cross member 44 facilitates lengthening and shortening, respectively, of the distance between the first and second support portions 40 and 42.

The vertical support post 48 of the first and second support portions 40 and 42 have heights at least affording rotation of the offset main beam 12 and the patient P positioned thereon. Each of the vertical support posts 48 include a clevis 60, a support block 62 positioned in the clevis 60, and a pin 64 pinning the clevis 60 to the support block 62. The support blocks 62 are capable of pivotal movement relative to the clevises 60 to accommodate different heights of the vertical support posts 48. Furthermore, axles 66 extending outwardly from the offset main beam 12 are received in apertures 68 formed on the support blocks 62. The axles 66 define an axis of rotation of the offset main beam 12, and the interaction of the axles 66 with the support blocks 62 facilitate rotation of the offset main beam 12.

Furthermore, a servomotor 70 can be interconnected with the axle 66 received in the support block 62 of the first support portion 40. The servomotor 70 can be computer controlled and/or operated by the operator of the surgical frame 10 to facilitate controlled rotation of the offset main beam 12. Thus, by controlling actuation of the servomotor 70, the offset main beam 12 and the patient P supported thereon can be rotated to afford the various surgical pathways to the patient's spine.

As depicted in FIGS. 1-5, for example, the offset main beam 12 includes a forward portion 72 and a rear portion 74. The forward portion 72 supports the head support 20, the arm supports 22A and 22B, the torso-lift support 24, and the coronal adjustment assembly 34, and the rear portion 74 supports the sagittal adjustment assembly 28. The forward and rear portions 72 and 74 are connected to one another by connection member 76 shared therebetween. The forward portion 72 includes a first portion 80, a second portion 82, a third portion 84, and a fourth portion 86. The first portion 80 extends transversely to the axis of rotation of the offset main beam 12, and the second and fourth portions 82 and 86 are aligned with the axis of rotation of the offset main beam 12. The rear portion 74 includes a first portion 90, a second portion 92, and a third portion 94. The first and third portions 90 and 94 are aligned with the axis of rotation of the offset main beam 12, and the second portion 92 extends transversely to the axis of rotation of the offset main beam 12.

The axles 66 are attached to the first portion 80 of the forward portion 72 and to the third portion 94 of the rear portion 74. The lengths of the first portion 80 of the forward portion 72 and the second portion 92 of the rear portion 74 serve in offsetting portions of the forward and rear portions 72 and 74 from the axis of rotation of the offset main beam 12. This offset affords positioning of the cranial-caudal axis of patient P approximately aligned with the axis of rotation of the offset main beam 12.

Programmable settings controlled by a computer controller (not shown) can be used to maintain an ideal patient height for a working position of the surgical frame 10 at a near-constant position through rotation cycles, for example, between the patient positions depicted in FIGS. 1 and 5. This allows for a variable axis of rotation between the first portion 40 and the second portion 42.

Figure 6:
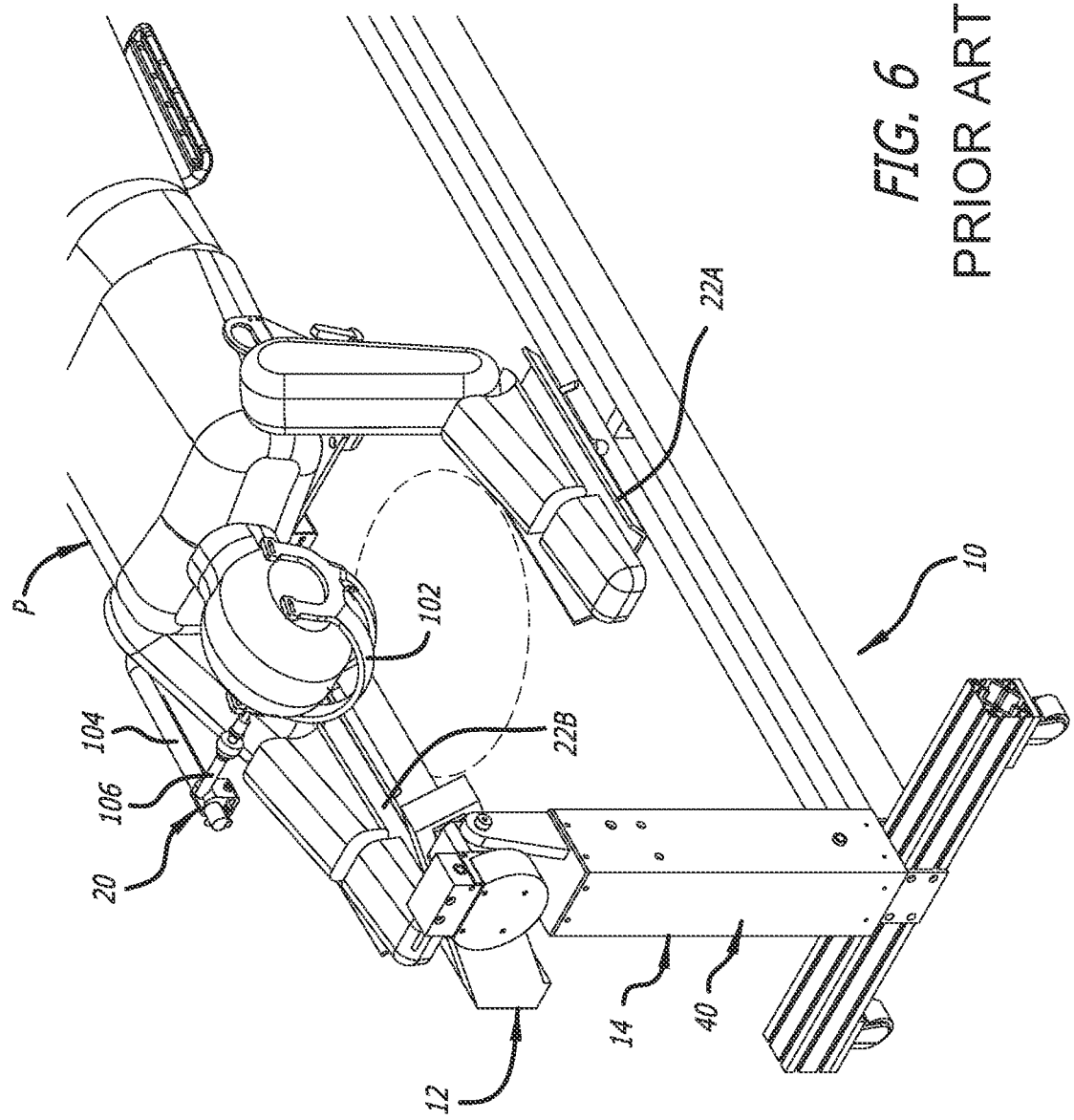
FIG. 6 is a top perspective view that illustrates portions of the surgical frame of FIG. 1 showing an area of access to the head of the patient positioned thereon in a prone position.

As depicted in FIG. 5, for example, the head support 20 is attached to a chest support plate 100 of the torso-lift support 24 to support the head of the patient P. If the torso-lift support 24 is not used, the head support 20 can be directly attached to the forward portion 72 of the offset main beam 12. As depicted in FIGS. 4 and 6, for example, the head support 20 further includes a facial support cradle 102, an axially adjustable head support beam 104, and a temple support portion 106. Soft straps (not shown) can be used to secure the patient P to the head support 20. The facial support cradle 102 includes padding across the forehead and cheeks, and provides open access to the mouth of the patient P. The head support 20 also allows for imaging access to the cervical spine. Adjustment of the head support 20 is possible via adjusting the angle and the length of the head support beam 104 and the temple support portion 106.

As depicted in FIG. 5, for example, the arm supports 22A and 22B contact the forearms and support the remainder of the arms of the patient P, with the first arm support 22A and the second arm support 22B attached to the chest support plate 100 of the torso-lift support 24. If the torso-lift support 24 is not used, the arm supports 22A and 22B can both be directly attached to the offset main beam 12. The arm supports 22A and 22B are positioned such that the arms of the patient P are spaced away from the remainder of the patient's body to provide access (FIG. 6) to at least portions of the face and neck of the patient P, thereby providing greater access to the patient.

Figure 7:
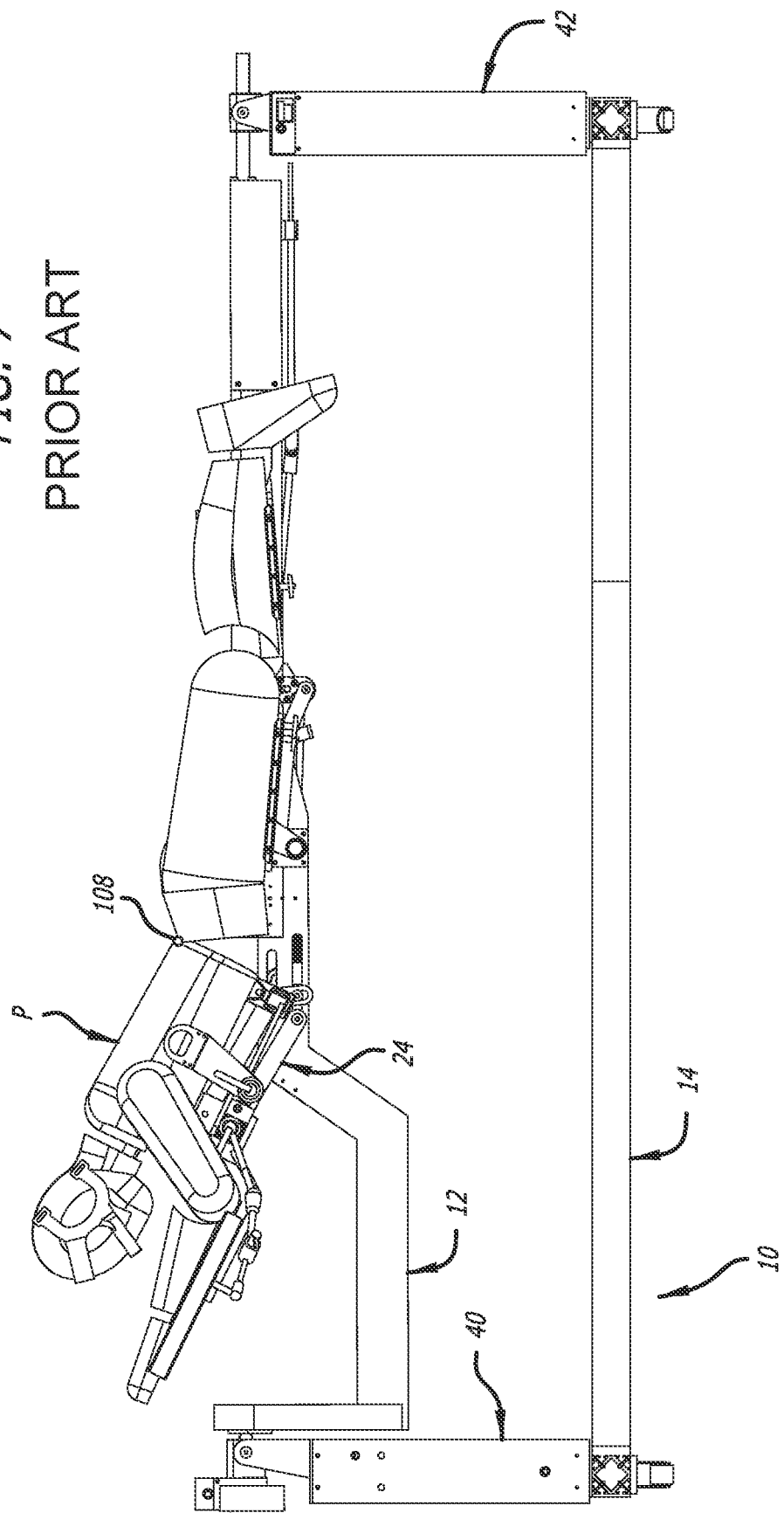
FIG. 7 is a side elevational view that illustrates the surgical frame of FIG. 1 showing a torso-lift support supporting the patient in a lifted position.
Figure 8:
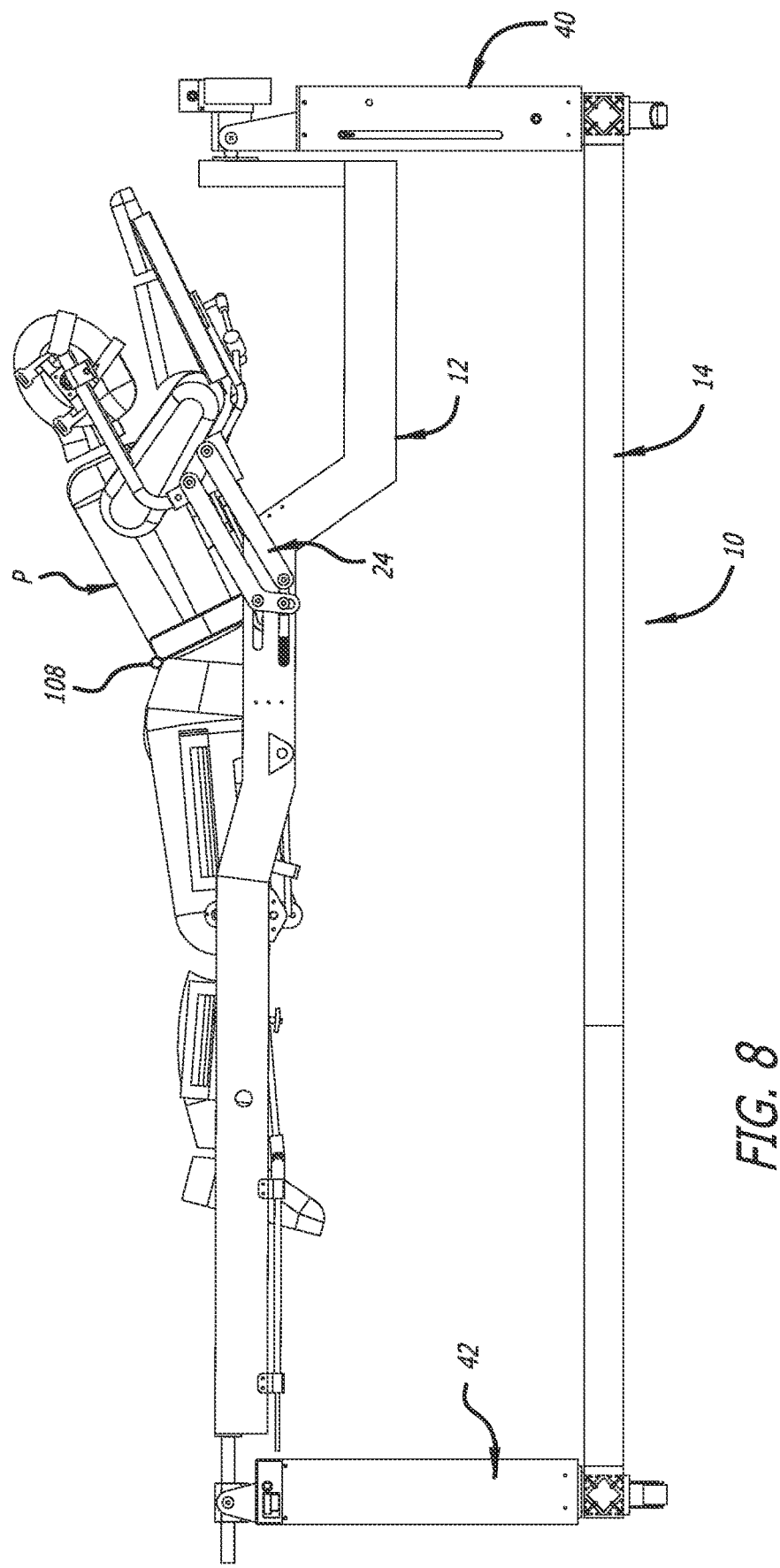
FIG. 8 is another side elevational view that illustrates the surgical frame of FIG. 1 showing the torso-lift support supporting the patient in the lifted position.
Figure 9:
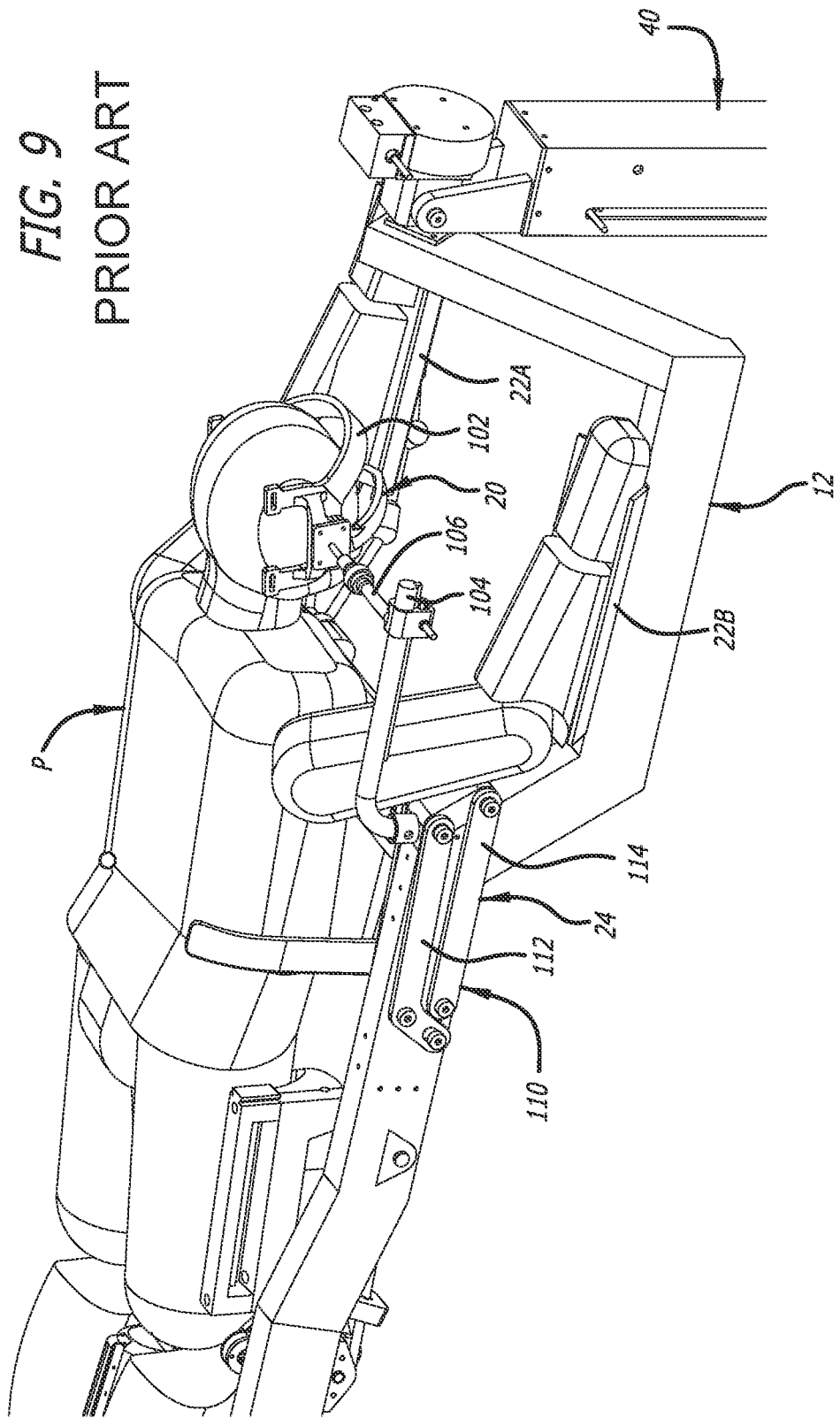
FIG. 9 is an enlarged top perspective view that illustrates portions of the surgical frame of FIG. 1 showing the torso-lift support supporting the patient in an unlifted position.

As depicted in FIGS. 7-12, for example, the surgical frame 10 includes a torso-lift capability for lifting and lowering the torso of the patient P between an uplifted position and a lifted position, which is described in detail below with respect to the torso-lift support 24. As depicted in FIGS. 7 and 8, for example, the torso-lift capability has an approximate center of rotation ("COR") 108 that is located at a position anterior to the patient's spine about the L2 of the lumbar spine, and is capable of elevating the upper body of the patient at least an additional six inches when measured at the chest support plate 100.

As depicted in FIGS. 9-12, for example, the torso-lift support 24 includes a "crawling" four-bar mechanism 110 attached to the chest support plate 100. Soft straps (not shown) can be used to secure the patient P to the chest support plate 100. The head support 20 and the arm supports 22A and 22B are attached to the chest support plate 100, thereby moving with the chest support plate 100 as the chest support plate 100 is articulated using the torso-lift support 24. The fixed COR 108 is defined at the position depicted in FIGS. 7 and 8. Appropriate placement of the COR 108 is important so that spinal cord integrity is not compromised (i.e., overly compressed or stretched) during the lift maneuver performed by the torso-lift support 24.

Figure 10:
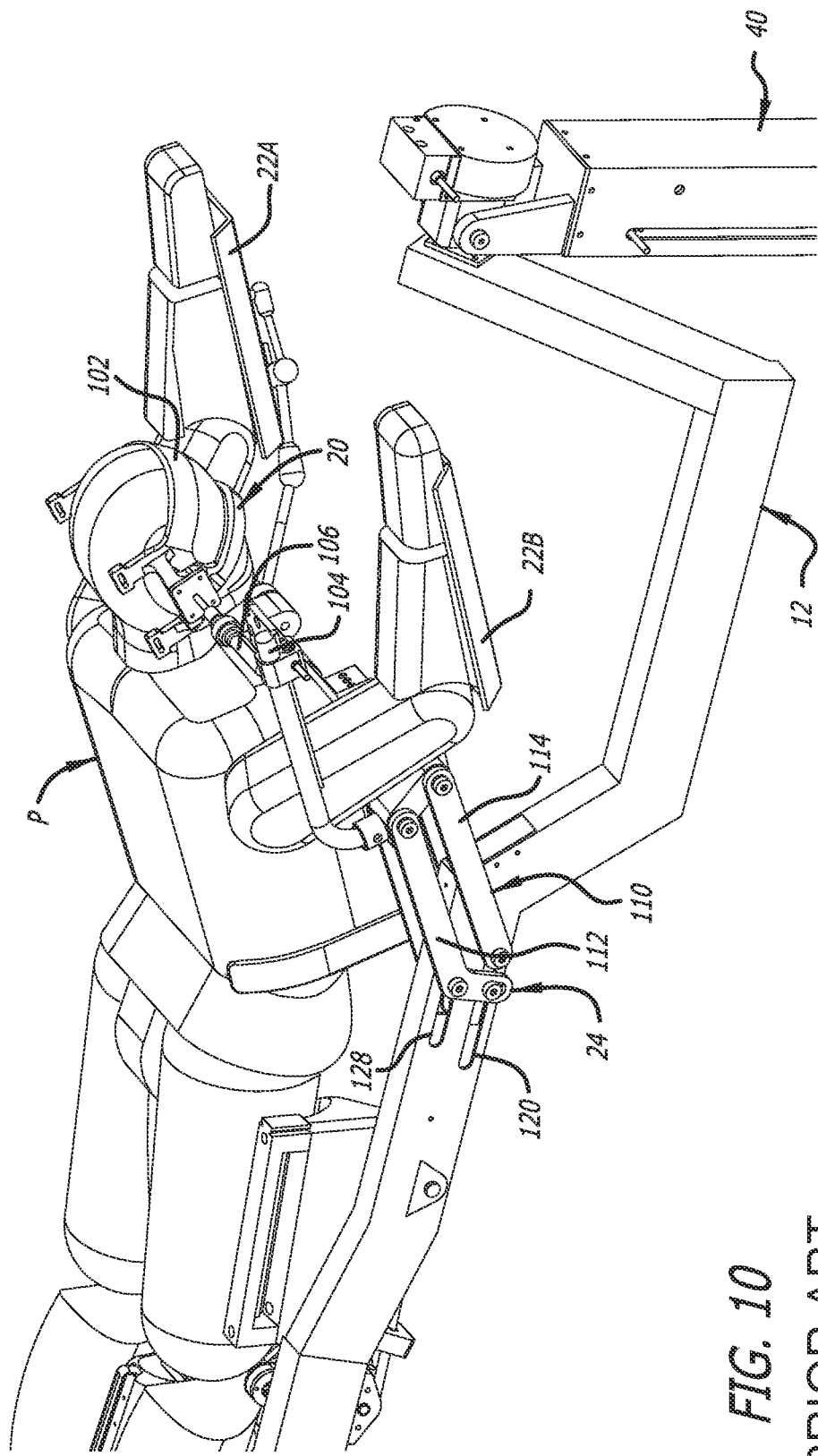
FIG. 10 is an enlarged top perspective view that illustrates portions of the surgical frame of FIG. 1 showing the torso-lift support supporting the patient in the lifted position.
Figure 11:
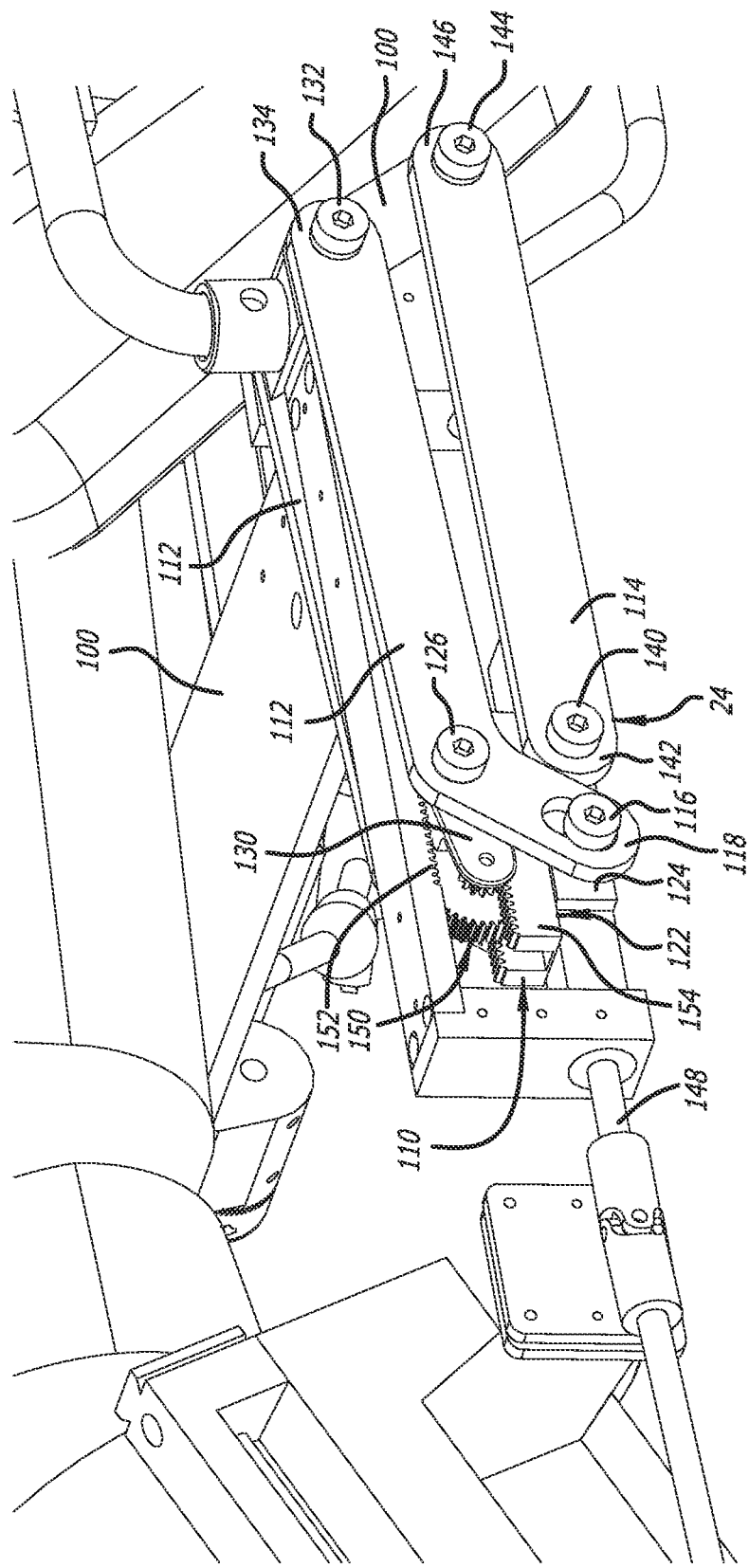
FIG. 11 is an enlarged top perspective view that illustrates componentry of the torso-lift support in the unlifted position.
Figure 12:
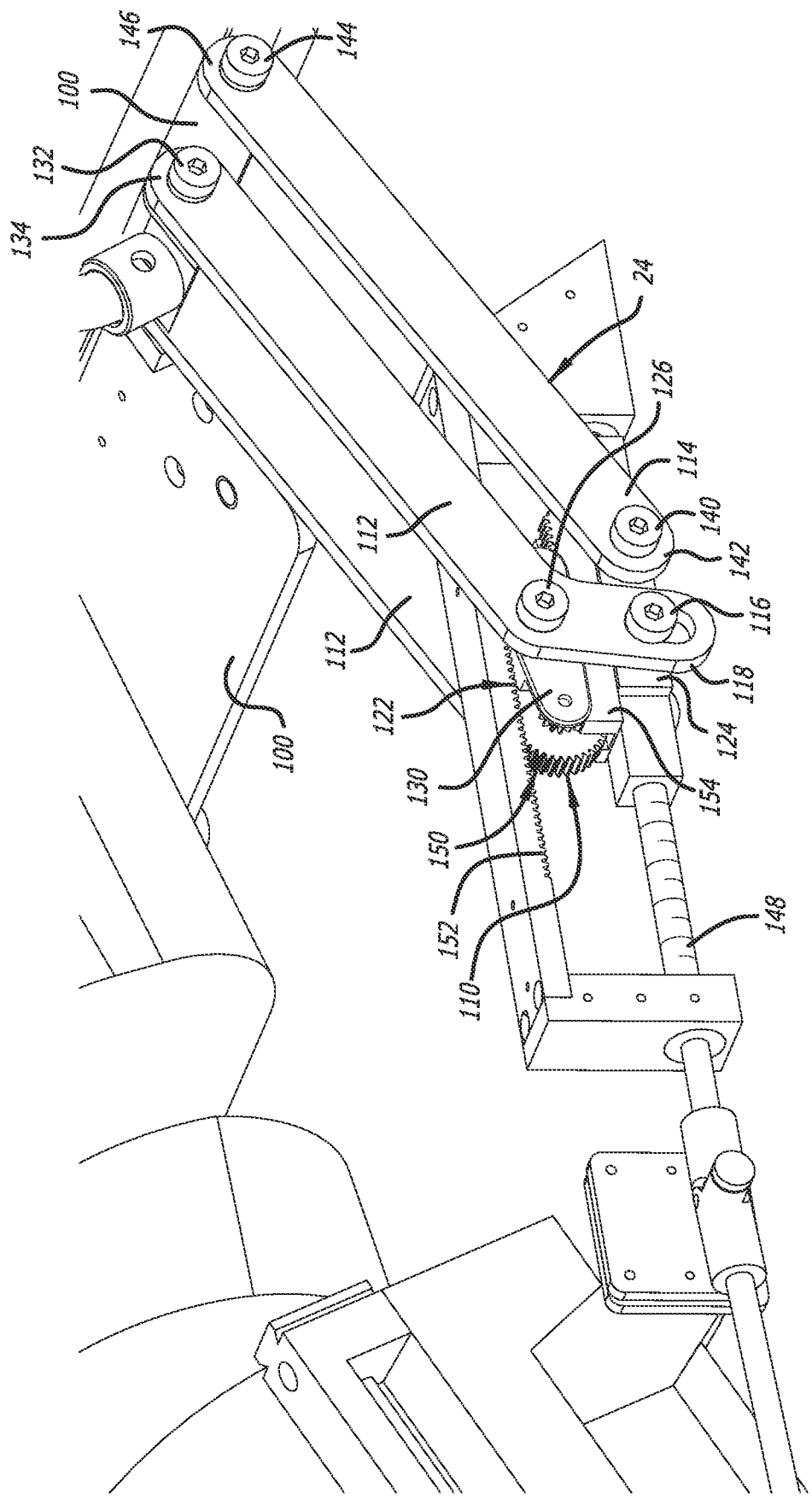
FIG. 12 is an enlarged top perspective view that illustrates the componentry of the torso-lift support in the lifted position.

As depicted in FIGS. 10-12, for example, the four-bar mechanism 110 includes first links 112 pivotally connected between offset main beam 12 and the chest support plate 100, and second links 114 pivotally connected between the offset main beam 12 and the chest support plate 100. As depicted in FIGS. 11 and 12, for example, in order to maintain the COR 108 at the desired fixed position, the first and second links 112 and 114 of the four-bar mechanism 110 crawl toward the first support portion 40 of the support structure 14, when the patient's upper body is being lifted. The first and second links 112 and 114 are arranged such that neither the surgeon's workspace nor imaging access are compromised while the patient's torso is being lifted.

As depicted in FIGS. 11 and 12, for example, each of the first links 112 define an L-shape, and includes a first pin 116 at a first end 118 thereof. The first pin 116 extends through first elongated slots 120 defined in the offset main beam 12, and the first pin 116 connects the first links 112 to a dual rack and pinion mechanism 122 via a drive nut 124 provided within the offset main beam 12, thus defining a lower pivot point thereof. Each of the first links 112 also includes a second pin 126 positioned proximate the corner of the L-shape. The second pin 126 extends through second elongated slots 128 defined in the offset main beam 12, and is linked to a carriage 130 of rack and pinion mechanism 122. Each of the first links 112 also includes a third pin 132 at a second end 134 that is pivotally attached to chest support plate 100, thus defining an upper pivot point thereof.

As depicted in FIGS. 11 and 12, for example, each of the second links 114 includes a first pin 140 at a first end 142 thereof. The first pin 140 extends through the first elongated slot 120 defined in the offset main beam 12, and the first pin 140 connects the second links 114 to the drive nut 124 of the rack and pinion mechanism 122, thus defining a lower pivot point thereof. Each of the second links 114 also includes a second pin 144 at a second end 146 that is pivotally connected to the chest support plate 100, thus defining an upper pivot point thereof.

As depicted in FIGS. 11 and 12, the rack and pinion mechanism 122 includes a drive screw 148 engaging the drive nut 124. Coupled gears 150 are attached to the carriage 130. The larger of the gears 150 engage an upper rack 152 (fixed within the offset main beam 12), and the smaller of the gears 150 engage a lower rack 154. The carriage 130 is defined as a gear assembly that floats between the two racks 152 and 154.

As depicted in FIGS. 11 and 12, the rack and pinion mechanism 122 converts rotation of the drive screw 148 into linear translation of the first and second links 112 and 114 in the first and second elongated slots 120 and 128 toward the first portion 40 of the support structure 14. As the drive nut 124 translates along drive screw 148 (via rotation of the drive screw 148), the carriage 130 translates towards the first portion 40 with less travel due to the different gear sizes of the coupled gears 150. The difference in travel, influenced by different gear ratios, causes the first links 112 pivotally attached thereto to lift the chest support plate 100. Lowering of the chest support plate 100 is accomplished by performing this operation in reverse. The second links 114 are "idler" links (attached to the drive nut 124 and the chest support plate 100) that controls the tilt of the chest support plate 100 as it is being lifted and lowered. All components associated with lifting while tilting the chest plate predetermine where COR 108 resides. Furthermore, a servomotor (not shown) interconnected with the drive screw 148 can be computer controlled and/or operated by the operator of the surgical frame 10 to facilitate controlled lifting and lowering of the chest support plate 100. A safety feature can be provided, enabling the operator to read and limit a lifting and lowering force applied by the torso-lift support 24 in order to prevent injury to the patient P. Moreover, the torso-lift support 24 can also include safety stops (not shown) to prevent over-extension or compression of the patient P, and sensors (not shown) programmed to send patient position feedback to the safety stops.

Figure 13A:
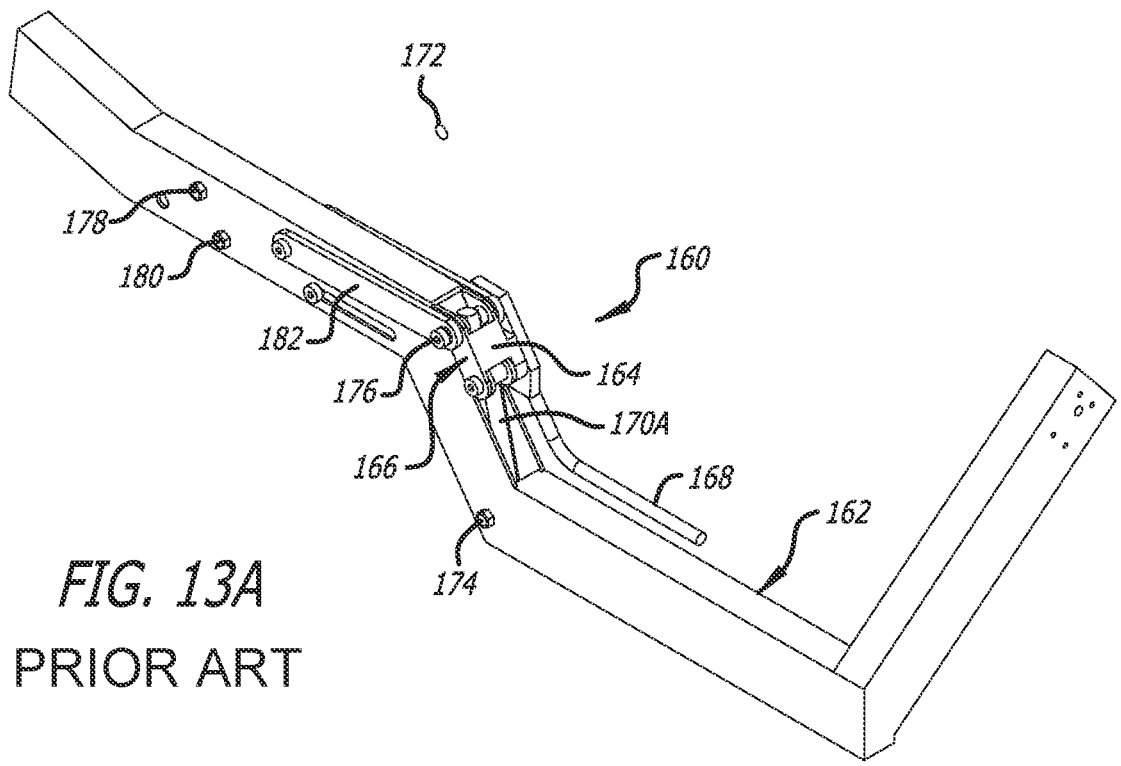
FIG. 13A is a perspective view of an embodiment that illustrates a structural offset main beam for use with another embodiment of a torso-lift support showing the torso-lift support in a retracted position.

An alternative preferred embodiment of a torso-lift support is generally indicated by the numeral 160 in FIGS. 13A-15. As depicted in FIGS. 13A-13C, an alternate offset main beam 162 is utilized with the torso-lift support 160. Furthermore, the torso-lift support 160 has a support plate 164 pivotally linked to the offset main beam 162 by a chest support lift mechanism 166. An arm support rod/plate 168 is connected to the support plate 164, and the second arm support 22B. The support plate 164 is attached to the chest support plate 100, and the chest support lift mechanism 166 includes various actuators 170A, 170B, and 170C used to facilitate positioning and repositioning of the support plate 164 (and hence, the chest support plate 100).

Figure 13B:
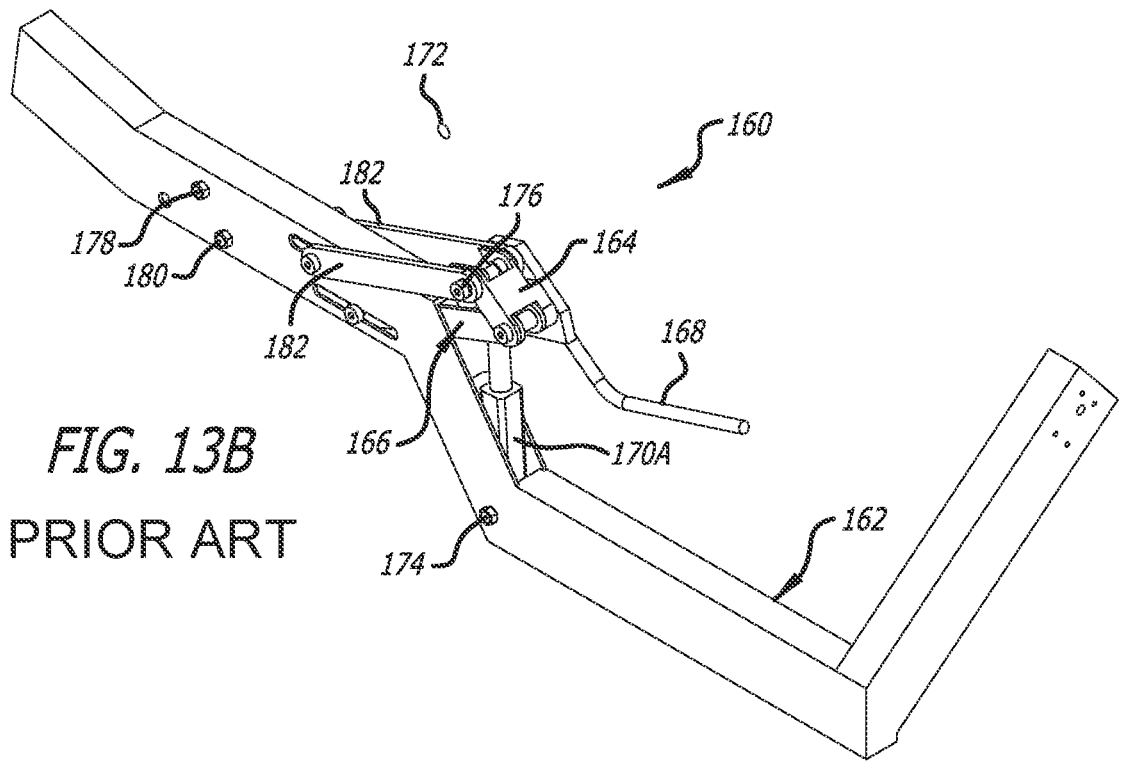
FIG. 13B is a perspective view similar to FIG. 13A showing the torso-lift support at half travel.
Figure 13C:
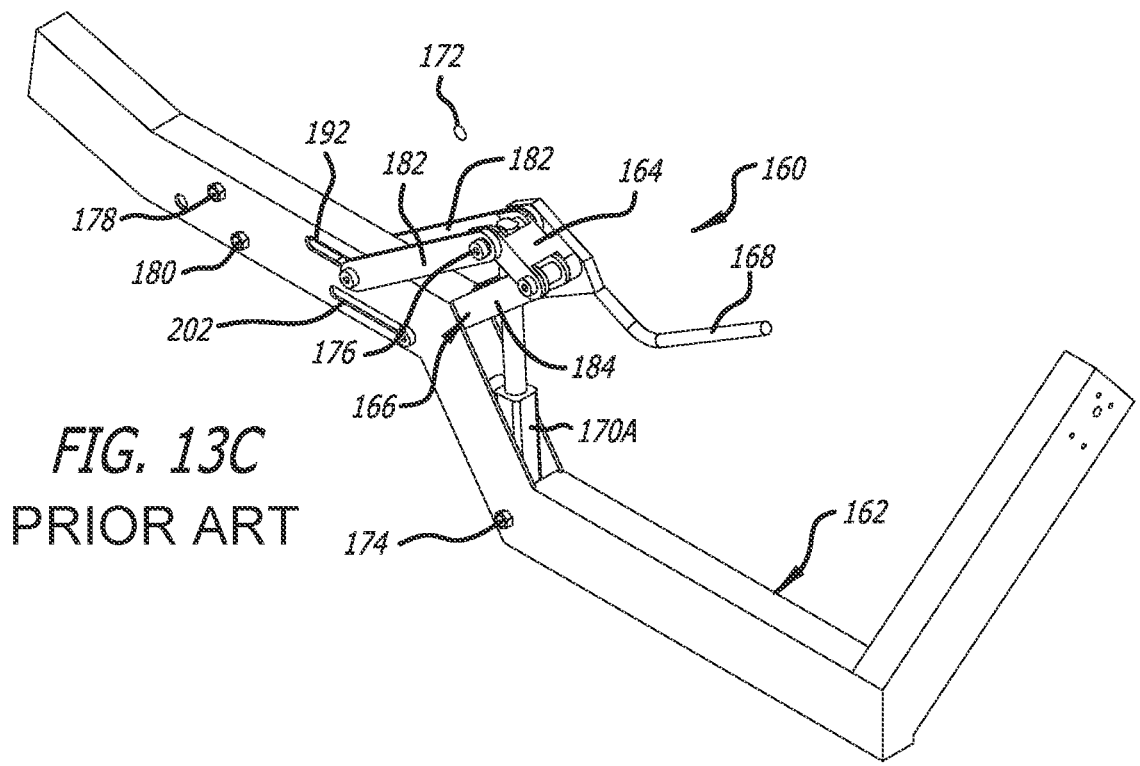
FIG. 13C is a perspective view similar to FIGS. 13A and 13B showing the torso-lift support at full travel.

As discussed below, the torso-lift support 160 depicted in FIGS. 13A-15 enables a COR 172 thereof to be programmably altered such that the COR 172 can be a fixed COR or a variable COR. As their names suggest, the fixed COR stays in the same position as the torso-lift support 160 is actuated, and the variable COR moves between a first position and a second position as the torso-lift support 160 is actuated between its initial position and final position at full travel thereof. Appropriate placement of the COR 172 is important so that spinal cord integrity is not compromised (i.e., overly compressed or stretched). Thus, the support plate 164 (and hence, the chest support plate 100) follows a path coinciding with a predetermined COR 172 (either fixed or variable). FIG. 13A depicts the torso-lift support 160 retracted, FIG. 13B depicts the torso-lift support 160 at half travel, and FIG. 13C depicts the torso-lift support 160 at full travel.

Figure 14:
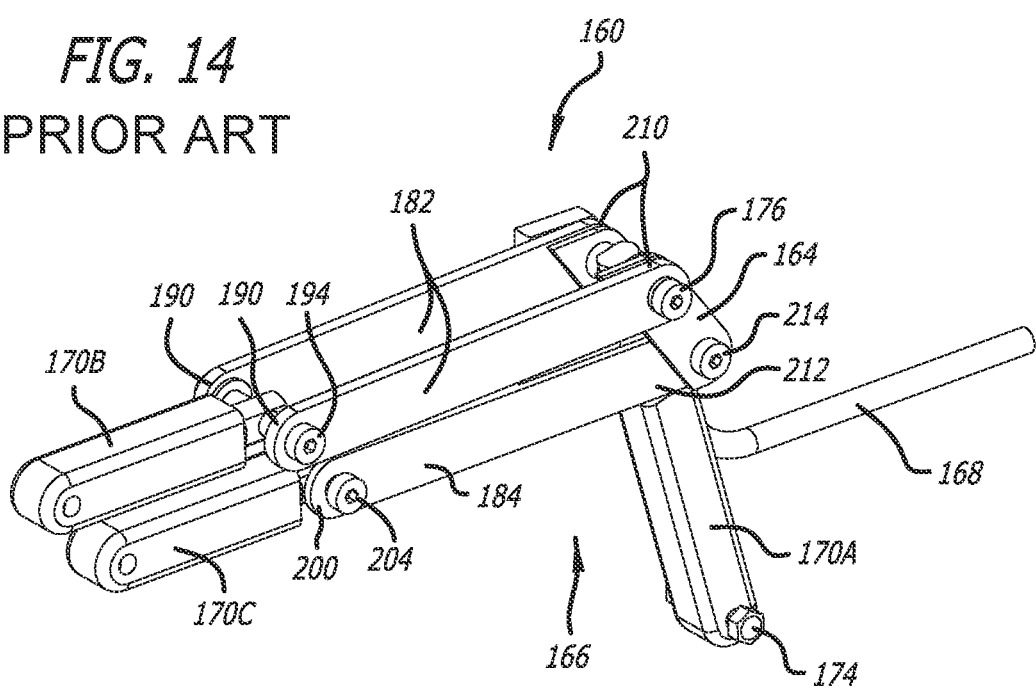
FIG. 14 is a perspective view that illustrates a chest support lift mechanism of the torso-lift support of FIGS. 13A-13C with actuators thereof retracted.
Figure 15:
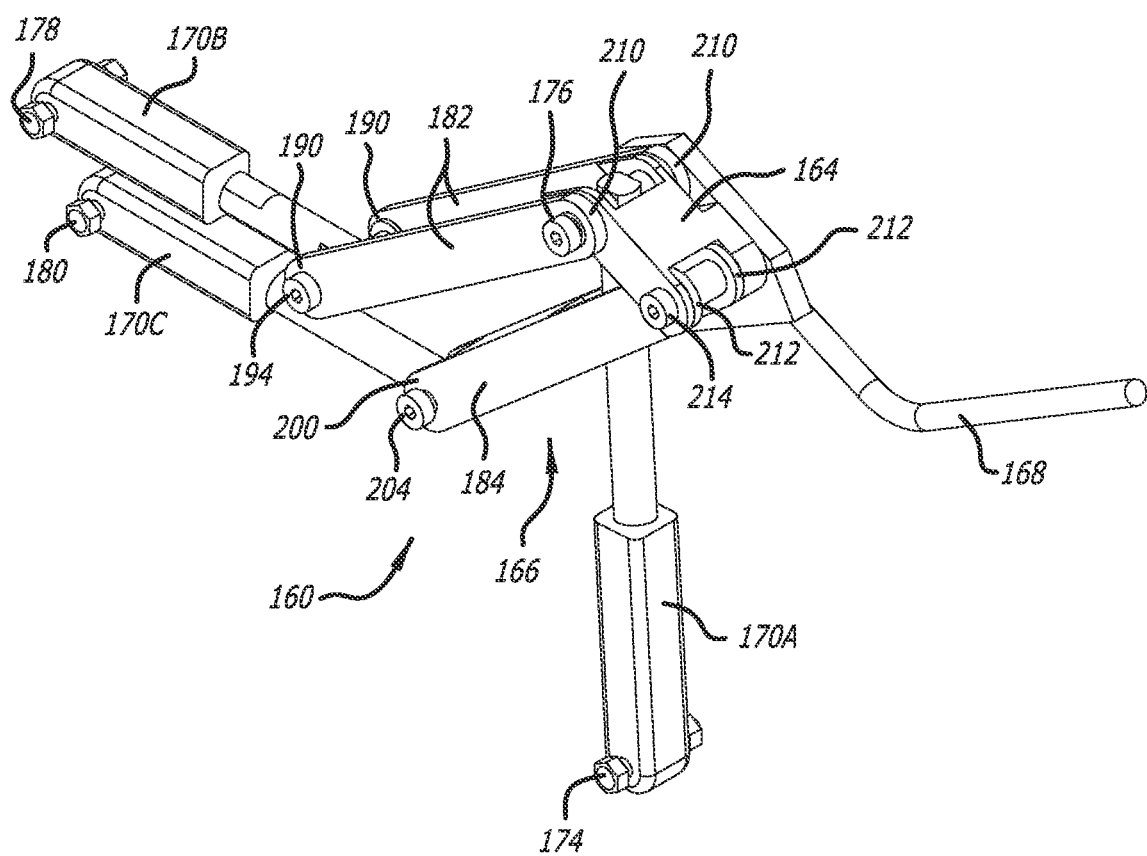
FIG. 15 is another perspective view that illustrates a chest support lift mechanism of the torso-lift support of FIGS. 13A-13C with the actuators thereof extended.

As discussed above, the chest support lift mechanism 166 includes the actuators 170A, 170B, and 170C to position and reposition the support plate 164 (and hence, the chest support plate 100). As depicted in FIGS. 14 and 15, for example, the first actuator 170A, the second actuator 1706, and the third actuator 170C are provided. Each of the actuators 170A, 170B, and 170C are interconnected with the offset main beam 12 and the support plate 164, and each of the actuators 170A, 170B, and 170C are moveable between a retracted and extended position. As depicted in FIGS. 13A-13C, the first actuator 170A is pinned to the offset main beam 162 using a pin 174 and pinned to the support plate 164 using a pin 176. Furthermore, the second and third actuators 170B and 170C are received within the offset main beam 162. The second actuator 170B is interconnected with the offset main beam 162 using a pin 178, and the third actuator 170C is interconnected with the offset main beam 162 using a pin 180.

The second actuator 170B is interconnected with the support plate 164 via first links 182, and the third actuator 170C is interconnected with the support plate 164 via second links 184. First ends 190 of the first links 182 are pinned to the second actuator 170B and elongated slots 192 formed in the offset main beam 162 using a pin 194, and first ends 200 of the second links 184 are pinned to the third actuator 170C and elongated slots 202 formed in the offset main beam 162 using a pin 204. The pins 194 and 204 are moveable within the elongated slots 192 and 202. Furthermore, second ends 210 of the first links 182 are pinned to the support plate 164 using the pin 176, and second ends 212 of the second links 184 are pinned to the support plate 164 using a pin 214. To limit interference therebetween, as depicted in FIGS. 13A-13C, the first links 182 are provided on the exterior of the offset main beam 162, and, depending on the position thereof, the second links 184 are positioned on the interior of the offset main beam 162.

Actuation of the actuators 170A, 170B, and 170C facilitates movement of the support plate 164. Furthermore, the amount of actuation of the actuators 170A, 170B, and 170C can be varied to affect different positions of the support plate 164. As such, by varying the amount of actuation of the actuators 170A, 170B, and 170C, the COR 172 thereof can be controlled. As discussed above, the COR 172 can be predetermined, and can be either fixed or varied. Furthermore, the actuation of the actuators 170A, 170B, and 170C can be computer controlled and/or operated by the operator of the surgical frame 10, such that the COR 172 can be programmed by the operator. As such, an algorithm can be used to determine the rates of extension of the actuators 170A, 170B, and 170C to control the COR 172, and the computer controls can handle implementation of the algorithm to provide the predetermined COR. A safety feature can be provided, enabling the operator to read and limit a lifting force applied by the actuators 170A, 170B, and 170C in order to prevent injury to the patient P. Moreover, the torso-lift support 160 can also include safety stops (not shown) to prevent over-extension or compression of the patient P, and sensors (not shown) programmed to send patient position feedback to the safety stops.

FIGS. 16-23 depict portions of the sagittal adjustment assembly 28. The sagittal adjustment assembly 28 can be used to distract or compress the patient's lumbar spine during or after lifting or lowering of the patient's torso by the torso-lift supports. The sagittal adjustment assembly 28 supports and manipulates the lower portion of the patient's body. In doing so, the sagittal adjustment assembly 28 is configured to make adjustments in the sagittal plane of the patient's body, including tilting the pelvis, controlling the position of the upper and lower legs, and lordosing the lumbar spine.

Figure 16:
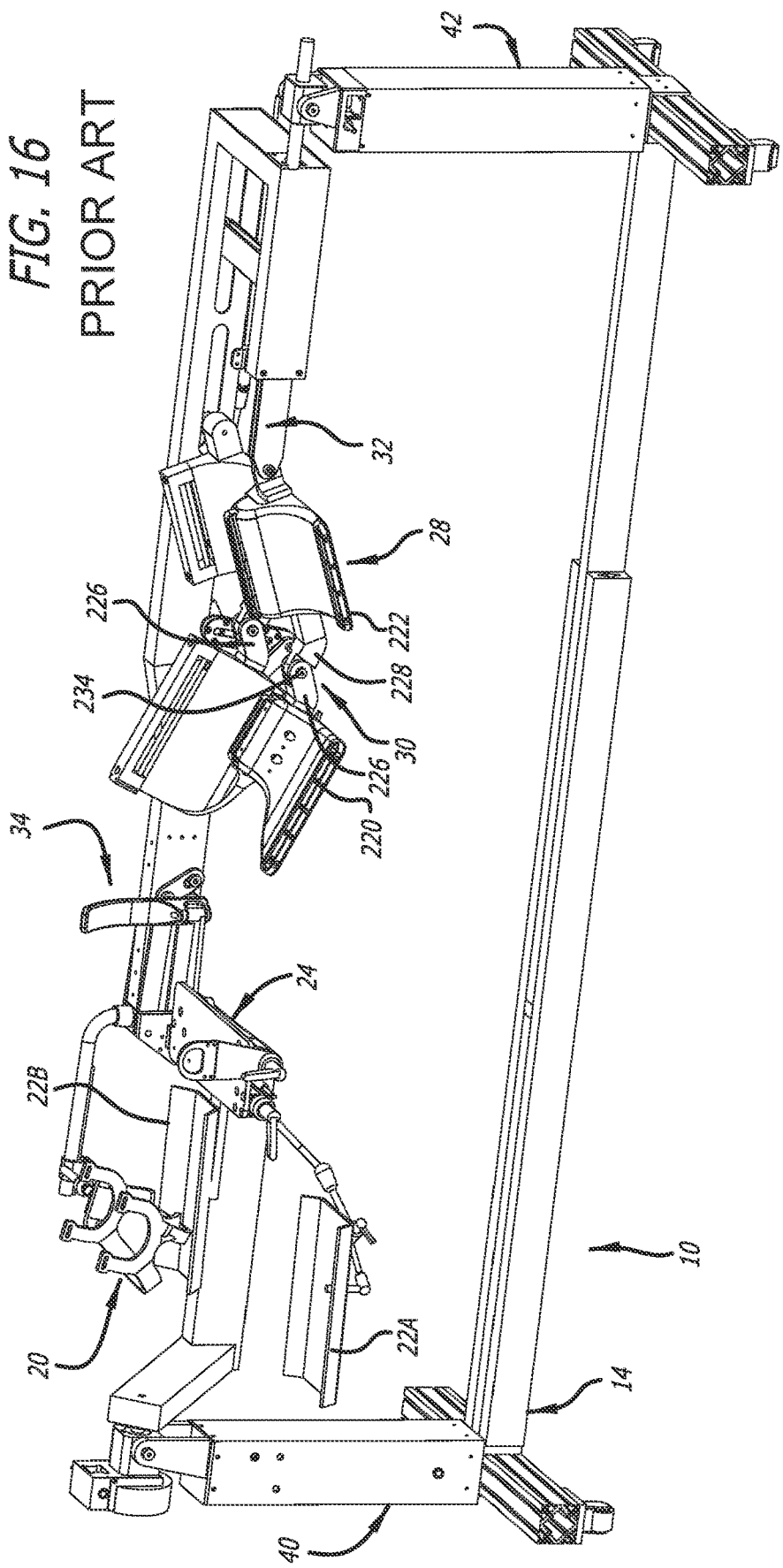
FIG. 16 is a top perspective view that illustrates the surgical frame of FIG. 1.
Figure 17:
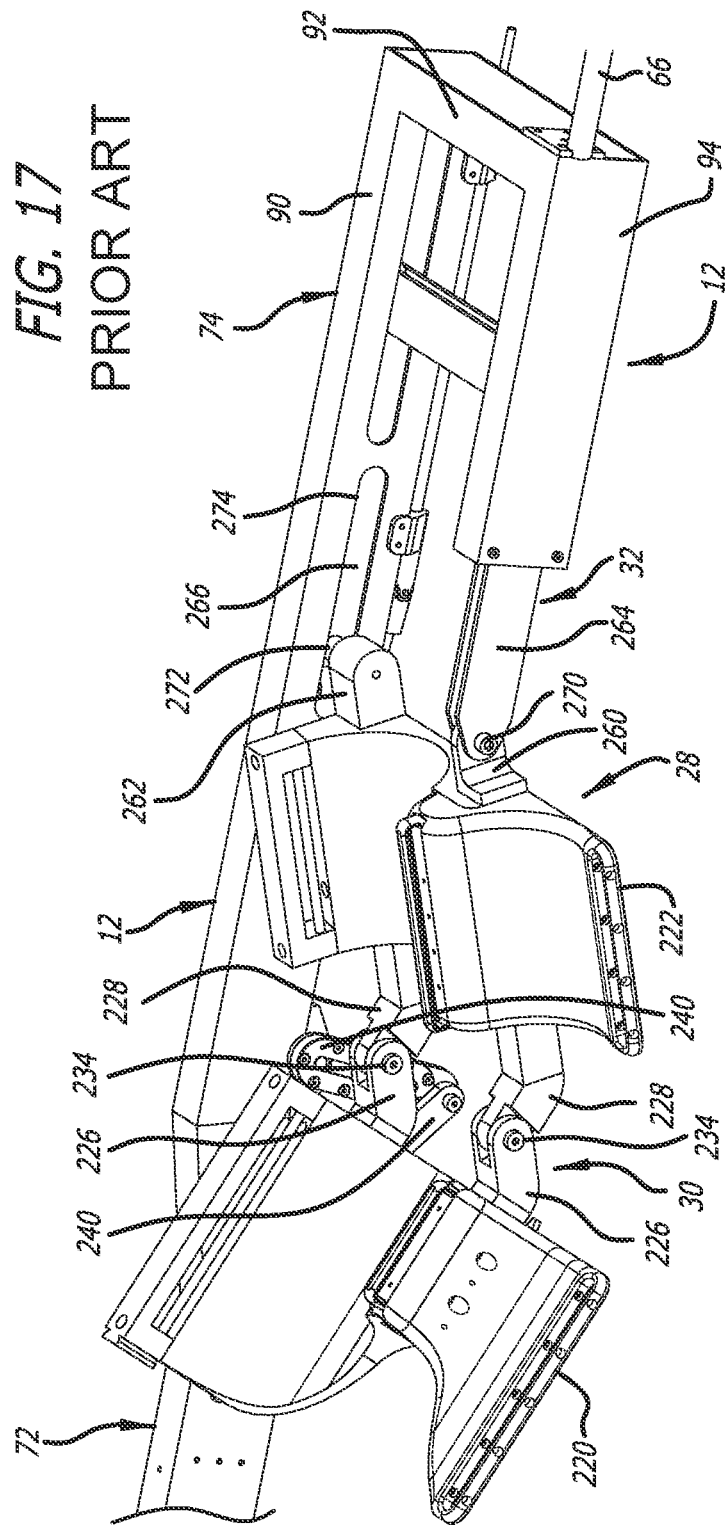
FIG. 17 is an enlarged top perspective view that illustrates portions of the surgical frame of FIG. 1 showing a sagittal adjustment assembly including a pelvic-tilt mechanism and leg adjustment mechanism.

As depicted in FIGS. 16 and 17, for example, the sagittal adjustment assembly 28 includes the pelvic-tilt mechanism 30 for supporting the thighs and lower legs of the patient P. The pelvic-tilt mechanism 30 includes a thigh cradle 220 configured to support the patient's thighs, and a lower leg cradle 222 configured to support the patient's shins. Different sizes of thigh and lower leg cradles can be used to accommodate different sizes of patients, i.e., smaller thigh and lower leg cradles can be used with smaller patients, and larger thigh and lower leg cradles can be used with larger patients. Soft straps (not shown) can be used to secure the patient P to the thigh cradle 220 and the lower leg cradle 222. The thigh cradle 220 and the lower leg cradle 222 are moveable and pivotal with respect to one another and to the offset main beam 12. To facilitate rotation of the patient's hips, the thigh cradle 220 and the lower leg cradle 222 can be positioned anterior and inferior to the patient's hips.

Figure 18:
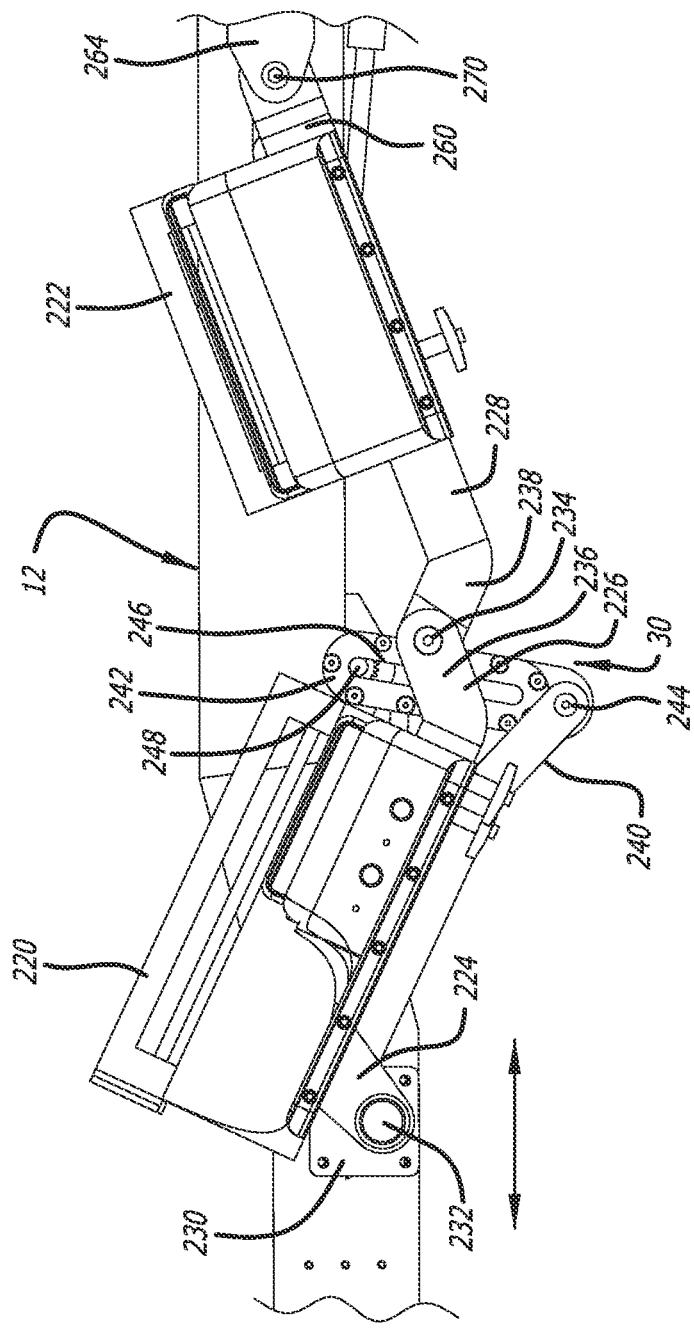
FIG. 18 is an enlarged side elevational view that illustrates portions of the surgical frame of FIG. 1 showing the pelvic-tilt mechanism.
Figure 25:
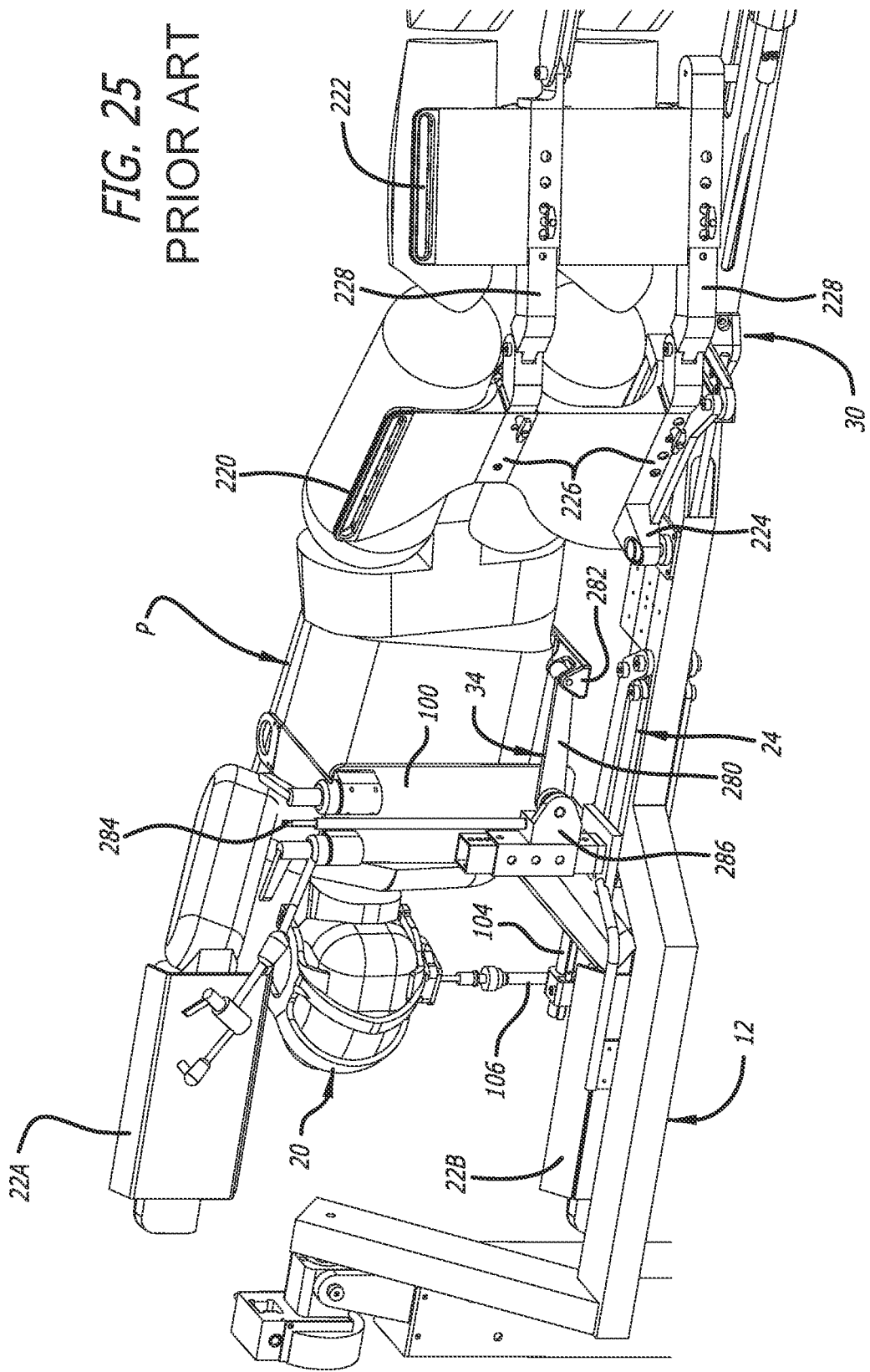
FIG. 25 is a top perspective view that illustrates portions of the surgical frame of FIG. 1 showing operation of the coronal adjustment assembly.

As depicted in FIGS. 18 and 25, for example, a first support strut 224 and second support struts 226 are attached to the thigh cradle 220. Furthermore, third support struts 228 are attached to the lower leg cradle 222. The first support strut 224 is pivotally attached to the offset main beam 12 via a support plate 230 and a pin 232, and the second support struts 226 are pivotally attached to the third support struts 228 via pins 234. The pins 234 extend through angled end portions 236 and 238 of the second and third support struts 226 and 228, respectively. Furthermore, the lengths of second and third support struts 226 and 228 are adjustable to facilitate expansion and contraction of the lengths thereof.

To accommodate patients with different torso lengths, the position of the thigh cradle 220 can be adjustable by moving the support plate 230 along the offset main beam 12. Furthermore, to accommodate patients with different thigh and lower leg lengths, the lengths of the second and third support struts 226 and 228 can be adjusted.

Figure 19:
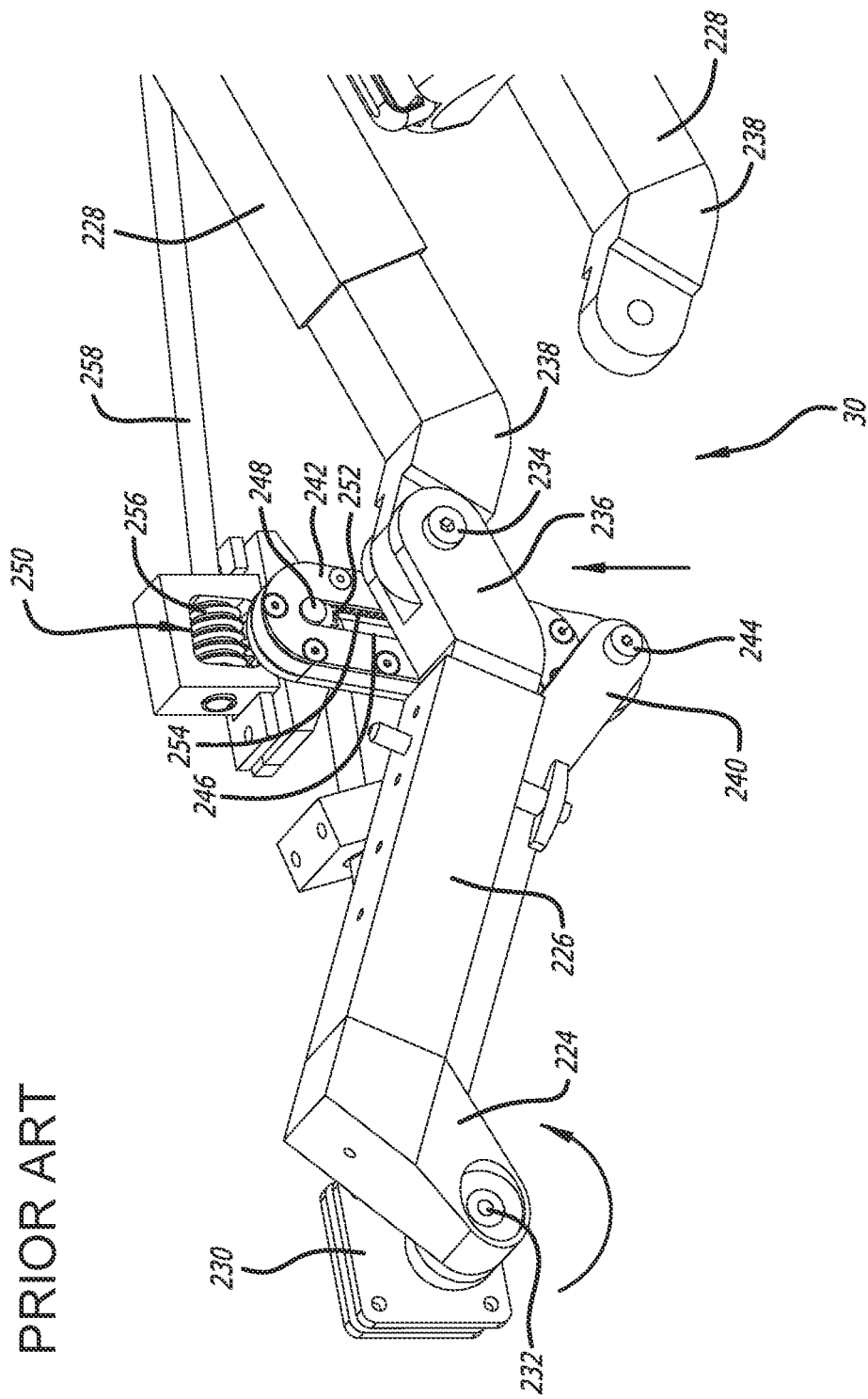
FIG. 19 is an enlarged perspective view that illustrates componentry of the pelvic-tilt mechanism.
Figure 20:
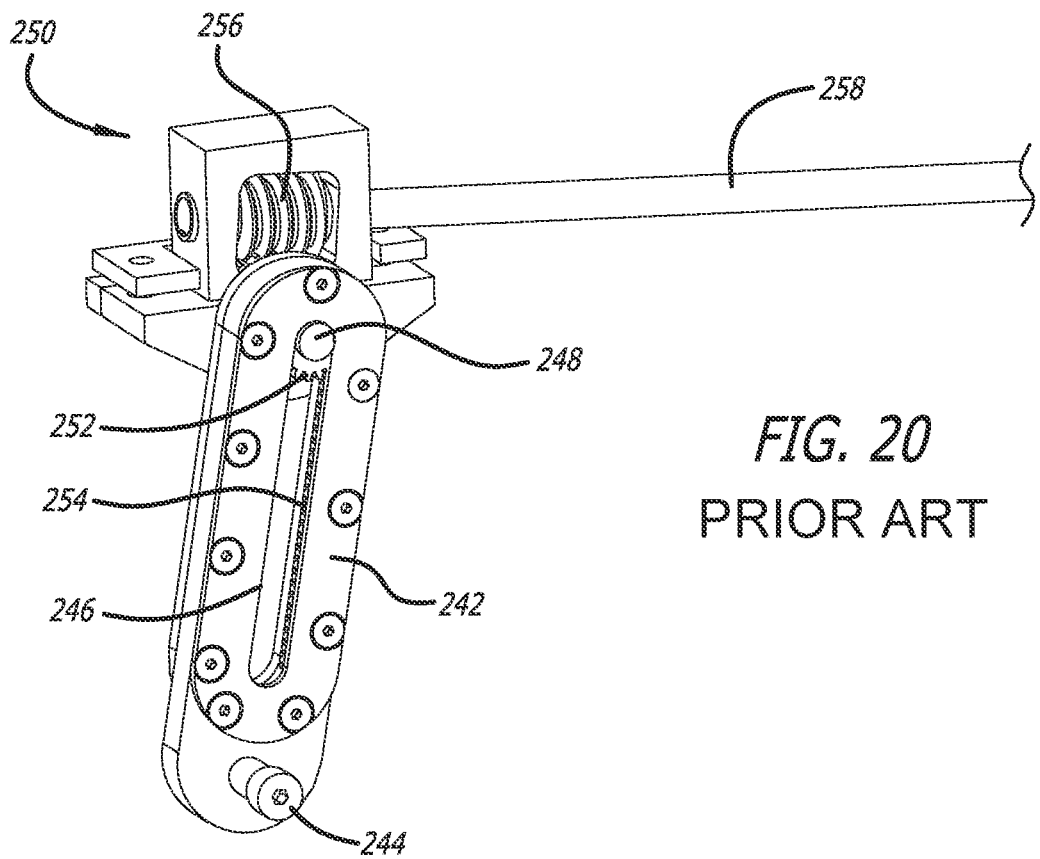
FIG. 20 is an enlarged perspective view that illustrates a captured rack and a worm gear assembly of the componentry of the pelvic-tilt mechanism.
Figure 21:
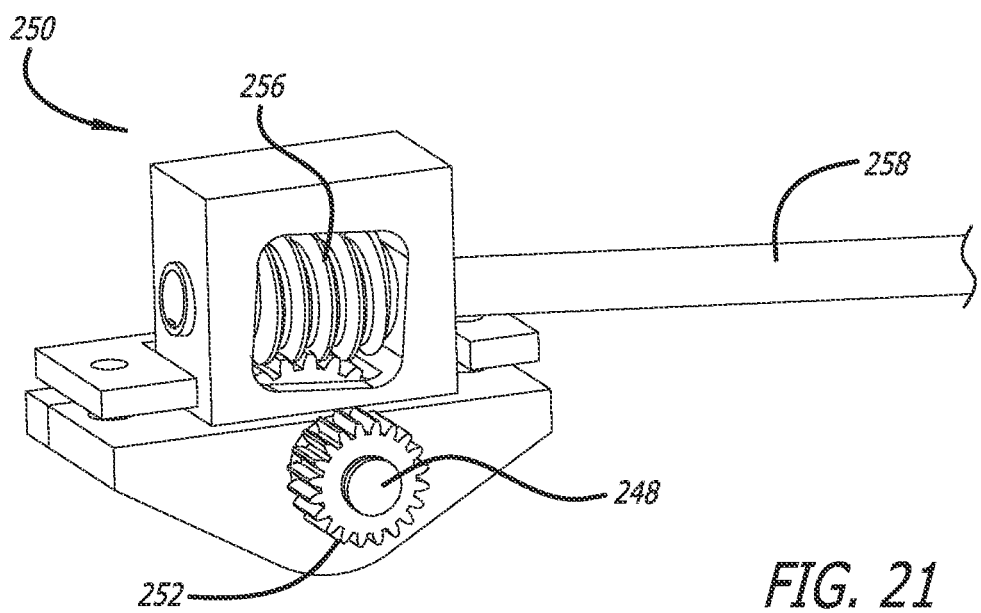
FIG. 21 is an enlarged perspective view that illustrates the worm gear assembly of FIG. 20.

To control the pivotal angle between the second and third support struts 226 and 228 (and hence, the pivotal angle between the thigh cradle 220 and lower leg cradle 222), a link 240 is pivotally connected to a captured rack 242 via a pin 244. The captured rack 242 includes an elongated slot 246, through which is inserted a worm gear shaft 248 of a worm gear assembly 250. The worm gear shaft 248 is attached to a gear 252 provided on the interior of the captured rack 242. The gear 252 contacts teeth 254 provided inside the captured rack 242, and rotation of the gear 252 (via contact with the teeth 254) causes motion of the captured rack 242 upwardly and downwardly. The worm gear assembly 250, as depicted in FIGS. 19-21, for example, includes worm gears 256 which engage a drive shaft 258, and which are connected to the worm gear shaft 248.

The worm gear assembly 250 also is configured to function as a brake, which prevents unintentional movement of the sagittal adjustment assembly 28. Rotation of the drive shaft 258 causes rotation of the worm gears 256, thereby causing reciprocal vertical motion of the captured rack 242. The vertical reciprocal motion of the captured rack 242 causes corresponding motion of the link 240, which in turn pivots the second and third support struts 226 and 228 to correspondingly pivot the thigh cradle 220 and lower leg cradle 222. A servomotor (not shown) interconnected with the drive shaft 258 can be computer controlled and/or operated by the operator of the surgical frame 10 to facilitate controlled reciprocal motion of the captured rack 242.

The sagittal adjustment assembly 28 also includes the leg adjustment mechanism 32 facilitating articulation of the thigh cradle 220 and the lower leg cradle 222 with respect to one another. In doing so, the leg adjustment mechanism 32 accommodates the lengthening and shortening of the patient's legs during bending thereof. As depicted in FIG. 17, for example, the leg adjustment mechanism 32 includes a first bracket 260 and a second bracket 262 attached to the lower leg cradle 222. The first bracket 260 is attached to a first carriage portion 264, and the second bracket 262 is attached to a second carriage portion 266 via pins 270 and 272, respectively. The first carriage portion 264 is slidable within third portion 94 of the rear portion 74 of the offset main beam 12, and the second carriage portion 266 is slidable within the first portion 90 of the rear portion 74 of the offset main beam 12. An elongated slot 274 is provided in the first portion 90 to facilitate engagement of the second bracket 262 and the second carriage portion 266 via the pin 272. As the thigh cradle 220 and the lower leg cradle 222 articulate with respect to one another (and the patient's legs bend accordingly), the first carriage 264 and the second carriage 266 can move accordingly to accommodate such movement.

Figure 22:
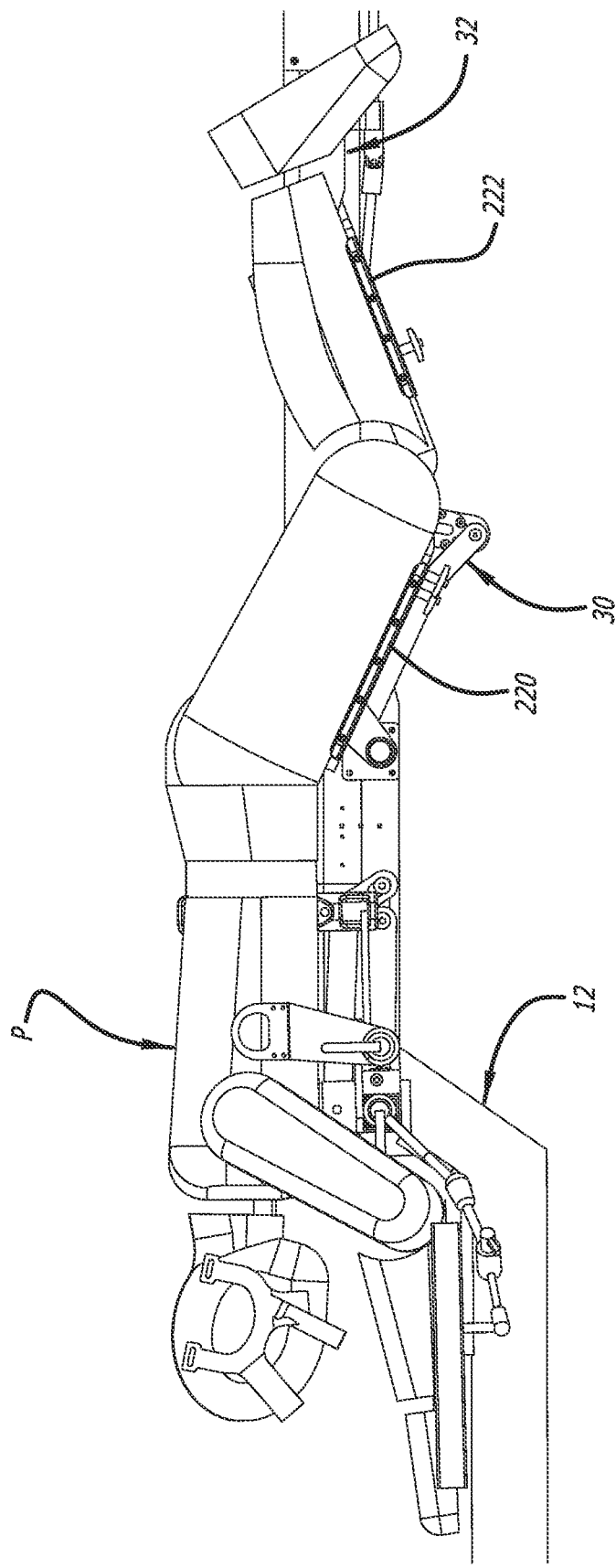
FIG. 22 is a side elevational view that illustrates portions of the surgical frame of FIG. 1 showing the patient positioned thereon and the pelvic-tilt mechanism of the sagittal adjustment assembly in the flexed position.
Figure 23:
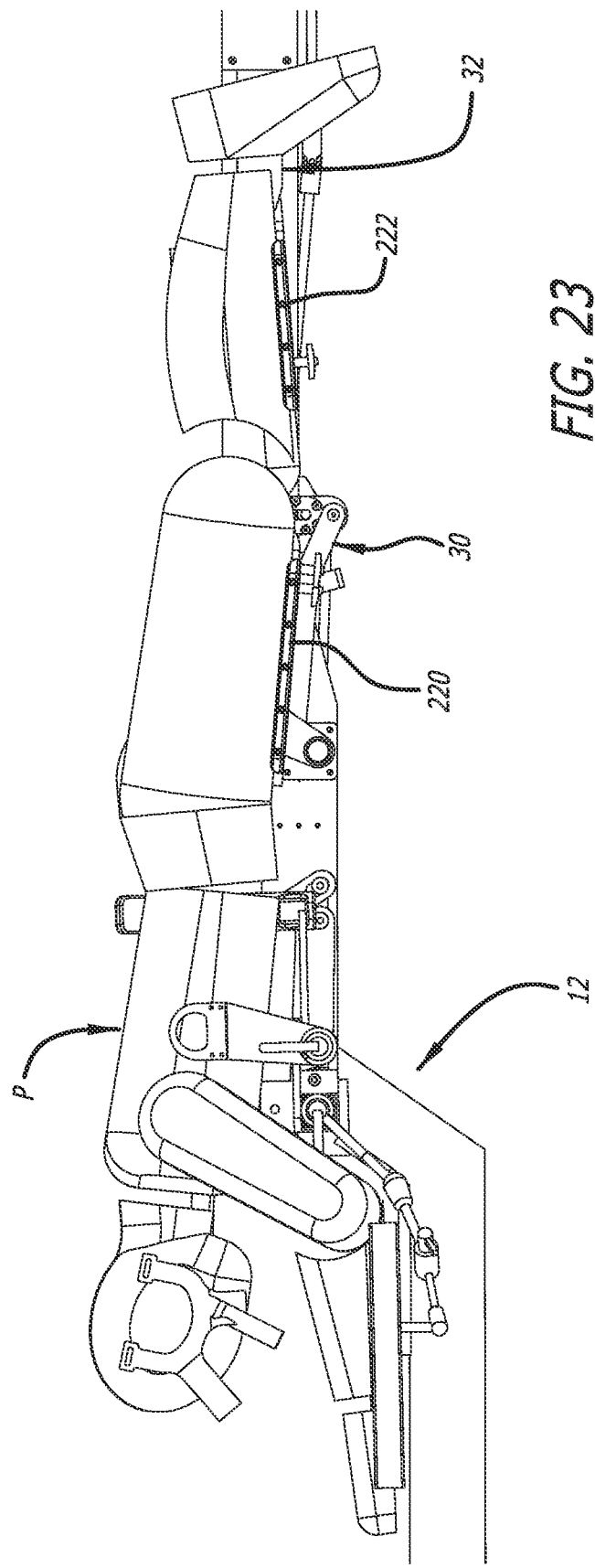
FIG. 23 is another side elevational view that illustrates portions of the surgical frame of FIG. 1 showing the patient positioned thereon and the pelvic-tilt mechanism of the sagittal adjustment assembly in the fully extended position.

The pelvic-tilt mechanism 30 is movable between a flexed position and a fully extended position. As depicted in FIG. 22, in the flexed position, the lumbar spine is hypo-lordosed. This opens the posterior boundaries of the lumbar vertebral bodies and allows for easier placement of any interbody devices. The lumbar spine stretches slightly in this position. As depicted in FIG. 23, in the extended position, the lumbar spine is lordosed. This compresses the lumbar spine. When posterior fixation devices, such as rods and screws, are placed, optimal sagittal alignment can be achieved. During sagittal alignment, little to negligible angle change occurs between the thighs and the pelvis. The pelvic-tilt mechanism 30 also can hyper-extend the hips as a means of lordosing the spine, in addition to tilting the pelvis. One of ordinary skill will recognize, however, that straightening the patient's legs does not lordose the spine. Leg straightening is a consequence of rotating the pelvis while maintaining a fixed angle between the pelvis and the thighs.

The sagittal adjustment assembly 28, having the configuration described above, further includes an ability to compress and distract the spine dynamically while in the lordosed or flexed positions. The sagittal adjustment assembly 28 also includes safety stops (not shown) to prevent overextension or compression of the patient, and sensors (not shown) programmed to send patient position feedback to the safety stops.

Figure 24:
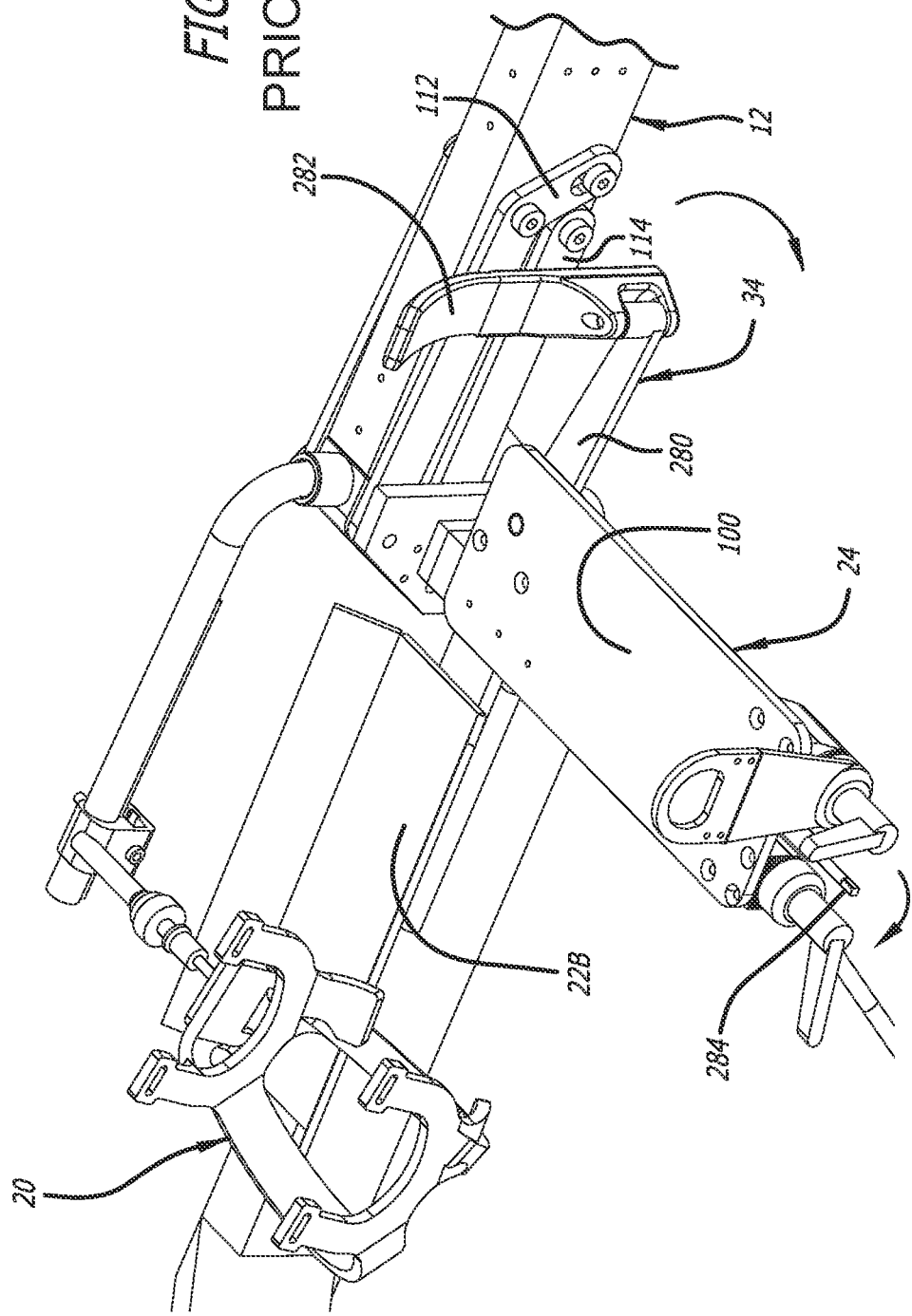
FIG. 24 is an enlarged top perspective view that illustrates portions of the surgical frame of FIG. 1 showing a coronal adjustment assembly.
Figure 26:
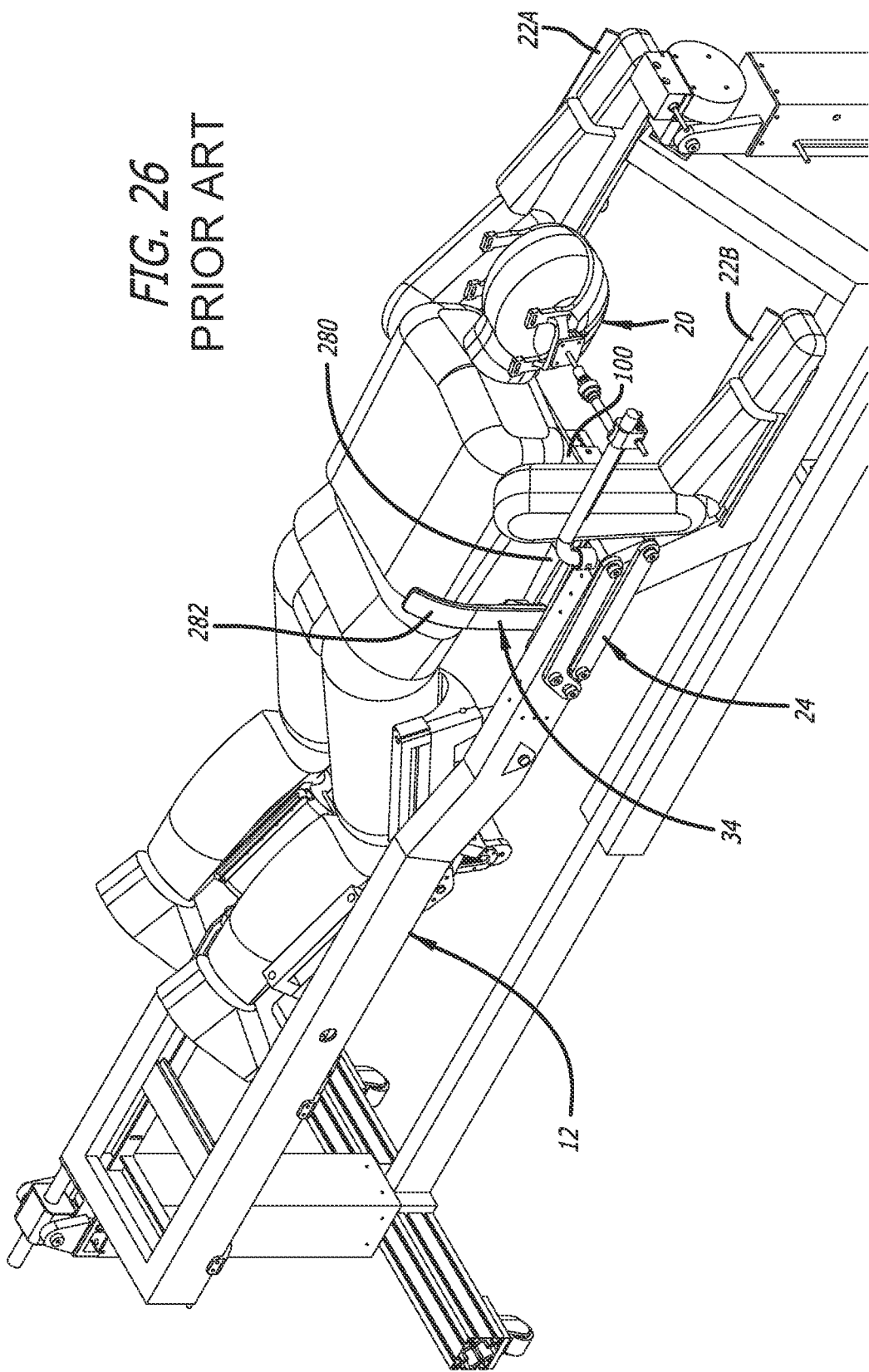
FIG. 26 is a top perspective view that illustrates a portion of the surgical frame of FIG. 1 showing operation of the coronal adjustment assembly.
Figure 27:
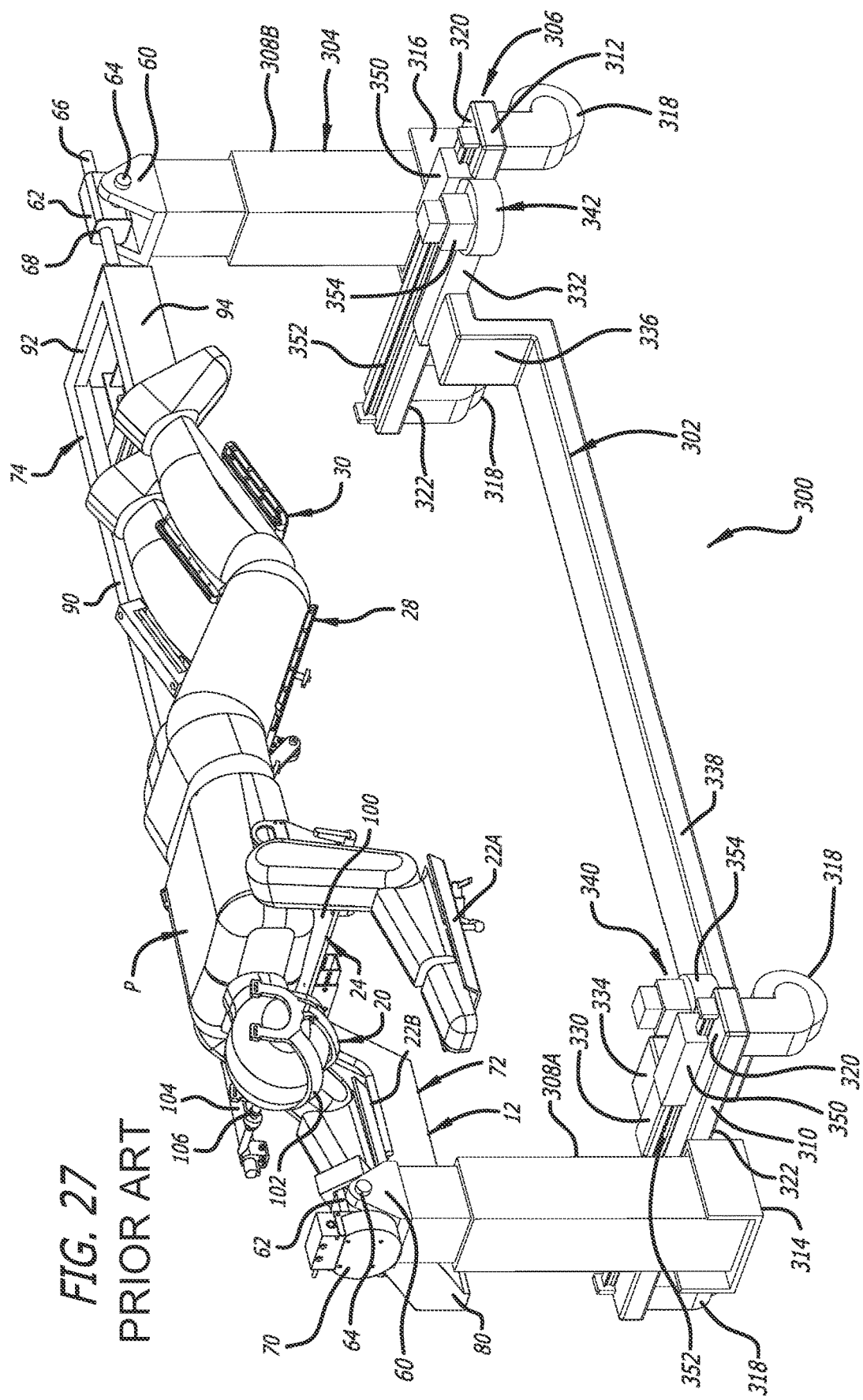
FIG. 27 is a top perspective view that illustrates a prior art surgical frame in accordance with an embodiment of the present invention with the patient positioned thereon in a prone position showing a translating beam thereof in a first position.

As depicted in FIGS. 24-26, for example, the coronal adjustment assembly 34 is configured to support and manipulate the patient's torso, and further to correct a spinal deformity, including but not limited to a scoliotic spine. As depicted in FIGS. 24-26, for example, the coronal adjustment assembly 34 includes a lever 280 linked to an arcuate radiolucent paddle 282. As depicted in FIGS. 24 and 25, for example, a rotatable shaft 284 is linked to the lever 280 via a transmission 286, and the rotatable shaft 284 projects from an end of the chest support plate 100. Rotation of the rotatable shaft 284 is translated by the transmission 286 into rotation of the lever 280, causing the paddle 282, which is linked to the lever 280, to swing in an arc. Furthermore, a servomotor (not shown) interconnected with the rotatable shaft 284 can be computer controlled and/or operated by the operator of the surgical frame 10 to facilitate controlled rotation of the lever 280.

As depicted in FIG. 24, for example, adjustments can be made to the position of the paddle 282 to manipulate the torso and straighten the spine. As depicted in FIG. 25, when the offset main beam 12 is positioned such that the patient P is positioned in a lateral position, the coronal adjustment assembly 34 supports the patient's torso. As further depicted in FIG. 26, when the offset main beam 12 is positioned such that the patient P is positioned in a prone position, the coronal adjustment assembly 34 can move the torso laterally, to correct a deformity, including but not limited to a scoliotic spine. When the patient is strapped in via straps (not shown) at the chest and legs, the torso is relatively free to move and can be manipulated. Initially, the paddle 282 is moved by the lever 280 away from the offset main beam 12. After the paddle 282 has been moved away from the offset main beam 12, the torso can be pulled with a strap towards the offset main beam 12. The coronal adjustment assembly 34 also includes safety stops (not shown) to prevent over-extension or compression of the patient, and sensors (not shown) programmed to send patient position feedback to the safety stops.

A preferred embodiment of a surgical frame incorporating a translating beam is generally indicated by the numeral 300 in FIGS. 27-30. Like the surgical frame 10, the surgical frame 300 serves as an exoskeleton to support the body of the patient P as the patient's body is manipulated thereby. In doing so, the surgical frame 300 serves to support the patient P such that the patient's spine does not experience unnecessary stress/torsion.

The surgical frame 300 includes translating beam 302 that is generally indicated by the numeral 302 in FIGS. 27-30. The translating beam 302 is capable of translating motion affording it to be positioned and repositioned with respect to portions of the remainder of the surgical frame 300. As discussed below, the positioning and repositioning of the translating beam 302, for example, affords greater access to a patient receiving area A defined by the surgical frame 300, and affords greater access to the patient P by a surgeon and/or a surgical assistant (generally indicated by the letter S in FIG. 30) via access to either of the lateral sides $L_1$ and $L_2$ (FIG. 30) of the surgical frame 300.

As discussed below, by affording greater access to the patient receiving area A, the surgical frame 300 affords transfer of the patient P from and to a surgical table/gurney. Using the surgical frame 300, the surgical table/gurney can be conventional, and there is no need to lift the surgical table/gurney over portions of the surgical frame 300 to afford transfer of the patient P thereto.

The surgical frame 300 is configured to provide a relatively minimal amount of structure adjacent the patient's spine to facilitate access thereto and to improve the quality of imaging available before, during, and even after surgery. Thus, the workspace of a surgeon and/or a surgical assistant and imaging access are thereby increased. The workspace, as discussed below, can be further increased by positioning and repositioning the translating beam 302. Furthermore, radiolucent or low magnetic susceptibility materials can be used in constructing the structural components adjacent the patient's spine in order to further enhance imaging quality.

The surgical frame 300, as depicted in FIGS. 27-30, is similar to the surgical frame 10 except that surgical frame 300 includes a support structure 304 having a support platform 306 incorporating the translating beam 302. The surgical frame 300 incorporates the offset main beam 12 and the features associated therewith from the surgical table 300. As such, the element numbering used to describe the surgical frame 10 is also applicable to portions of the surgical frame 300.

Rather than including the cross member 44, and the horizontal portions 46 and the vertical portions 48 of the first and second support portions 40 and 42, the support structure 304 includes the support platform 306, a first vertical support post 308A, and a second vertical support post 308B. As depicted in FIGS. 27-30, the support platform 306 extends from adjacent one longitudinal end to adjacent the other longitudinal end of the surgical frame 300, and the support platform 306 supports the first vertical support post 308A at the one longitudinal end and supports the second vertical support post 308B at the other longitudinal end.

As depicted in FIGS. 27-30, the support platform 306 (in addition to the translating beam 302) includes a first end member 310, a second end member 312, a first support bracket 314, and a second support bracket 316. Casters 318 are attached to the first and second end members 310 and 312. The first end member 310 and the second end member 312 each include an upper surface 320 and a lower surface 322. The casters 318 can be attached to the lower surface of each of the first and second end members 310 and 312 at each end thereof, and the casters 318 can be spaced apart from one another to afford stable movement of the surgical frame 300. Furthermore, the first support bracket 314 supports the first vertical support post 308A, and the second support bracket 316 supports the vertical second support post 308B.

The translating beam 302 is interconnected with the first and second end members 310 and 312 of the support platform 306, and as depicted in FIGS. 27-30, the translating beam 302 is capable of movement with respect to the first and second end members 310 and 312. The translating beam 302 includes a first end member 330, a second end member 332, a first L-shaped member 334, a second L-shaped member 336, and a cross member 338. The first L-shaped member 334 is attached to the first end member 330 and the cross member 338, and the second L-shaped member 336 is attached to the second end member 332 and the cross member 338. Portions of the first and second L-shaped members 334 and 336 extend downwardly relative to the first and second end members 330 and 332 such that the cross member 338 is positioned vertically below the first and second end member 330 and 332. The vertical position of the cross member 338 relative to the remainder of the surgical frame 300 lowers the center of gravity of the surgical frame 300, and in doing so, serves in adding to the stability of the surgical frame 300.

The translating beam 302, as discussed above, is capable of being positioned and repositioned with respect to portions of the remainder of the surgical frame 300. To that end, the support platform 306 includes a first translation mechanism 340 and a second translation mechanism 342. The first translation mechanism 340 facilitates attachment between the first end members 310 and 330, and the second translation mechanism 342 facilitates attachment between the second end members 312 and 332. The first and second translation mechanism 340 and 342 also facilitate movement of the translating beam 302 relative to the first end member 310 and the second end member 312.

The first and second translation mechanisms 340 and 342 can each include a transmission 350 and a track 352 for facilitating movement of the translating beam 302. The tracks 352 are provided on the upper surface 320 of the first and second end members 310 and 312, and the transmissions 350 are interoperable with the tracks 352. The first and second transmission mechanisms 340 and 342 can each include an electrical motor 354 or a hand crank (not shown) for driving the transmissions 350. Furthermore, the transmissions 350 can include, for example, gears or wheels driven thereby for contacting the tracks 352. The interoperability of the transmissions 350, the tracks 352, and the motors 354 or hand cranks form a drive train for moving the translating beam 302. The movement afforded by the first and second translation mechanism 340 and 342 allows the translating beam 302 to be positioned and repositioned relative to the remainder of the surgical frame 300.

The surgical frame 300 can be configured such that operation of the first and second translation mechanism 340 and 342 can be controlled by an operator such as a surgeon and/or a surgical assistant. As such, movement of the translating beam 302 can be effectuated by controlled automation. Furthermore, the surgical frame 300 can be configured such that movement of the translating beam 302 automatically coincides with the rotation of the offset main beam 12. By tying the position of the translating beam 302 to the rotational position of the offset main beam 12, the center of gravity of the surgical frame 300 can be maintained in positions advantageous to the stability thereof.

During use of the surgical frame 300, access to the patient receiving area A and the patient P can be increased or decreased by moving the translating beam 302 between the lateral sides $L_1$ and $L_2$ of the surgical frame 300. Affording greater access to the patient receiving area A facilitates transfer of the patient P between the surgical table/gurney and the surgical frame 300. Furthermore, affording greater access to the patient P facilitates ease of access by a surgeon and/or a surgical assistant to the surgical site on the patient P.

Figure 28:
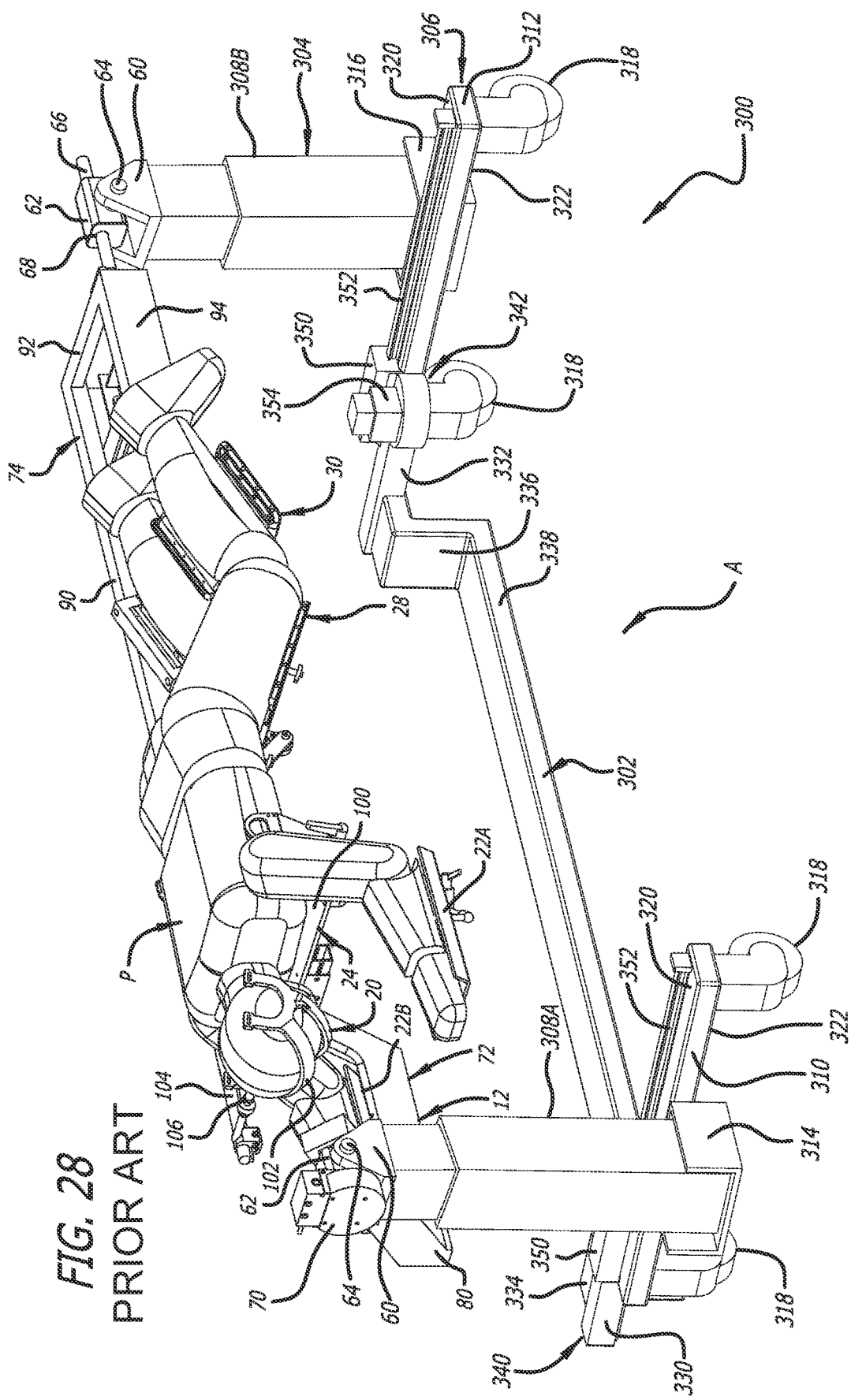
FIG. 28 is another top perspective view that illustrates the surgical frame of FIG. 27 with the patient in a prone position showing the translating beam thereof in a second position.
Figure 29:
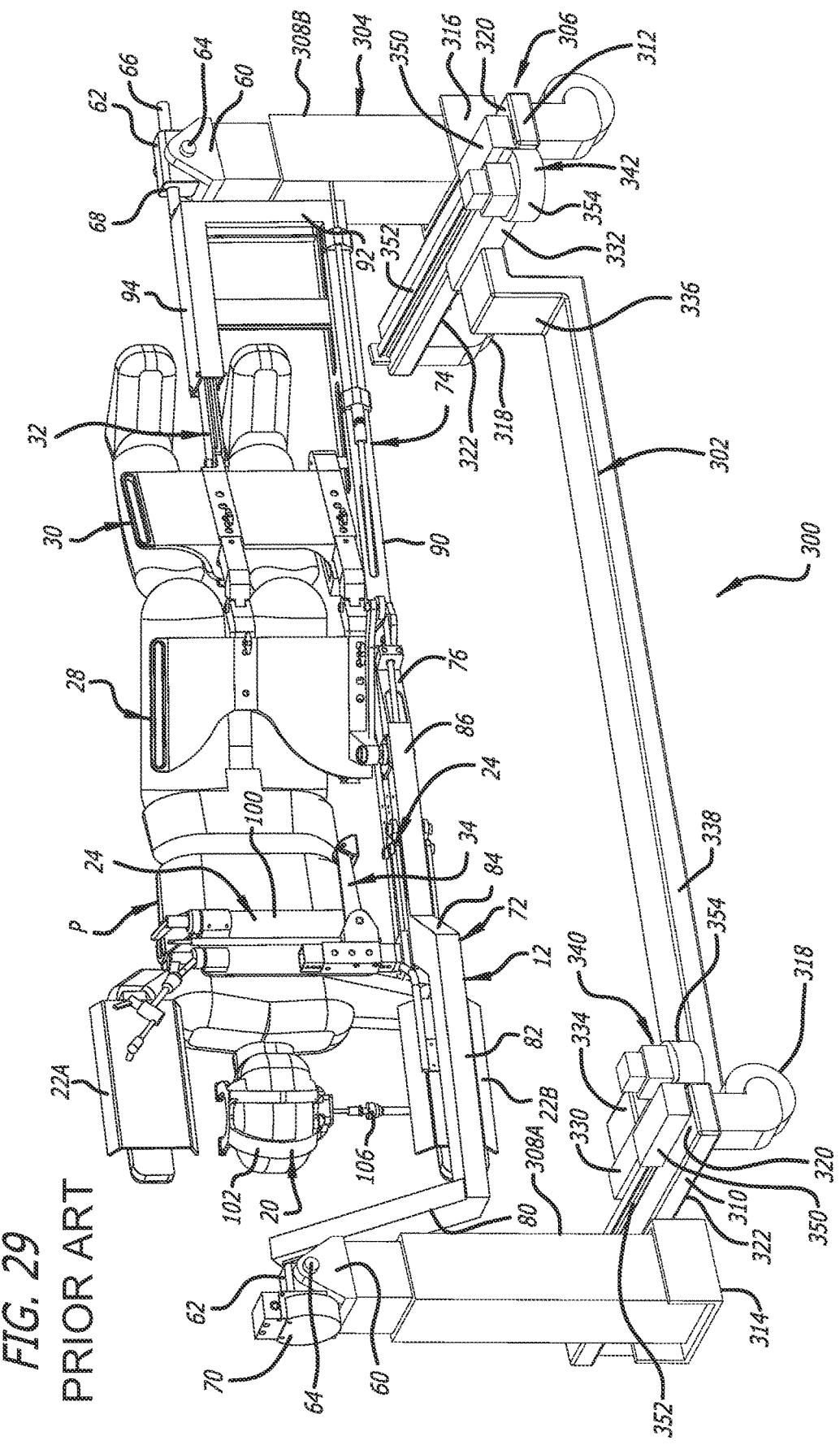
FIG. 29 is yet another top perspective view that illustrates the surgical frame of FIG. 27 with the patient in a lateral position showing the translating beam thereof in a third position.
Figure 30:
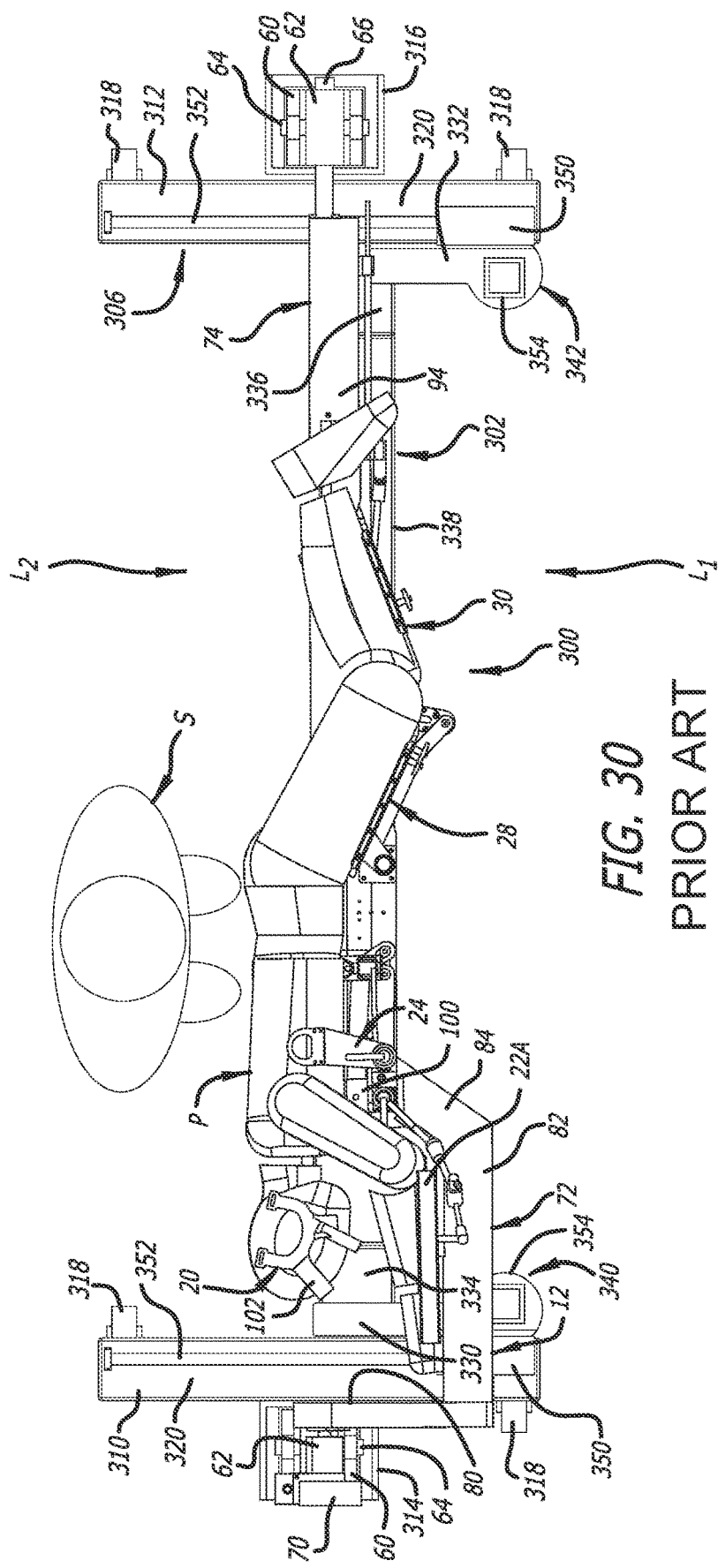
FIG. 30 is a top plan view that illustrates the surgical frame of FIG. 27 with the patient in a lateral position showing the translating beam thereof in the third position.

The translating beam 302 is moveable using the first and second translation mechanisms 340 and 342 between a first terminal position (FIG. 28) and a second terminal position (FIGS. 29 and 30). The translating beam 302 is positionable at various positions (FIG. 27) between the first and second terminal positions. When the translating beam 302 is in the first terminal position, as depicted in FIG. 28, the translating beam 302 and its cross member 338 are positioned on the lateral side $L_1$ of the surgical frame 300. Furthermore, when the translating beam 302 is in the second terminal position, as depicted in FIGS. 29 and 30, the translating beam 302 and its cross member 338 are positioned in the middle of the surgical frame 300.

With the translating beam 302 and its cross member 338 moved to be positioned at the lateral side $L_1$, the surgical table/gurney and the patient P positioned thereon can be positioned under the offset main beam 12 in the patient receiving area A to facilitate transfer of the patient P to or from the offset main beam 12. As such, the position of the translating beam 302 at the lateral side $L_1$ enlarges the patient receiving area A so that the surgical table/gurney can be received therein to allow such transfer to or from the offset main beam 12.

Furthermore, with the translating beam 302 and its cross member 338 moved to be in the middle of the surgical frame 300 (FIGS. 29 and 30), a surgeon and/or a surgical assistant can have access to the patient P from either of the lateral sides $L_1$ or $L_2$. As such, the position of the translating beam 302 in the middle of the surgical frame 300 allows a surgeon and/or a surgical assistant to get close to the patient P supported by the surgical frame 300. As depicted in FIG. 30, for example, a surgeon and/or a surgical assistant can get close to the patient P from the lateral side $L_2$ without interference from the translating beam 302 and its cross member 338. The position of the translating beam 302 can be selected to accommodate access by both a surgeon and/or a surgical assistant by avoiding contact thereof with the feet and legs of a surgeon and/or a surgical assistant.

The position of the translating beam 302 and its cross member 338 can also be changed according to the rotational position of the offset main beam 12. To illustrate, the offset main beam 12 can be rotated a full 360° before, during, and even after surgery to facilitate various positions of the patient to afford various surgical pathways to the patient's spine depending on the surgery to be performed. For example, the offset main beam 12 can be positioned by the surgical frame 300 to place the patient P in a prone position (e.g., FIGS. 27 and 28), lateral positions (e.g., FIGS. 29 and 30), and in a position 45° between the prone and lateral positions. The translating beam 302 can be positioned to accommodate the rotational position of the offset main beam 12 to aid in the stability of the surgical frame 300. For example, when the patient P is in the prone position, the translating beam 302 can preferably be moved to the center of the surgical frame 300 underneath the patient P. Furthermore, when the patient P is in one of the lateral positions, the translating beam 302 can be moved toward one of the corresponding lateral sides $L_1$ and $L_2$ of the surgical frame 300 to position underneath the patient P. Such positioning of the translating beam 302 can serve to increase the stability of the surgical frame 300.

Figure 31:
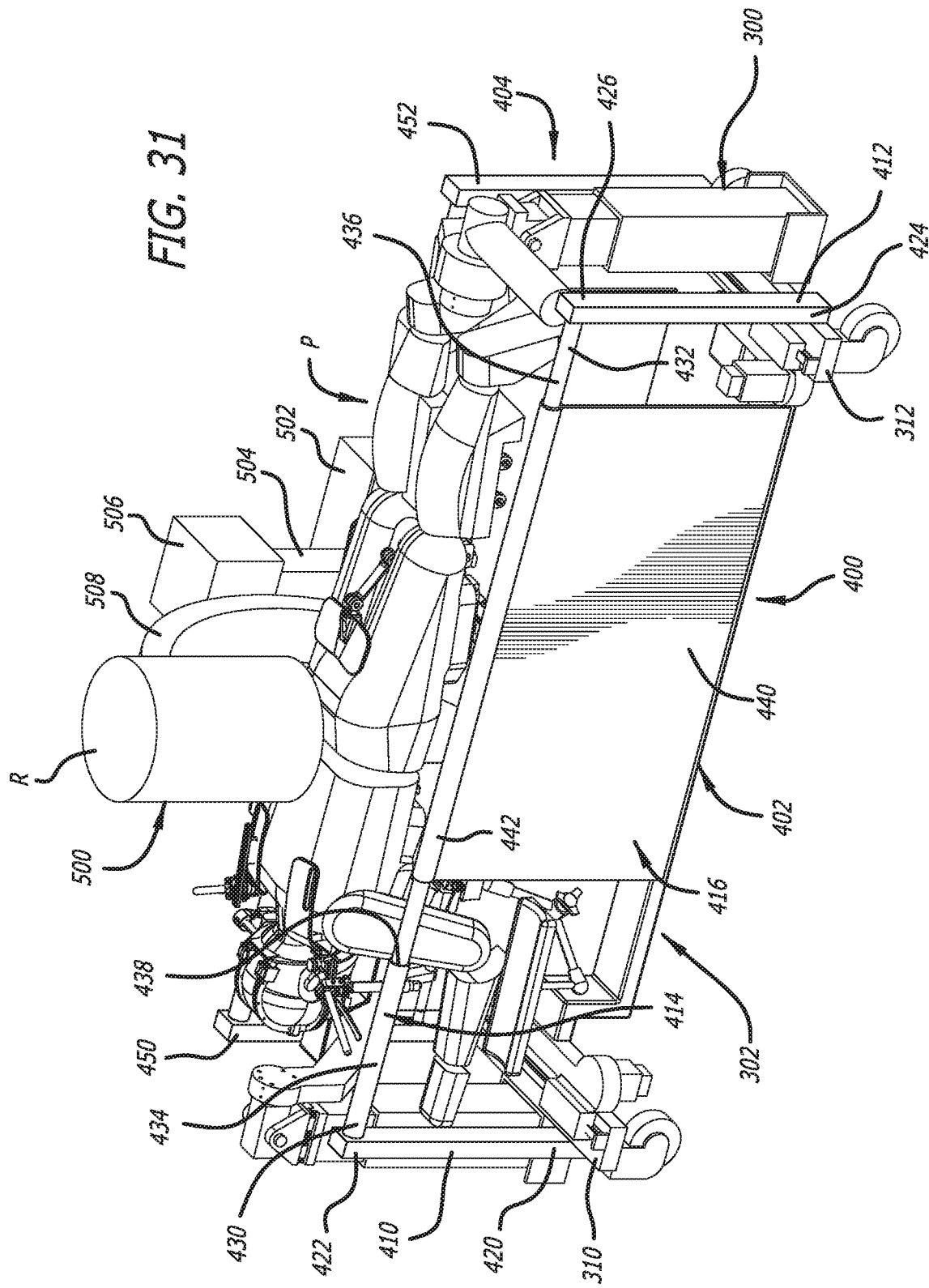
FIG. 31 is a top perspective view that illustrates a first side of a first embodiment of a radiation-scatter mitigating system, for mitigating radiation from a radiation emitter, that is at least partially integrated into a surgical frame.
Figure 32:
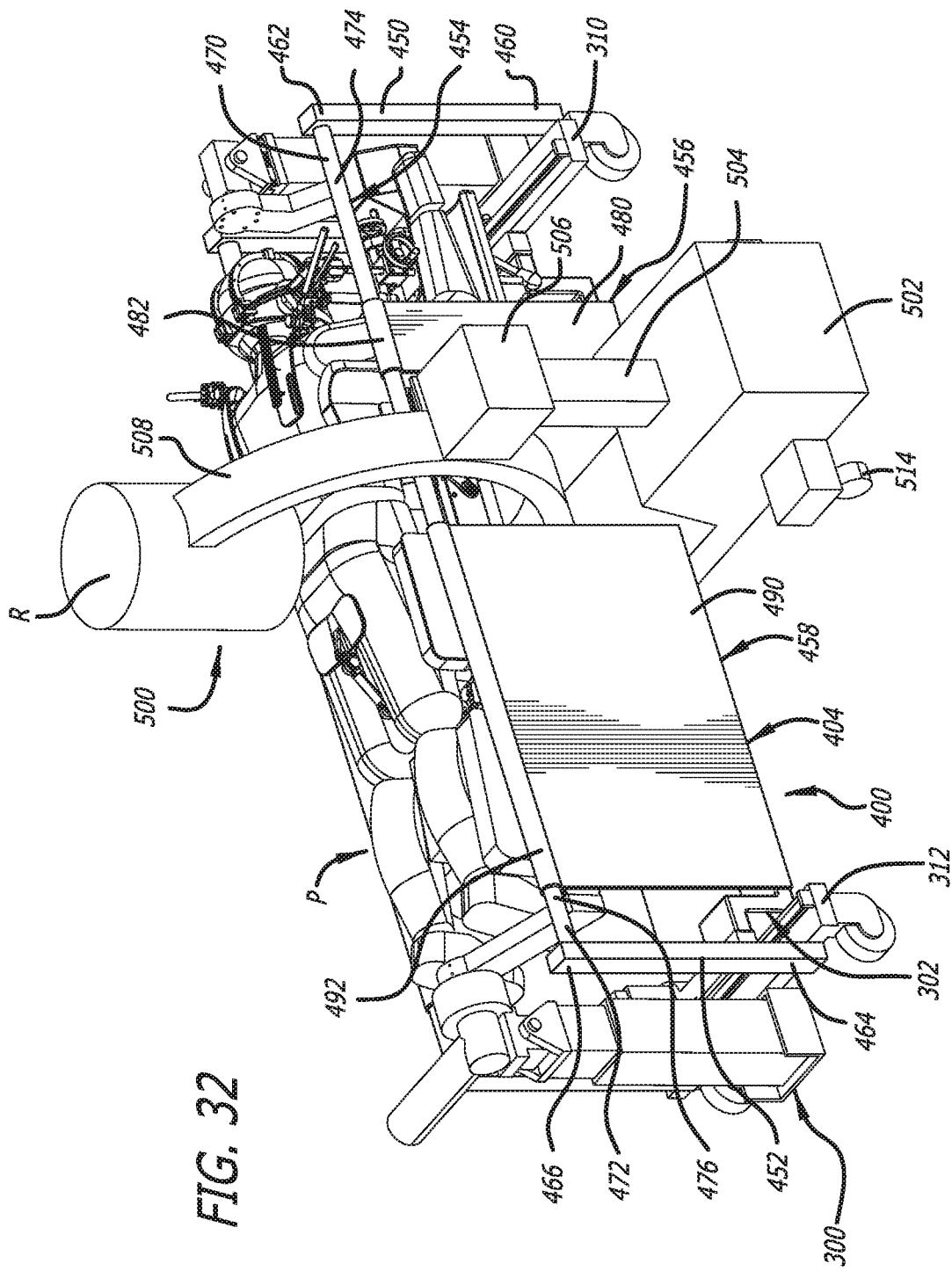
FIG. 32 is a top perspective view that illustrates a second side of the first embodiment of the radiation-scatter mitigating system of FIG. 31 that is at least partially integrated into the surgical frame.
Figure 33:
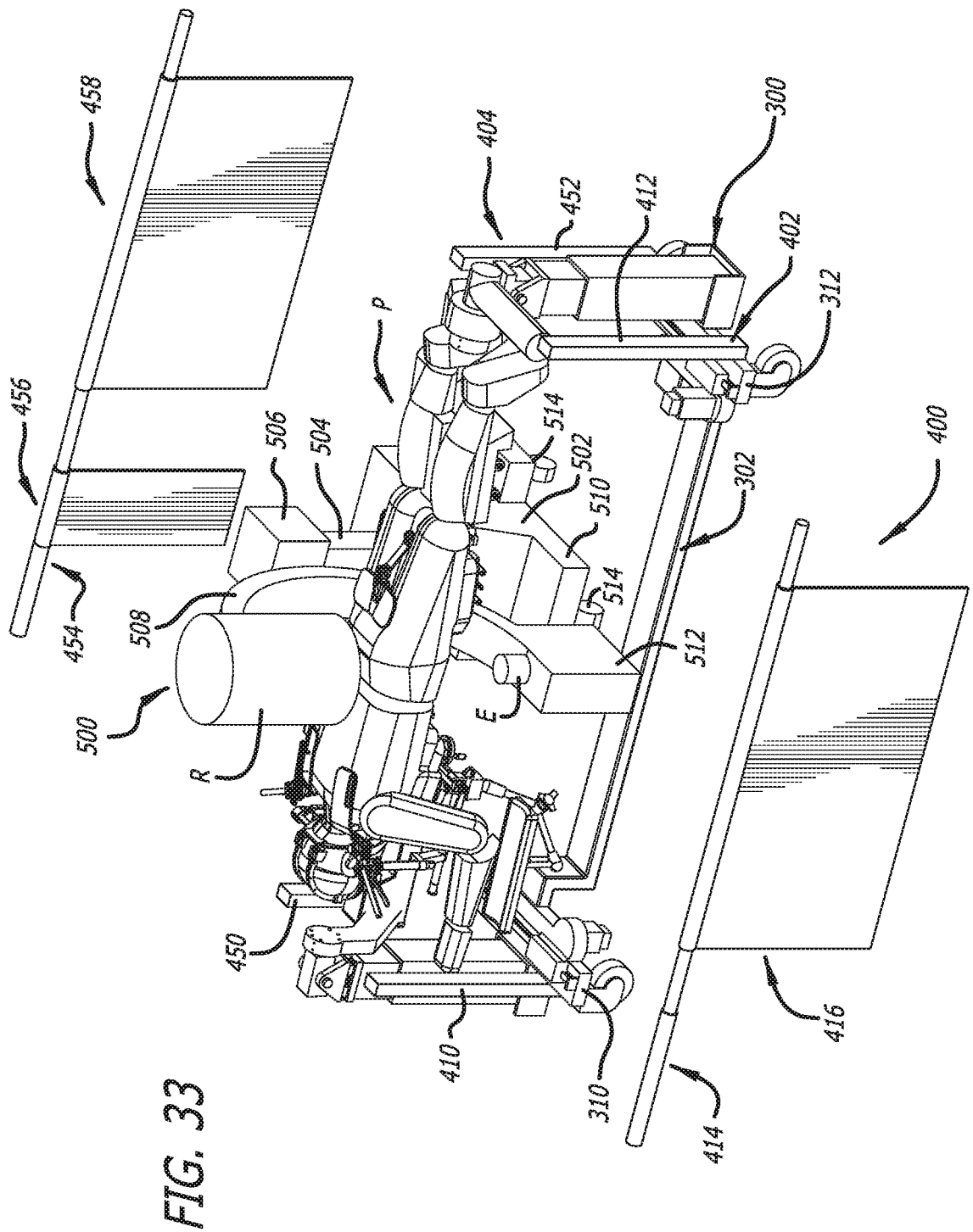
FIG. 33 is a partially exploded top perspective view that illustrates the first side of the first embodiment of the radiation-scatter mitigating system of FIG. 31 with radiation shields used therein spaced from the surgical frame.

A radiation-scatter mitigating system 400 is depicted in FIGS. 31-33. The radiation-scatter mitigating system 400 is used in mitigating unwanted scatter of electromagnetic radiation used for imaging techniques applied to a patient P. In doing so, the radiation-mitigating system 400 serves in shielding areas around the radiation-mitigating system 400 from the unwanted scatter of the electromagnetic radiation from an electromagnetic-radiation imaging system including an emitter E and a receiver R. The radiation-scatter mitigating system 400 can be used with surgical frames 10 and 300. To image certain portions of the patient's body, the surgical frames 10 and 300 can be rotated relative to the emitter E and the receiver R, and/or, as discussed below, the emitter E and the receiver R can be positioned relative to the surgical frames 10 and 300.

As depicted FIGS. 31-33, the radiation-scatter mitigating system 400 is used with the surgical frame 300, and includes a first side portion 402 and a second side portion 404. The first side portion 402 extends along a first lateral side of the surgical frame 300, and the second side portion 404 extends along a second lateral side of the surgical frame 300.

As depicted in FIGS. 31 and 33, the first side portion 402 includes a first post portion 410, a second post portion 412, a bar portion 414, and at least one radiation shield 416. The first post portion 410 and the second post portion 412 can serve as stanchions, and can be attached to and supported by the support platform 306. The first post portion 410 and the second post portion 412 each extend upwardly from the support platform 306. Furthermore, the first post portion 410 includes a first end 420 and a second end 422, and the second post portion 412 includes a first end 424 and a second end 426. As depicted in FIG. 31, for example, the first end 420 of the first post portion 410 is attached to the first end member 310, and the first end 424 of the second post portion 412 is attached to the second end member 312.

As depicted in FIGS. 31, the bar portion 414 includes a first end 430 and a second end 432 with the first end 430 being supported by the second end 422 of the first post portion 410, and the second end 432 being supported by the second end 426 of the second post portion 412. As such, the first post portion 410 and the second post portion 412 are used to support and space the bar portion 414 from the ground. The bar portion 414 can be expandable and contractable to facilitate attachment to the first post portion 410 and the second post portion 412. To facilitate such expansion and contraction, the bar portion 414 can include a first portion 434 and a second portion 436 with the second portion 436 being moveable inwardly and outwardly of a recess 438 formed in the first portion 434.

The at least one radiation shield 416 is attached to and supported by the bar portion 414. Although only one radiation shield 416 is depicted in FIGS. 31 and 33, multiple radiation shields 416 can be attached to and supported by the bar portion 414, and each of the radiation shield(s) 416 can function in a similar manner. The radiation shield(s) 416 can include a body portion 440 and an attachment portion 442. The body portion 440 and the attachment portion 442 each can be formed at least in part from a radiation blocking/intercepting material such as, for example, lead, tin, antimony, tungsten, bismuth, and compounds and/or composites thereof. To illustrate, the body portion 440 and the attachment portion 442 can be formed of a synthetic or non-synthetic fabric that includes a lead lining. The attachment portion 442 is used to attach the body portion 440 relative to the bar portion 414, and although depicted in FIG. 31 as being flattened, the body portion 440 can include folds such as accordion-pleats affording expansion or contraction along the bar portion 414. The body portion 440 can extend from the bar portion 414 or from adjacent to the bar portion 414 to or adjacent to the ground supporting the surgical frame 300.

As depicted in FIG. 31, the attachment portion 442 can be formed by one or more loops through which the bar portion 414 is received. In addition or alternatively to the one or more loops, mechanical connectors such as brackets, hooks, rings, and/or sliders can be used to facilitate attachment of the radiation shield 416 to the bar portion 414. The one or more loops or mechanical connectors can be used to facilitate movement of the radiation shield 416 along the bar portion 414. Furthermore, the folds formed in the body portion 440 can be used to facilitate expansion and contraction of the radiation shield 416.

The expansion and contraction of the radiation shield 416, in similar fashion to use of curtains/drapes with a window, can close off (via expansion) or provide access (via contraction) to areas underneath the main beam 12. To illustrate, when the radiation shield 416 is expanded, the radiation shield 416 serves to intercept/block and mitigate at least some of the scatter of the electromagnetic radiation from the emitter E, and when the radiation shield 416 is contracted, the radiation shield 416 affords access underneath the main beam 12.

As depicted in FIGS. 32 and 33, the second side portion 404 includes a first post portion 450, a second post portion 452, a bar portion 454, and at least a first radiation shield 456 and a second radiation shield 458. The first post portion 450 and the second post portion 452 can serve as stanchions, and can be attached to and supported by the support platform 306. The first post portion 450 and the second post portion 552 each extend upwardly from the support platform 306. Furthermore, the first post portion 450 includes a first end 460 and a second end 462, and the second post portion 452 includes a first end 464 and a second end 466. As depicted in FIG. 32, for example, the first end 460 of the first post portion 450 is attached to the first end member 310, and the first end 464 of the second post portion 452 is attached to the second end member 312.

As depicted in FIGS. 32, the bar portion 454 includes a first end 470 and a second end 472 with the first end 470 being supported by the second end 462 of the first post portion 450, and the second end 472 being supported by the second end 466 of the second post portion 452. As such, the first post portion 450 and the second post portion 452 are used to support and space the bar portion 454 from the ground. The bar portion 454 can be expandable and contractable to facilitate attachment to the first post portion 450 and the second post portion 452. To facilitate such expansion and contraction, the bar portion 454 can include a first portion 474 and a second portion 476 with the second portion 476 being moveable inwardly and outwardly of a recess (not shown) formed in the first portion 474.

The at least one first radiation shield 456 and the second radiation shield 458 are each attached to and supported by the bar portion 454. Although only one first radiation shield 456 is depicted in FIGS. 32 and 33, multiple first radiation shields 456 can be attached to and supported by the bar portion 454 and each of the first radiation shield(s) 456 can include a body portion 480 and an attachment portion 482. The body portion 480 and the attachment portion 482 each can be formed at least in part from a radiation blocking material such as, for example, lead, tin, antimony, tungsten, bismuth, and compounds and/or composites thereof. To illustrate, the body portion 480 and the attachment portion 482 can be formed of a synthetic or non-synthetic fabric that includes a lead lining. The attachment portion 482 is used to attach the body portion 480 relative to the bar portion 454, and although depicted in FIG. 32 as being flattened, the body portion 480 can include folds such as accordion-pleats affording expansion or contraction along the bar portion 454. The body portion 480 can extend from the bar portion 454 or from adjacent to the bar portion 454 to or adjacent to the ground supporting the surgical frame 300.

As depicted in FIG. 32, the attachment portion 482 can be formed by one or more loops through which the bar portion 454 is received. In addition or alternatively to the one or more loops, mechanical connectors such as brackets, hooks, rings, and/or sliders can be used to facilitate attachment of the first radiation shield 456 to the bar portion 454. The one or more loops or mechanical connectors can be used to facilitate movement of the first radiation shield 456 along the bar portion 454. Furthermore, the folds formed in the body portion 480 can be used to facilitate expansion and contraction of the first radiation shield 456.

The expansion and contraction of the first radiation shield 456, in similar fashion to use of curtains/drapes with a window, can close off (via expansion) or provide access (via contraction) to areas underneath the main beam 12. To illustrate, when the first radiation shield 456 is expanded, the first radiation shield 456 serves to intercept/block and mitigate at least some of the scatter of the electromagnetic radiation from the emitter E, and when the first radiation shield 456 is contracted, the first radiation shield 456 affords access underneath the main beam 12.

Although only one second radiation shield 458 is depicted in FIGS. 32 and 33, multiple second radiation shields 458 can be attached to and supported by the bar portion 454 and each of the second radiation shield(s) 458 can include a body portion 490 and an attachment portion 492. The body portion 490 and the attachment portion 492 each can be formed at least in part from a radiation blocking/intercepting material such as, for example, lead, tin, antimony, tungsten, bismuth, and compounds and/or composites thereof. To illustrate, the body portion 490 and the attachment portion 492 can be formed of a synthetic or non-synthetic fabric that includes a lead lining. The attachment portion 492, like the attachment portion 482, is used to attach the body portion 490 relative to the bar portion 454, and although depicted in FIG. 32 as being flattened, the body portion 490 can include folds such as accordion-pleats affording expansion or contraction along the bar portion 454. The body portion 490 can extend from the bar portion 454 or from adjacent to the bar portion 454 to or adjacent to the ground supporting the surgical frame 300.

As depicted in FIG. 32, the attachment portion 492 can be formed by one or more loops through which the bar portion 454 is received. In addition or alternatively to the one or more loops, mechanical connectors such as brackets, hooks, rings, and/or sliders can be used to facilitate attachment of the second radiation shield 458 to the bar portion 454. The one or more loops or mechanical connectors can be used to facilitate movement of the second radiation shield 458 along the bar portion 454. Furthermore, the folds formed in the body portion 490 can be used to facilitate expansion and contraction of the second radiation shield 458.

The expansion and contraction of the second radiation shield 458, in similar fashion to use of curtains/drapes with a window, can close off (via expansion) or provide access (via contraction) to areas underneath the main beam 12. To illustrate, when the second radiation shield 458 is expanded, the second radiation shield 458 serves to intercept/block and mitigate at least some of the scatter of the electromagnetic radiation from the emitter E, and when the second radiation shield 458 is contracted, the second radiation shield 458 affords access underneath the main beam 12.

Additional radiation shields (not shown) can be used with the radiation-scatter mitigating system 400 and be provided at either end of the surgical frame 300 to further intercept/block radiation scatter, and these additional radiation shields can have configurations and be supported in similar fashion to the radiation shield 416, the first radiation shield 456, and/or the second radiation shield 458.

The expansion of the radiation shield 416, the first radiation shield 456, the second radiation shield 458, and the additional radiation shields can serve to at least partially enclose the emitter E therebetween. Thus, during operation of the emitter E, radiation therefrom can be at least partially blocked/intercepted from escaping through the radiation shield 416, the first radiation shield 456, the second radiation shield 458, and the additional radiation shields.

Furthermore, as depicted in FIGS. 31-33, the emitter E and the receiver R can be incorporated in a C-arm assembly 500 of the electromagnetic-radiation imaging system. The C-arm assembly 500 can be used in maintaining the locations of the emitter E and the receiver R with respect to one another to facilitate operation of the imaging techniques applied to the patient P. The C-arm assembly 500 includes a cart portion 502, a post portion 504, a head portion 506, a C-arm portion 508, an extension portion 510, and a base portion 512. The receiver R can be supported by the C-arm portion 508, the emitter E can be supported by the base portion 512, and the C-arm assembly 500 can be used in positioning and repositioning the emitter E and the receiver R relative to the patient P and the main beam 12. Furthermore, the C-arm portion 508 can alternatively be attached to the head portion 506, the extension portion 510 and/or the base portion 512, or the translating beam 302.

The emitter E and the receiver R could be moveable upwardly and downwardly toward or away from one another and the patient P using a modified C-arm portion 508 and/or a modified base portion 512. The receiver R could be moveable upwardly and downwardly relative to the modified C-arm, and the modified base portion 512 can be configured to be telescopically expandable and contractable. The modified C-arm and the modified base portion 512 can facilitate movement of the emitter E and/or the receiver R relative to one another and the patient P.

Rather than being attached to the translating beam 302, the C-arm portion 508, the base portion 512, the modified C-arm portion 508, or the modified base portion 512 could be attached to a slide bar (not shown) that is attached to the translating beam 302. The slide bar could be arranged transversely to and extend on either or both of the lateral sides of the translating beam 302. To facilitate positioning of the emitter E, the slide bar could be moveable along the translating beam 302 using a track (not shown) from between a location at least adjacent the first end member 310 and at least adjacent the second end member 312, and the C-arm portion 508, the base portion 512, the modified C-arm portion 508, or the modified base portion 512 could be moveable along the slide bar using a track (not shown) from between a location adjacent a first end of the slide bar and a location adjacent a second end of the slide bar.

Furthermore, a fixed beam (rather the translating beam 302) that extends between, for example, the first end member 310 and the second end member 312 could be used with the slide bar. Movement of the slide bar on the fixed beam from between a location at least adjacent the first end member 310 and at least adjacent the second end member 312, and movement of the C-arm portion 508, the base portion 512, the modified C-arm portion 508, or the modified base portion 512 on the slide bar from between a location adjacent a first end of the slide bar and a location adjacent a second end of the slide bar can afford similar positioning of the emitter E as with the translating beam 302 and the track provided thereon.

The cart portion 502 can be unattached or attached to the surgical frame 300, and can include various casters 514 facilitating movement thereof relative to the ground. When the cart portion 502 is unattached to the surgical frame 300, a user can position and reposition the cart portion 502 (and the componentry supported by the cart portion 502) relative to the patient P and/or the surgical frame 300. For example, the C-arm portion 508 (supporting the receiver R) and/or the base portion 512 (supporting the emitter E) can be attached relative to the cart portion 502, and thus, the user can position and reposition the emitter E and the receiver R relative to the patient P and/or the surgical frame 300 by moving the cart portion 502.

Alternatively, the cart portion 502 can be attached relative to the translating beam 302. To illustrate, the extension portion 510 can be attached to the cart portion 502, the base portion 512 can be attached to the extension portion 510, and the extension portion 510 and/or the base portion 512 can be attached relative to the translating beam 302. As such, when the translating beam 302 moves, the cart portion 502 moves with the movement of the translating beam 302. Additionally, the extension portion 510 and/or the base portion 512 can be interconnected with a track (not shown) extending along the translating beam 302 that affords movement of the extension portion 510 and/or the base portion 512 along the length of the translating beam 302. As such, when the extension portion 510 and/or the base portion 512 move along the track, the cart portion 502 moves with the movement of the extension portion 510 and/or the base portion 512.

Movement of the translating beam 302 and/or movement of the extension portion 510 and/or the base portion 512 along the track can serve in positioning and repositioning the cart portion 502 (and the componentry supported by the cart portion 502). As discussed above, the C-arm portion 508 (supporting the receiver R) and/or the base portion 512 (supporting the emitter E) can be attached relative to the cart portion 502, and thus, movement of the cart portion 502 serves to position and reposition the emitter E and the receiver R relative to the patient P and/or the surgical frame 300.

The C-arm portion 508 can be attached at different locations relative to the cart portion 502. For example, the C-arm portion 508 can be attached to the head portion 506, and the head portion 506 can be attached to the post portion 504. The post portion 504 can be telescoping to facilitate raising and lowering of the head portion 506 (and the C-arm 508 attached thereto) relative to the cart portion 502. Furthermore, the base portion 512 can be attached to the C-arm portion 508 instead of being attached to the cart portion 502 via the extension portion 510. As such, movement of the head portion 506 via the telescoping post portion 504 can serve in positioning and repositioning the emitter E and the receiver R upwardly and downwardly relative to the patient P and main beam 12. Alternatively, the C-arm 508 can be attached to the extension portion 510 and/or the base portion 512, rather than the head portion 506 or even the post portion 504. Either way, the C-arm portion 508 can correspondingly move with movement of the cart portion 502. Furthermore, the C-arm portion 508 and the base portion 512 can be rotatable relative to the cart portion 502 to facilitate rotation of the emitter E and the receiver R with respect to the patient P.

The C-arm portion 508 and/or the base portion 512 alternatively can be attached relative to the translating beam 302 without use of the cart portion 502. Such attachment is described in U.S. application Ser. No. 16/108,669, which is herein incorporated by reference. Furthermore, the C-arm portion 508 and the base portion 512 can be rotatable relative to the translating beam 302 to facilitate rotation of the emitter E and the receiver R with respect to the patient P. As such, movement of the translating beam 302 and/or movement of the C-arm portion 508 and/or the base portion 512 relative to the translating beam 302 can serve in positioning and repositioning the receiver R (attached to the C-arm portion 508) and/or the emitter E (attached to the base portion 512) without use of the cart portion 502.

Figure 34:
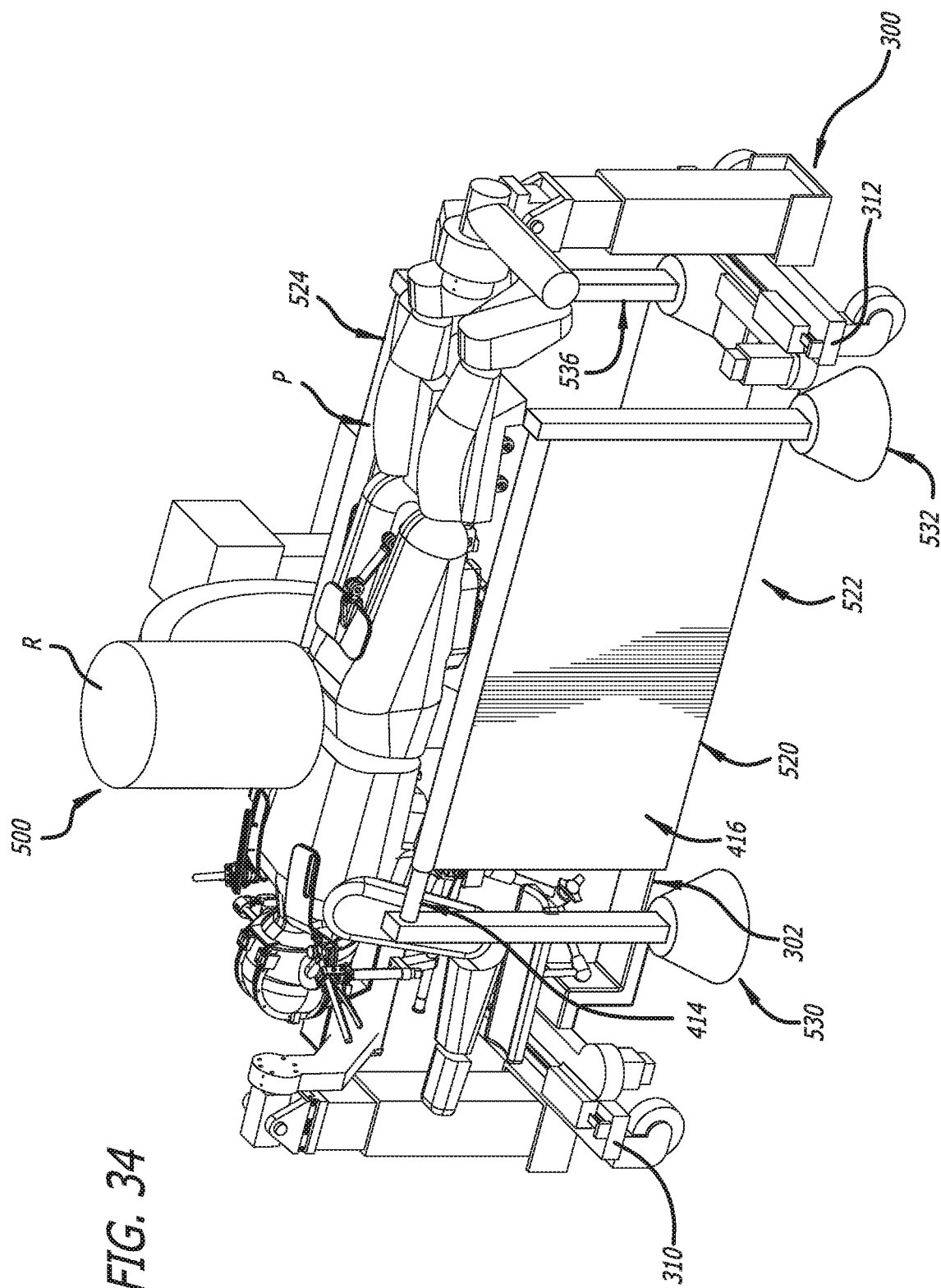
FIG. 34 is a top perspective view that illustrates a first side of a second embodiment of a radiation-scatter mitigating system, for mitigating radiation from a radiation emitter, that is positioned adjacent a surgical frame.
Figure 35:
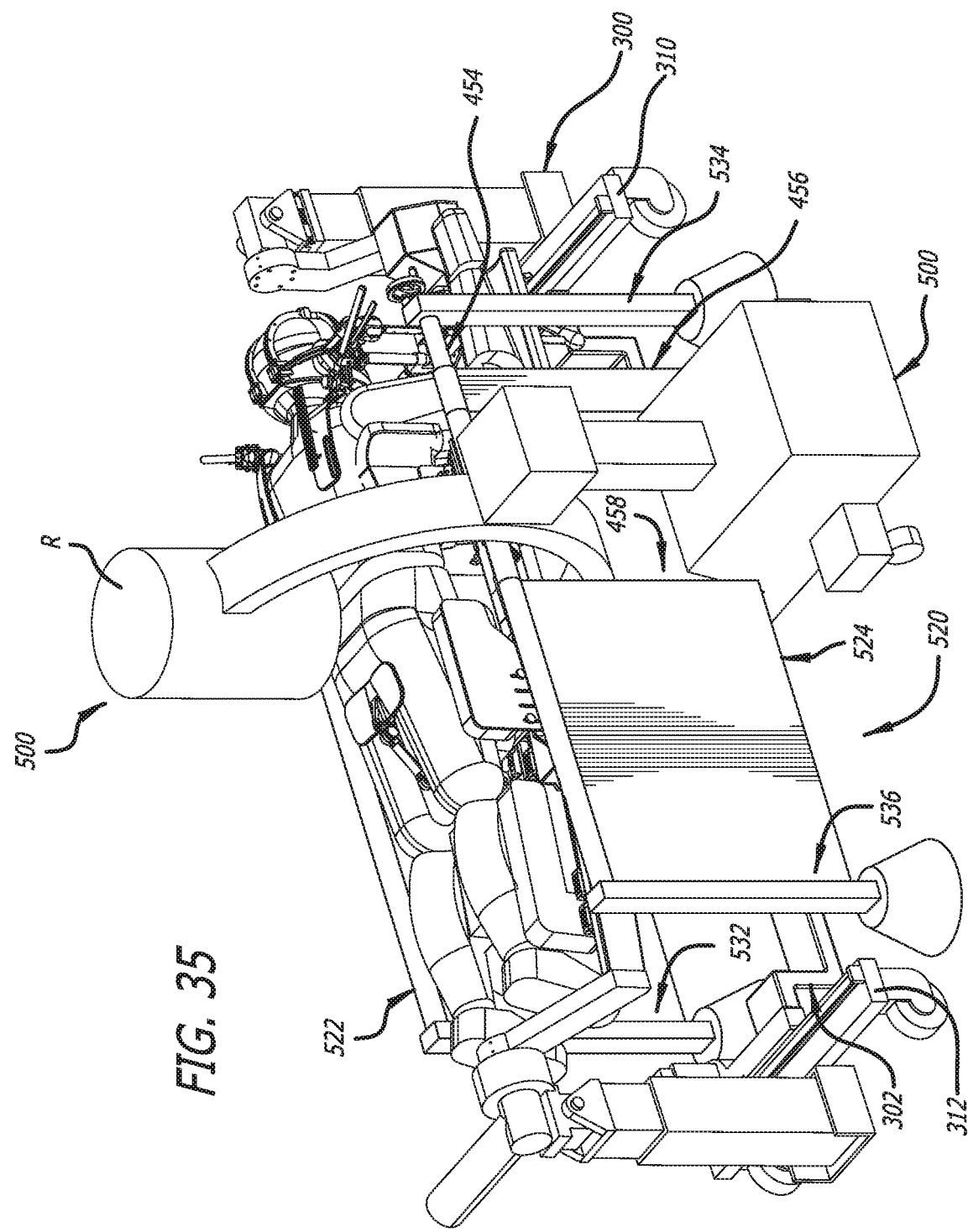
FIG. 35 is a top perspective view that illustrates a second side of the second embodiment of the radiation-scatter mitigating system of FIG. 34 that is positioned adjacent the surgical frame.
Figure 36:
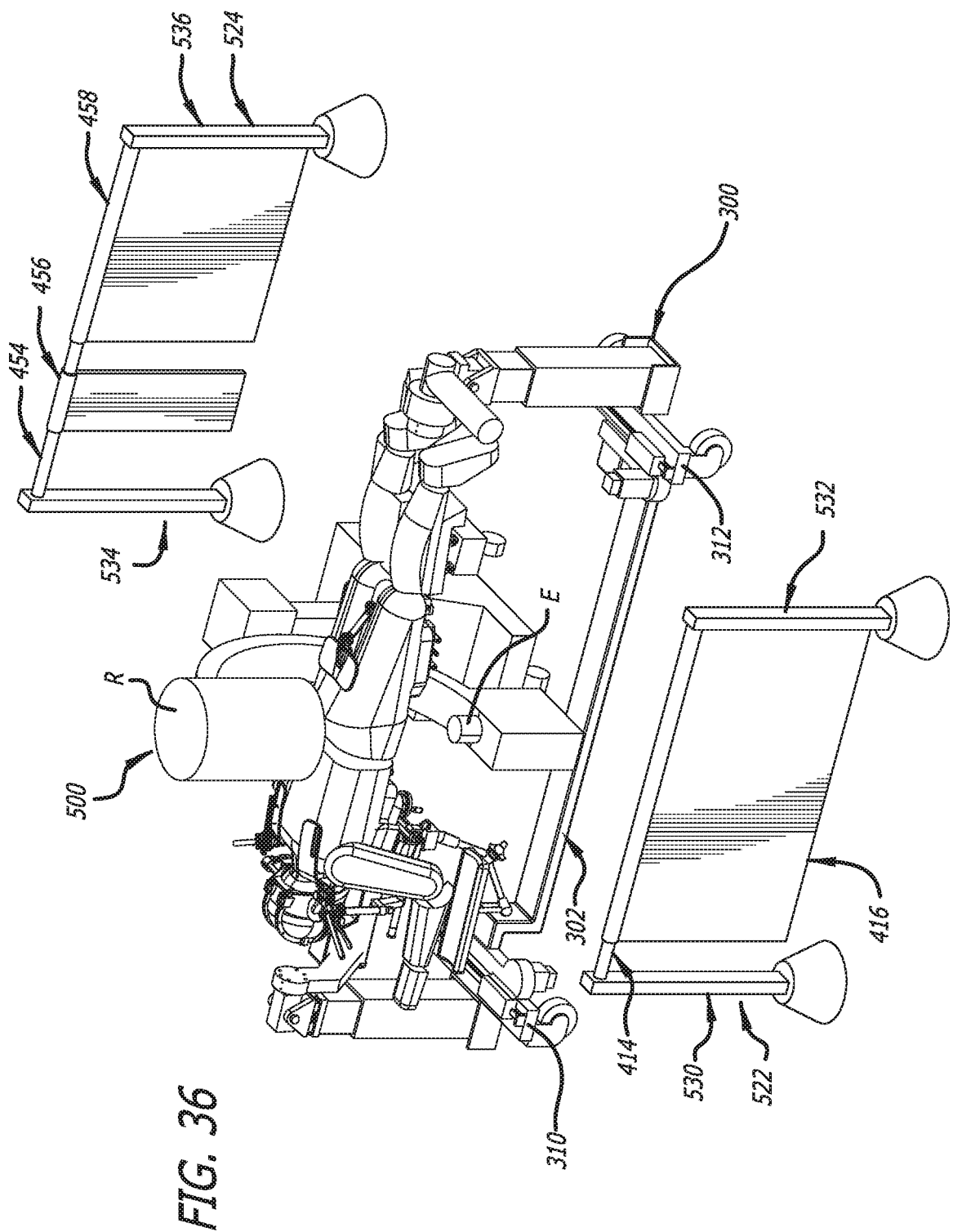
FIG. 36 is a partially exploded top perspective view that illustrates the first side of the second embodiment of the radiation-scatter mitigating system of FIG. 34 with radiation shields used therein spaced from the surgical frame.

As depicted in FIGS. 34-36, a radiation-scatter mitigating system 520 is used with the surgical frame 300, and includes a first side portion 522 and a second side portion 524. Rather than using the first support post portions 410, 450 and the second support post portions 412, 452 that are attached to the surgical frame 300, first and second support post portions can be used for the first side portion 522 and the second side portion 524 that are stands separate from the surgical frame 300. These first and second support post portions can include, but are not limited to, free-standing stands.

As depicted in FIGS. 34 and 36, the first side portion 522 includes a first support post portion 530 and a second support post portion 532. The first support post portion 530 and the second support post portion 532 can serve as stanchions, and can be positioned on either side of each of the first end member 310 and the second end member 312 such that the first support post portion 530 and/or the second support post portion 532 can be positioned within or on the outside of the area between the first end member 310 and the second end member 312. The bar portion 414 and the radiation shield 416 can be used with the first support post portion 530 and the second support post portion 532, and the lengths and sizes of the bar portion 414 and the radiation shield 416 can be adjusted to accommodate the positions of the first support post portion 530 and the second support post portion 532.

Furthermore, as depicted in FIGS. 35 and 36, the second side portion 524 includes a first support post portion 534 and a second support post portion 536. The first support post portion 534 and the second support post portion 536 can serve as stanchions, and can be positioned on either side of each of the first end member 310 and the second end member 312 such that the first support post portion 534 and/or the second support post portion 536 can be positioned within or on the outside of the area between the first end member 310 and the second end member 312. The bar portion 454, the first radiation shield 456, and the second radiation shield 458 can be used with the first support post portion 534 and the second support post portion 536, and the lengths and sizes of the bar portion 454, the first radiation shield 456, and the second radiation shield 458 can be adjusted to accommodate the positions of the first support post portion 534 and the second support post portion 536.

The expansion and contraction of the radiation shield 416 (used in association with the first side portion 522), and the expansion and contraction of the first radiation shield 456 and the second radiation shield 458, in similar fashion to use of curtains/drapes with a window, can close off (via expansion) or provide access (via contraction) to areas underneath the main beam 12. To illustrate, as discussed above, when the radiation shield 416 is expanded, the radiation shield 416 serves to intercept/block and mitigate at least some of the scatter of the electromagnetic radiation from the emitter E, and when the radiation shield 416 is contracted, the radiation shield 416 affords access underneath the main beam 12. Furthermore, as discussed above, when the first radiation shield 456 and the second radiation shield 458 are expanded, the first radiation shield 456 and the second radiation shield 458 serve to intercept/block and mitigate at least some of the scatter of the electromagnetic radiation from the emitter E, and when the first radiation shield 456 and the second radiation shield 458 are contracted, the first radiation shield 456 and the second radiation shield 458 afford access underneath the main beam 12.

Additional radiation shields (not shown) can be used with the radiation-scatter mitigating system 520 and be provided at either end of the surgical frame 300 to further intercept/block radiation scatter, and these additional radiation shields have configurations and be supported in similar fashion to the radiation shield 416, the first radiation shield 456, and/or the second radiation shield 458.

Figure 37:
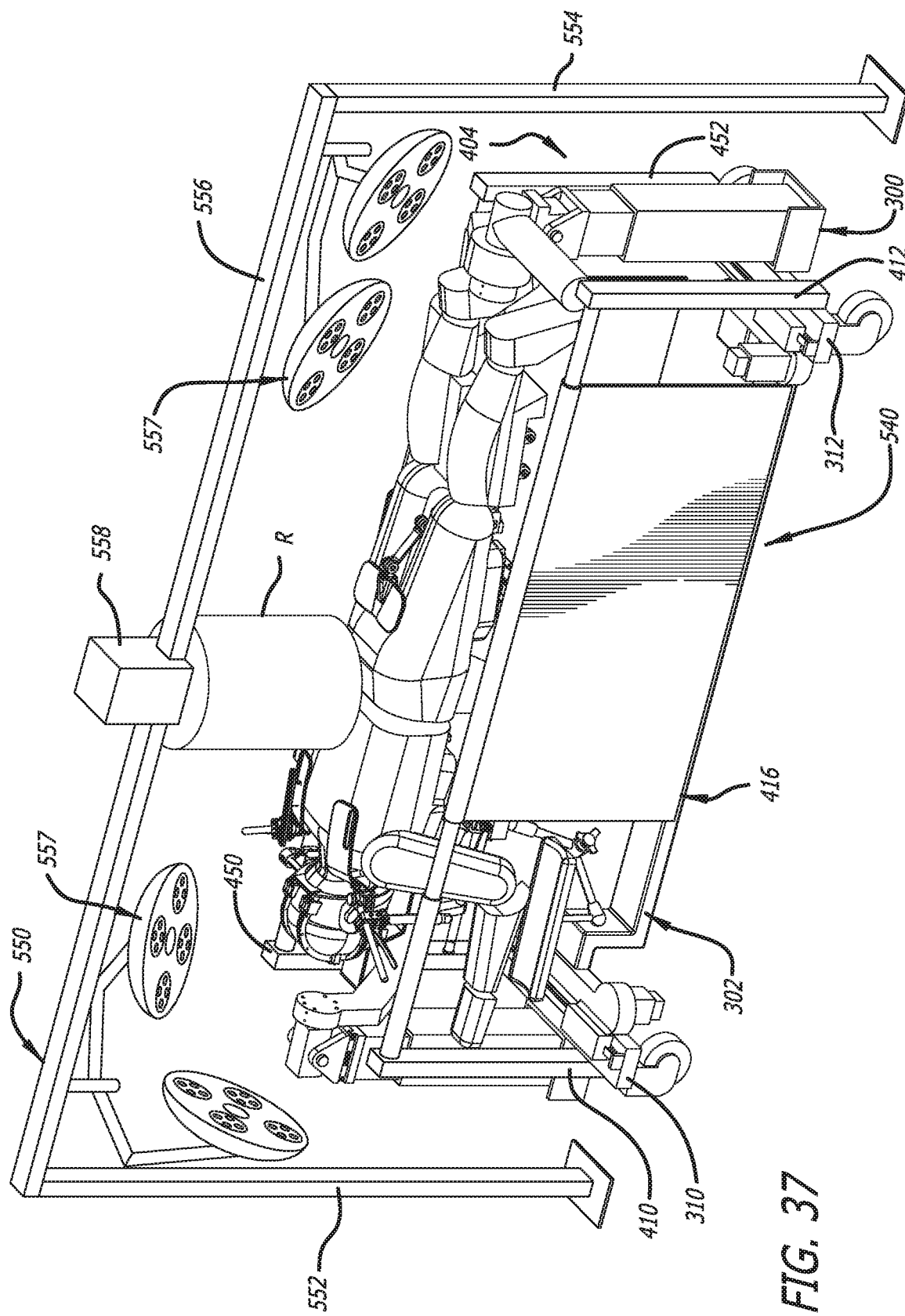
FIG. 37 is a top perspective view that illustrates a first side of a third embodiment of a radiation-scatter mitigating system, for mitigating radiation from a radiation emitter, that is at least partially integrated into a surgical frame and positioned adjacent a receiver-support structure.
Figure 38:
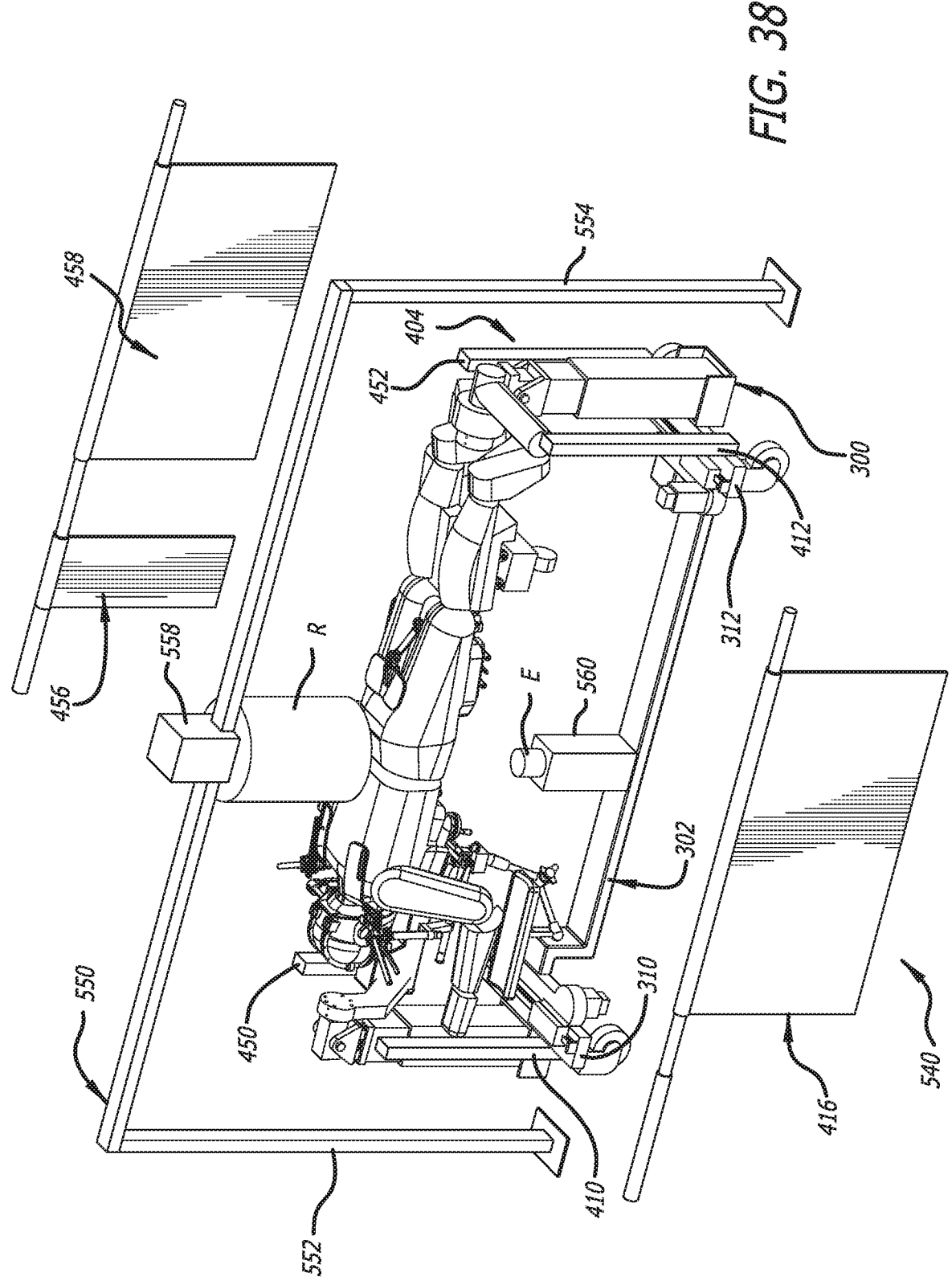
FIG. 38 is a partially exploded top perspective view that illustrates the first side of the third embodiment of the radiation-scatter mitigating system of FIG. 34 with radiation shields used therein spaced from the surgical frame.

Rather than using the cart portion 502, the post portion 504, the head portion 506, the C-arm portion 508, the extension portion 510, and/or the base portion 512 to position the emitter E and receiver R with respect to one another, the emitter E can be attached to and positioned relative to the surgical frame 300, and the receiver R can be attached to and positioned relative to a receiver-support structure 550 in a radiation-scatter mitigating system 540 (FIGS. 37 and 38).

The receiver-support structure 550, as depicted in FIGS. 37 and 38, includes a first support post 552, a second support post 554, and a transom 556. The first support post 552 and the second support post 554 can be attached to and supported by the ground, and the transom 556 can be attached to and spaced from the ground by the first support post 552 and the second support post 554. Furthermore, the receiver-support structure 550 also can be used to support various surgical lights 557 thereon.

The receiver R is attached to the transom 556 using a truck 558. The transom 556 can serve as a track, and the truck 558 can be moveable along the track formed by the transom 556 to facilitate movement of the receiver R along the length of the transom 556. Using the movement of the truck 558 relative to the transom 556, the receiver R can be moved between adjacent the first support post 552 and adjacent the second support post 554.

Furthermore, the emitter E can be attached to the translating beam 302. As depicted in FIGS. 37 and 38, for example, the emitter E is attached to a base portion 560, and the base portion 560 is attached to the translating beam 302. A track (not shown) can be used to attach the base portion 560 to the translating beam 302 to facilitate movement of the base portion 560 (and the emitter E attached thereto) along the length of the translating beam 302. Using the track portion attached to the translating beam 302, the emitter E can be moved between adjacent the first end member 310 and adjacent the second end member 312.

The locations of the emitter E and the receiver R can be synchronized to facilitate the imaging techniques applied to the patient P. The synchronization of the emitter E and the receiver R can be facilitated via movement of the translating beam 302, movement of the emitter E along the track portion attached to the translating beam 302, and movement of the receiver R via movement of the truck 558 along the transom 556.

Furthermore, the emitter E and/or the receiver R could be moveable upwardly and downwardly toward or away from one another and the patient P using a modified first support portion 552, a modified second support post 554, a modified truck 558, and/or a modified base portion 560. The modified first support portion 552, the modified second support post 554, the modified truck 558, and/or the modified base portion 560 can be configured to be telescopically expandable and contractable to facilitate movement of the emitter E and/or the receiver R relative to one another and the patient P.

Rather than being attached to the translating beam 302, the base portion 560 or the modified base portion 560 could be attached to a slide bar (not shown) that is attached to the translating beam 302. The slide bar could be arranged transversely to and extend on either or both of the lateral sides of the translating beam 302. To facilitate positioning of the emitter E, the slide bar could be moveable along the translating beam 302 using a track (not shown) from between a location at least adjacent the first end member 310 and at least adjacent the second end member 312, and the base portion 560 or the modified base portion 560 could be moveable along the slide bar using a track (not shown) from between a location adjacent a first end of the slide bar and a location adjacent a second end of the slide bar.

Furthermore, a fixed beam (rather the translating beam 302) that extends between, for example, the first end member 310 and the second end member 312 could be used with the slide bar. Movement of the slide bar on the fixed beam from between a location at least adjacent the first end member 310 and at least adjacent the second end member 312, and movement of the base portion 560 and the modified base portion 560 on the slide bar from between a location adjacent a first end of the slide bar and a location adjacent a second end of the slide bar can afford similar positioning of the emitter E as with the translating beam 302 and the track provided thereon.

The radiation shield 416, the first radiation shield 456, and/or the second radiation shield 458, along with the first support post portions 410, 450, 530, 534, and the second support post portions 412, 452, 532, and 536 of the radiation-scatter mitigating systems 400 and 520 can be used with the radiation-scatter mitigating system 540 to intercept/block and mitigate, as discussed above, at least some of the scatter of the electromagnetic radiation from the emitter E. As depicted in FIGS. 37 and 38, the radiation shield 416 is used with the first support post 410 and the second support post 412, and the first radiation shield 456 and the second radiation shield 458 is used with the first support post 450 and the second support post 452. Additional radiation shields (not shown) can be used with the radiation-scatter mitigating system 540 and be provided at either end of the surgical frame 300 to further intercept/block radiation scatter, and these additional radiation shields have configurations and be supported in similar fashion to the radiation shield 416, the first radiation shield 456, and/or the second radiation shield 458.

Rather that being attached relative to the ground, a modified receiver-support structure 550' could be attached to the surgical frame 300 in a radiation-scatter mitigating system 540'. The modified receiver-support structure 550' can include some of the componentry of the receiver-support structure 550 and similar element numbering is applied to indicate similar features of the modified receiver-support structure 550'.

Figure 39:
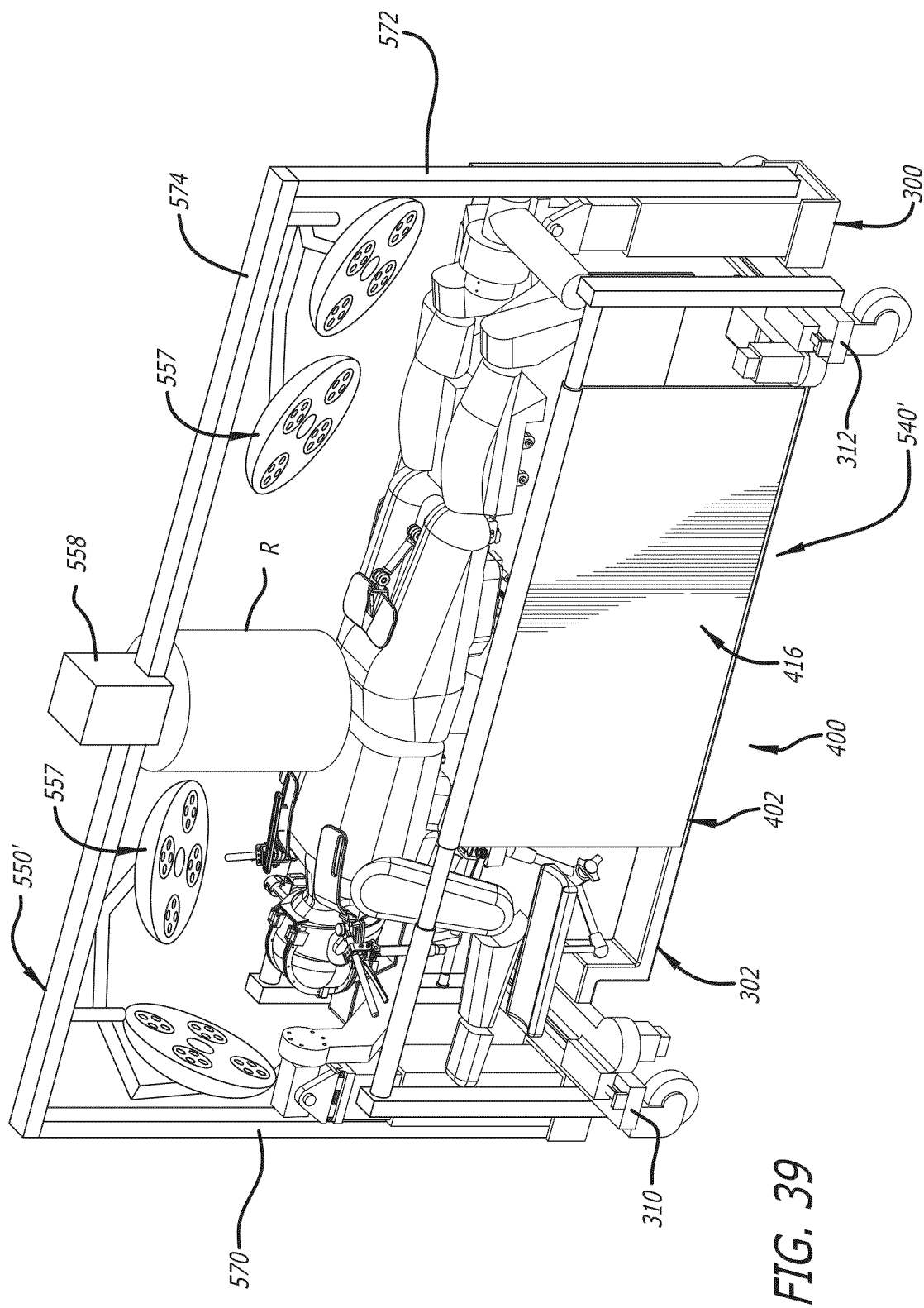
FIG. 39 is a top perspective view that illustrates a first side of a fourth embodiment of a radiation-scatter mitigating system, for mitigating radiation from a radiation emitter, that is at least partially integrated into a surgical fame, illustrates a receiver-support structure that also is at least partially integrated into the surgical frame.
Figure 40:
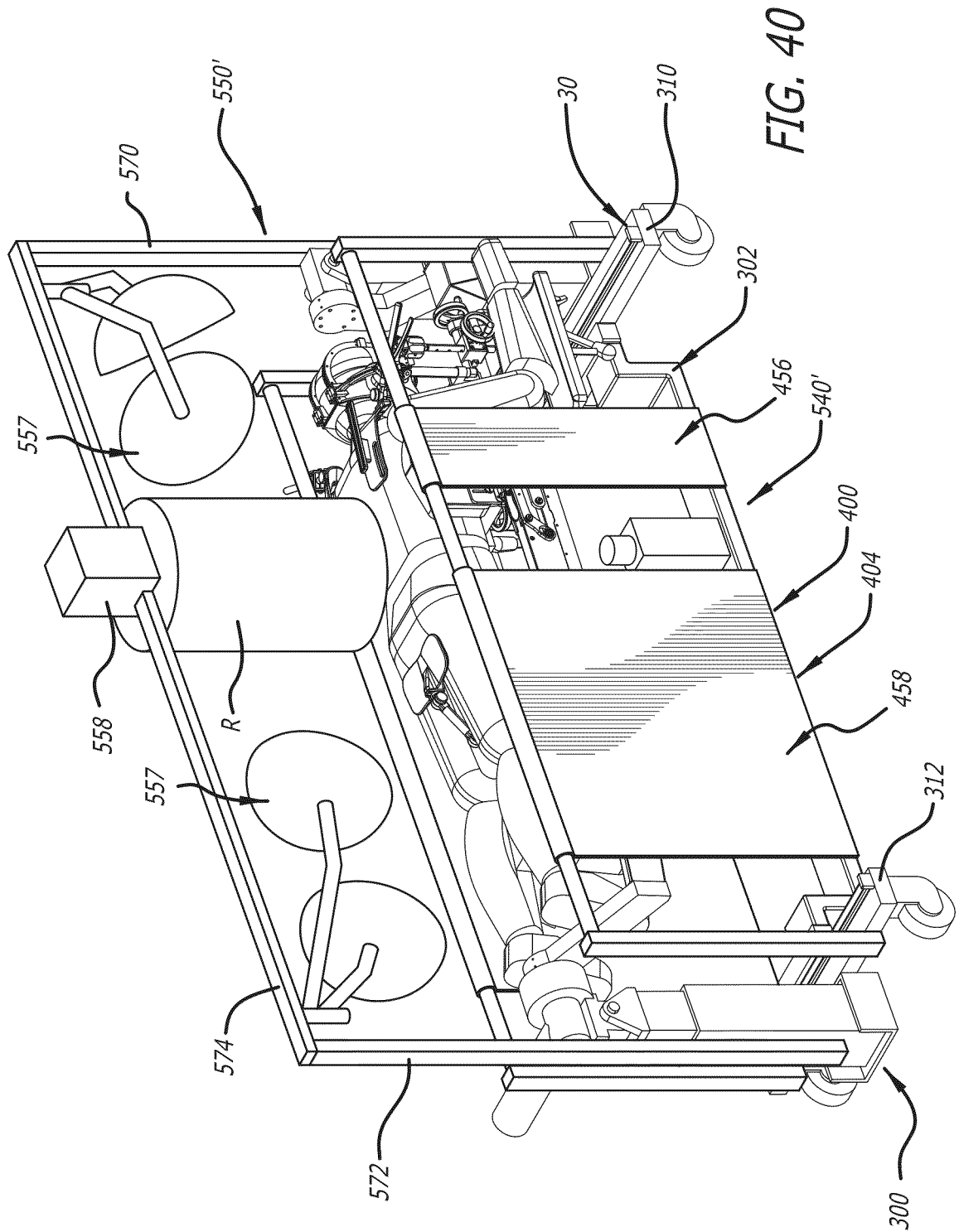
FIG. 40 is a top perspective view that illustrates a second side of the fourth embodiment of the radiation-scatter mitigating system of FIG. 39.

As depicted FIGS. 39 and 40, the modified receiver-support structure 550' includes a first support post 570, a second support post 572, and a transom 574 extending between the first support post 570 and the second support post 572. Furthermore, the modified receiver-support structure 550' can be attached to the surgical frame 300 at one longitudinal end via attachment of the first support post 570 to the first vertical support post 308A, and attached to the surgical frame 300 at the other longitudinal end via attachment of the second support post 572 to the second vertical support post 308B. As such, the first vertical support post 308A and the second vertical support post 308B serve in supporting the modified receiver-support structure 550' so the that the modified receiver-support structure 550' can be moved with the surgical frame 300 using the casters 318. And while the modified receiver-support structure 550' is shown attached to the first vertical support post 508A and the second vertical support post 308B, the attachment of the modified receiver-support structure 550' is not so limited. The modified receiver support structure 550' can be attached to other portions of the surgical frame 300.

The emitter E and/or the receiver R could be moveable upwardly and downwardly toward or away from one another and the patient P using a modified first support post 570, a modified second support post 572, a modified truck 558, and/or a modified base portion 560 that are telescopically expandable and contractable to facilitate movement of the emitter E and/or the receiver R relative to one another and the patient P. Furthermore, the modified receiver-support structure 550' also can be used to support various surgical lights 580 thereon, and the above-discussed slide bar and/or the fixed main beam could be used with the modified-receiver support structure 550'.

The above-discussed movement of the emitter E and the receiver R with respect to the patient P, and/or the rotation of the main beam 12 (and the patient P supported by the main beam 12) afford positioning of the emitter E and the receiver R in position relative to the patient P. Such movement and rotation facilitates the imaging of certain portions of the patient's body, and the above-discussed radiation shields serve in intercepting/blocking and mitigating radiation scatter from the emitter E directed toward the patient P.

Furthermore, the attachment locations of the emitter E and the receiver R can be reversed in their positions on the C-arm assembly 500, the translating beam 302, and the receiver-support structures 550 and 550'. The positioning and repositioning of the relocated emitter E and the relocated receiver R can then be effectuated as described above. Also, one or more robotic arms (not shown) could be attached in locations on the C-arm assembly 500, the translating beam 302, and/or the receiver-support structures 550 and 550' in place of or in addition to the emitter E and the receiver R. The one or more robotic arms could also be moveably attached to the main beam 12 to facilitate movement thereof from at least adjacent one end of the main beam 12 to at least adjacent the other end of the main beam 12. The robotic arms can be used in manipulating instruments, supporting the patient P, and/or supporting the emitter E and/or the receiver R.

Manual adjustment and controlled automation can be used to facilitate movement of the translating beam 302, movement of the cart portion 502 relative to the translating beam 302, raising and lowering of the telescoping post portion 504 to facilitate movement of the head portion 506, movement of the extension portion 510 and/or the base portion 512 (supporting the emitter E, the receiver R, and/or the one or more robotic arms) relative to the translating beam 302, movement of the emitter E and/or the receiver R relative to the transoms 556 and 574, and/or movement of the base portion 560 (supporting emitter E, the receiver R, and/or the one or more robotic arms) relative to the translating beam 302. The expansion and contraction of the radiation shield 416, the first radiation shield 456, the second radiation shield 458, and/or the other additional radiation shields discussed herein can also be effectuated using manual adjustment and controlled automation. When using controlled automation, actuators, such as servomotors, can be used to facilitate the mechanical articulations and movements described above.

In addition to or in place of the above-discussed radiation shields, a shield or shields can be positioned around the emitter E. The shield or shields can create an area that increases in size further and further from emitter E to facilitate unblocked radiation emission from the emitter E to the patient P, but that shields areas around the shield or shields. For example, the shield or shields can define a first cross-sectional area adjacent to the emitter E in a first plane perpendicular to the direction of radiation emission from the emitter E, and a second cross-sectional area removed from the emitter E in a second plane perpendicular to the direction of the radiation emission from the emitter E, where the first cross-sectional area is smaller than the second cross-sectional area. For example, the shield or shields could be frusto-conical or truncated-pyramidal shaped.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A surgical frame incorporating at least a portion of an electromagnetic-radiation imaging device in combination with a radiation-mitigation system, the combination of the surgical frame and the radiation-mitigation system comprising: the surgical frame comprising a first support portion, a second support portion, a rotatable patient-supporting beam, a translating beam, a first transom support post, a second transom support post, a transom, and the electromagnetic-radiation imaging device, the rotatable patient-supporting beam being spaced from a ground by and rotatable between the first support portion and the second support portion, the translating beam being positioned under the rotatable patient-supporting beam, and being moveably attached at a first end thereof relative to the first support portion and moveably attached at a second end thereof relative to the second support portion, the first transom support post being attached to the first support portion, the second transom support post being attached to the second support portion, the transom extending between the first transom support post and the second transom support post, the electromagnetic-radiation imaging device including an emitter and a receiver, one of the emitter and the receiver being supported and moveably attached relative to the translating beam underneath the rotatable patient-supporting beam, and the other of the emitter and the receiver being supported by and moveably attached to the transom over the rotatable patient-supporting beam; and the radiation-mitigation system comprising a first bar support portion attached to the first support portion of the surgical frame, a second bar support portion attached to the second support portion of the surgical frame, a first bar portion having a first end and a second end, and extending between the first bar support portion and the second bar support portion, and a first radiation shield supported by the first bar portion and being expandable and contractable along the first bar portion adjacent a first lateral side of the surgical frame; wherein the translating beam and the one of the emitter and the receiver attached thereto are moveable between a first position at or adjacent the first lateral side of the surgical frame and a second position at or adjacent an opposite second lateral side of the surgical frame, the one of the emitter and the receiver is moveable along the translating beam between a first position at or adjacent the first support portion and a second position at or adjacent the second support portion, and the other of the emitter and the receiver is moveable along the transom between a first position at or adjacent the first transom support post and a second position at or adjacent the second transom support post; and wherein the rotatable patient-supporting beam is rotatable independently of the first radiation shield of the radiation-mitigation system.

2. The combination of claim 1, wherein:
the first end of the first bar portion is directly supported by the first bar support portion and the second end of the first bar portion is directly supported by the second bar support portion, and
the first radiation shield hangs down from the first bar portion to at least partially cover a portion of the first lateral side of the surgical frame.

3. The combination of claim 1, the radiation-mitigation system further comprising:
a third bar support portion attached to the first support portion of the surgical frame,
a fourth bar support portion attached to the second support portion of the surgical frame,
a second bar portion having a first end and a second end, and extending between the third bar support portion and the fourth bar support portion, and a second radiation shield supported by the second bar portion and being expandable and contractable along the second bar portion adjacent the second lateral side of the surgical frame.

4. The combination of claim 3, wherein:
the first end of the second bar portion is directly supported by the third bar support portion and the second end of the second bar portion is directly supported by the fourth bar support portion, and
the second radiation shield hangs down from the second bar portion to at least partially cover a portion of the second lateral side of the surgical frame.

5. The combination of claim 4, wherein each of the first radiation shield and the second radiation shield comprises a radiation-attenuating material serving to limit propagation of radiation therethrough.

6. The combination of claim 1, wherein the emitter is supported relative to the translating beam, and wherein the translating beam is moveable to position at least the emitter relative to a patient supported on the rotatable patient-supporting beam.

7. The combination of claim 6, wherein the emitter is moveable relative to the translating beam via a track attached to the translating beam.

8. The combination of claim 7, wherein the receiver is supported relative to the transom, and the receiver is moveable relative to the transom via a track attached to the transom.

9. A surgical frame incorporating at least a portion of an electromagnetic-radiation imaging device in combination with a radiation-mitigation system, the combination of the surgical frame and the radiation-mitigation system comprising: the surgical frame comprising a first support portion, a second support portion, a rotatable patient-supporting beam, a translating beam, a first transom support post, a second transom support post, a transom, and the electromagnetic-radiation imaging device, the rotatable patient-supporting beam extending between and being rotatable relative to the first support portion and the second support portion, the translating beam being moveably attached at a first end thereof relative to the first support portion and moveably attached at a second end thereof relative to the second support portion, the first transom support post being attached to the first support portion, the second transom support post being attached to the second support portion, the transom extending between the first transom support post and the second transom support post, the electromagnetic-radiation imaging device including an emitter and a receiver, one of the emitter and the receiver being supported and moveably attached relative to the translating beam, and the other of the emitter and the receiver being supported by and moveably attached to the transom; and the radiation-mitigation system comprising a first bar support portion attached to the first support portion of the surgical frame, a second bar support portion attached to the second support portion of the surgical frame, a first bar portion having a first end and a second end, and extending between the first bar support portion and the second bar support portion, and a first radiation shield supported by the first bar portion and being expandable and contractable along the first bar portion adjacent a first lateral side of the surgical frame; wherein the translating beam and the one of the emitter and the receiver attached thereto are moveable between a first position at or adjacent the first lateral side of the surgical frame and a second position at or adjacent an opposite second lateral side of the surgical frame, the one of the emitter and the receiver is moveable along the translating beam between a first position at or adjacent the first support portion and a second position at or adjacent the second support portion, and the other of the emitter and the receiver is moveable along the transom between a first position at or adjacent the first transom support post and a second position at or adjacent the second transom support post; and wherein the rotatable patient-supporting beam is rotatable independently of the first radiation shield of the radiation-mitigation system.

10. The combination of claim 9, wherein the emitter is supported relative to the translating beam, and wherein the translating beam is moveable to position at least the emitter relative to a patient supported on the rotatable patient-supporting beam.

11. The combination of claim 10, wherein the emitter is moveable relative to the translating beam via a track attached to the translating beam.

12. The combination of claim 11, wherein the receiver is supported relative to the transom, and the receiver is moveable relative to the transom via a track attached to the transom.

13. The combination of claim 9, wherein:
the first end of the first bar portion is directly supported by the first bar support portion and the second end of the first bar portion is directly supported by the second bar support portion, and
the first radiation shield hangs down from the first bar portion to at least partially cover a portion of the first lateral side of the surgical frame.

14. The combination of claim 9, the radiation mitigation system further comprising:
a third bar support portion attached to the first support portion of the surgical frame,
a fourth bar support portion attached to the second support portion of the surgical frame,
a second bar portion having a first end and a second end, and extending between the third bar support portion and the fourth bar support portion, and
a second radiation shield supported by the second bar portion and being expandable and contractable along the second bar portion adjacent the second lateral side of the surgical frame.

15. The combination of claim 14, wherein:
the first end of the second bar portion is directly supported by the third bar support portion and the second end of the second bar portion is directly supported by the fourth bar support portion, and
the second radiation shield hangs down from the second bar portion to at least partially cover a portion of the second lateral side of the surgical frame.

16. A surgical frame incorporating at least a portion of an electromagnetic-radiation imaging device in combination with radiation-mitigation system, the combination of the surgical frame and the radiation-mitigation system, comprising:
a first support portion, a second support portion, a rotatable patient-supporting beam extending between the first support portion and the second support portion, a first transom support post, a second transom support post, a transom, and the electromagnetic-radiation imaging device, the rotatable patient-supporting beam being rotatably attached at a first end thereof relative to the first support portion and rotatably attached at a second end thereof relative to the second support portion, the first transom support post being attached to the first support portion, the second transom support post being attached to the second support portion, the transom extending between the first transom support post and the second transom support post, the electromagnetic-radiation imaging device including an emitter and a receiver, the emitter being supported by the surgical frame under the rotatable patient-supporting beam, and the receiver being supported by and moveably attached to the transom; and the radiation-mitigation system comprising a first bar support portion attached to the first support portion of the surgical frame, a second bar support portion having a first end and a second end, and extending between the first bar support portion and the second bar support portion, and a first radiation shield supported by the first bar portion and being expandable and contractable along the first bar portion adjacent a first lateral side of the surgical frame;

wherein the receiver is moveable along the transom between a first position at or adjacent the first transom support post and a second position at or adjacent the second transom support post; and wherein the rotatable patient-supporting beam is rotatable independently of the first radiation shield of the radiation-mitigation system.

17. The combination of claim 16, wherein the receiver is moveable relative to the transom via a track attached to the transom.

18. The combination of claim 16, the radiation-mitigation system further comprising:
   a third bar support portion attached to the first support portion of the surgical frame,
   a fourth bar support portion attached to the second support portion of the surgical frame,
   a second bar portion having a first end and a second end, and extending between the third bar support portion and the fourth bar support portion, and
   a second radiation shield supported by the second bar portion and being expandable and contractable along the second bar portion adjacent a second lateral side of the surgical frame.

19. The combination of claim 18, wherein:
   the first radiation shield hangs down from the first bar portion to at least partially cover a portion of the first lateral side of the surgical frame; and
   the second radiation shield hangs down from the second bar portion to at least partially cover a portion of the second lateral side of the surgical frame.

20. The combination of claim 19, wherein each of the first radiation shield and the second radiation shield comprises a radiation-attenuating material serving to limit propagation of radiation therethrough.

\* \* \* \* \*